US009324953B2

United States Patent
Kim et al.

(10) Patent No.: US 9,324,953 B2
(45) Date of Patent: Apr. 26, 2016

(54) CONDENSED-CYCLIC COMPOUNDS AND ORGANIC LIGHT-EMITTING DIODES COMPRISING THE SAME

(71) Applicant: SAMSUNG DISPLAY CO., LTD., Yongin, Gyeonggi-do (KR)

(72) Inventors: Se-Hun Kim, Yongin (KR); Mi-Kyung Kim, Yongin (KR); Chang-Woong Chu, Yongin (KR); Kwan-Hee Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 270 days.

(21) Appl. No.: 13/765,911

(22) Filed: Feb. 13, 2013

(65) Prior Publication Data

US 2014/0034916 A1 Feb. 6, 2014

(30) Foreign Application Priority Data

Jul. 31, 2012 (KR) .................. 10-2012-0084190

(51) Int. Cl.
*H01L 51/50* (2006.01)
*H01L 51/00* (2006.01)
*C07D 471/22* (2006.01)

(52) U.S. Cl.
CPC .......... *H01L 51/0072* (2013.01); *C07D 471/22* (2013.01); *H01L 51/0067* (2013.01); *H01L 51/0071* (2013.01); *H01L 51/5016* (2013.01); *H01L 51/5064* (2013.01)

(58) Field of Classification Search
None
See application file for complete search history.

(56) References Cited

U.S. PATENT DOCUMENTS

| 2009/0165848 A1 | 7/2009 | Yoon et al. |
| 2011/0062429 A1 | 3/2011 | Kai et al. |
| 2011/0062862 A1 | 3/2011 | Yamamoto et al. |
| 2013/0026422 A1* | 1/2013 | Parham et al. ............. 252/500 |

FOREIGN PATENT DOCUMENTS

| KR | 10-2007-0056829 A | 6/2007 |
| KR | 10-2010-0105099 A | 9/2010 |
| KR | 10-2011-0009920 A | 1/2011 |
| KR | 10-2011-0010099 A | 1/2011 |
| KR | 10-2011-0010750 A | 2/2011 |
| KR | 10-2011-0066763 A | 6/2011 |
| KR | 10-2001-0111692 | * 10/2011 ............. H01L 51/50 |
| KR | 10-2011-0110508 A | 10/2011 |
| KR | 10-2011-0113470 A | 10/2011 |
| KR | 10-2011-0117547 A | 10/2011 |
| KR | 10-2011-0120994 A | 11/2011 |
| WO | 2010/107244 A2 | 9/2010 |
| WO | 2011/010844 A1 | 1/2011 |
| WO | 2011/136520 A1 | 11/2011 |

OTHER PUBLICATIONS

Tang, et al.,Organic Electroluminescent Diodes, Applied Physics Letters, Sep. 21, 1987, pp. 913-915, vol. 51, American Institute of Physics.

* cited by examiner

*Primary Examiner* — Gregory Clark
(74) *Attorney, Agent, or Firm* — Robert E. Bushnell, Esq.

(57) ABSTRACT

Condensed-cyclic organic compounds, synthetic methods for preparing the same and an organic light-emitting diode including the same are presented. The subject polycyclic triarylamines are prepared via a series of substitution and cyclization reactions.

16 Claims, 1 Drawing Sheet

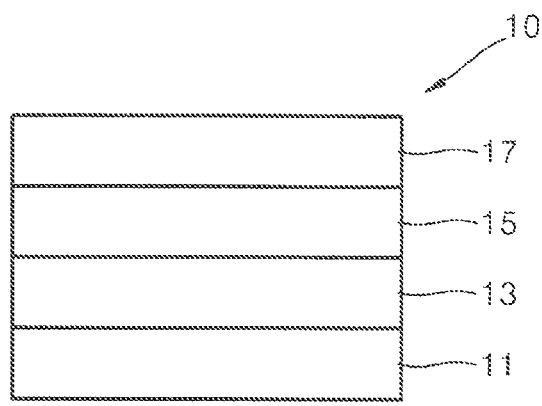

CONDENSED-CYCLIC COMPOUNDS AND ORGANIC LIGHT-EMITTING DIODES COMPRISING THE SAME

CLAIM OF PRIORITY

This application makes reference to, incorporates the same herein, and claims all benefits accruing under 35 U.S.C. §119 from an application for CONDENSED-CYCLIC COMPOUND AND ORGANIC LIGHT-EMITTING DIODE COMPRISING THE SAME earlier filed in the Korean Intellectual Property Office on 31 Jul. 2012 and there duly assigned Serial No. 10-2012-0084190.

BACKGROUND OF THE INVENTION

1. Field of the Invention

Compounds for organic light-emitting diodes and organic light-emitting diodes including the same are provided.

2. Description of the Related Art

Organic light-emitting diodes (OLEDs), which are self-emitting devices, have advantages such as a wide viewing angle, excellent contrast, quick response, high brightness, and excellent driving voltage characteristics and can provide multicolored images.

A general organic light-emitting diode has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an organic light-emitting diode having the above-described structure is as follows.

When a voltage is applied between the anode and the cathode, holes injected from the anode move to the EML via the HTL, and electrons injected from the cathode move to the EML via the ETL. Carriers such as the holes and electrons recombine in the EML to generate excitons. When the excitons drop from an excited state to a ground state, light is emitted.

SUMMARY OF THE INVENTION

According to one embodiment of the present invention, there is provided a condensed-cyclic compound represented by Formula 1 below.

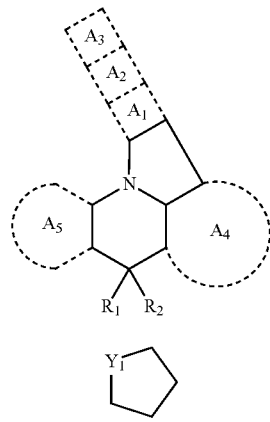

Formula 1

Formula 2

In Formula 1, ring $A_1$, ring $A_2$, and ring $A_3$ are condensed with each other;

ring $A_2$ is represented by Formula 2, $Y_1$ being O, S, or $N\text{-}(L_1)_{aa}\text{-}(R_{11})_{ab}$;

ring $A_1$, ring $A_3$, ring $A_4$, and ring $A_5$ are each independently selected from a substituted or unsubstituted benzene ring and a substituted or unsubstituted naphthalene ring;

$R_1$ and $R_2$ are each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1\text{-}C_{60}$ alkyl group, a substituted or unsubstituted $C_2\text{-}C_{60}$ alkenyl group, a substituted or unsubstituted $C_2\text{-}C_{60}$ alkynyl group, a substituted or unsubstituted $C_1\text{-}C_{60}$ alkoxy group, a substituted or unsubstituted $C_3\text{-}C_{10}$ cycloalkyl group, a substituted or unsubstituted $C_3\text{-}C_{10}$ cycloalkenyl group, a substituted or unsubstituted $C_6\text{-}C_{60}$ aryl group, a substituted or unsubstituted $C_6\text{-}C_{60}$ aryloxy group, a substituted or unsubstituted $C_6\text{-}C_{60}$ arylthio group, and a substituted or unsubstituted $C_2\text{-}C_{60}$ heteroaryl group, $R_1$ and $R_2$ being non-ring forming substituents which are not linked to each other and do not form a ring;

$L_1$ is a substituted or unsubstituted $C_6\text{-}C_{60}$ arylene group or a substituted or unsubstituted $C_2\text{-}C_{60}$ heteroarylene group;

aa is an integer from 0 to 5;

$R_{11}$ is a substituted or unsubstituted $C_3\text{-}C_{10}$ cycloalkyl group, a substituted or unsubstituted $C_3\text{-}C_{10}$ cycloalkenyl group, a substituted or unsubstituted $C_6\text{-}C_{60}$ aryl group, or a substituted or unsubstituted $C_2\text{-}C_{60}$ heteroaryl group; and ab is an integer from 1 to 10.

According to another embodiment of the present invention, there is provided an organic light-emitting diode including: a first electrode; a second electrode disposed opposite to the first electrode; and an organic layer interposed between the first electrode and the second electrode, the organic layer including at least one condensed-cyclic compound.

BRIEF DESCRIPTION OF THE DRAWING

The above and other features and advantages of the present invention will become more apparent by describing in detail exemplary embodiments thereof with reference to the attached drawing in which:

FIG. 1 is a schematic cross-sectional view of an organic light-emitting diode according to an embodiment of the present invention.

DETAILED DESCRIPTION OF THE INVENTION

Hereinafter, the present invention will be described more fully with reference to the accompanying drawing, in which an exemplary embodiment of the invention is shown.

As used herein, the term "and/or" includes any and all combinations of one or more of the associated listed items. Expressions such as "at least one of", when preceding a list of elements, modify the entire list of elements and do not modify the individual elements of the list.

A condensed-cyclic compound according to an embodiment of the present invention is represented by Formula 1 below.

Formula 1

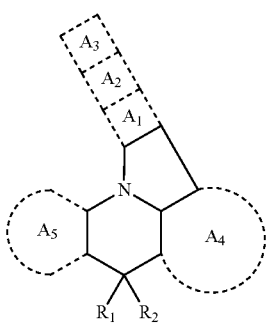

In Formula 1, ring $A_1$, ring $A_2$, and ring $A_3$ are condensed with each other. Each of the ring $A_1$, ring $A_4$, and ring $A_5$ are condensed with a neighboring ring.

In Formula 1, the ring $A_2$ is represented by Formula 2 below. In Formula 2, $Y_1$ may be O, S, or N-$(L_1)_{aa}$-$(R_{11})_{ab}$. In this regard, $L_1$, aa, $R_{11}$, and ab will be described later.

Formula 2

In Formula 1, the ring $A_1$, ring $A_3$, ring $A_4$, and ring $A_5$ may be each independently selected from a substituted or unsubstituted benzene ring and a substituted or unsubstituted naphthalene ring.

In Formula 1, the ring $A_1$, ring $A_2$, ring $A_3$, ring $A_4$, and ring $A_5$ may have various structures according to the condensation methods used in their preparation.

For example, the compound of Formula 1 may be represented by Formula 3 or 4, depending upon the condensation method used to form the ring $A_2$.

Formula 3

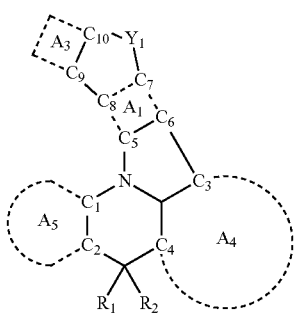

Formula 4

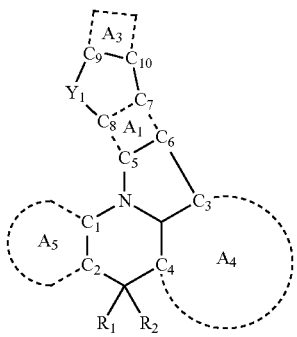

In Formulae 3 and 4, $C_1$ to $C_{10}$ indicate chemically distinct carbon atoms numbered to be distinguished from one another.

In Formulae 3 and 4, the ring $A_1$ may be represented by one of Formulae 5(1) to 5(5).

Formula 5(1)

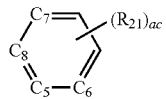

Formula 5(2)

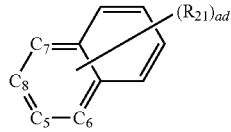

Formula 5(3)

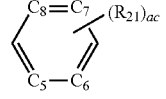

Formula 5(4)

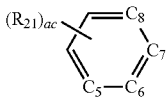

Formula 5(5)

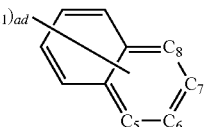

In Formulae 5(1) to 5(5), ac may be 1 or 2, and ad may be an integer from 1 to 4. If ac is 2, two $R_{21}$'s may be the same or different. If ad is 2 or greater, more than two $R_{21}$'s may be the same or different.

In Formulae 3 and 4, the ring $A_3$ may be represented by one of Formulae 6(1) to 6(4) below.

Formula 6(1)

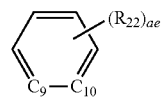

Formula 6(2)

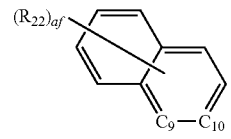

Formula 6(3)

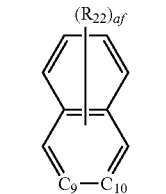

Formula 6(4)

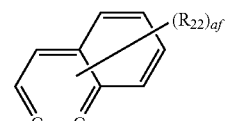

In Formulae 6(1) to 6(4), ae may be an integer from 1 to 4, and af may be an integer from 1 to 6. If ae is 2 or greater, more than two $R_{22}$'s may be the same or different. If af is 2 or greater, more than two $R_{22}$'s may be the same or different.

In Formulae 3 and 4, the ring $A_4$ may be represented by one of Formulae 7(1) to 7(3) below.

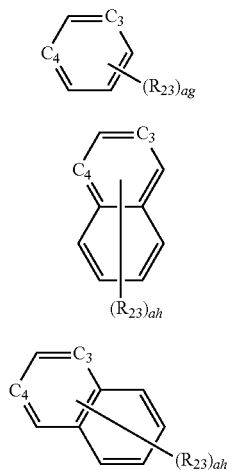

Formula 7(1)

Formula 7(2)

Formula 7(3)

In Formulae 7(1) to 7(3), ag may be an integer from 1 to 3, and ah may be an integer from 1 to 5. If ag is 2 or greater, more than two $R_{23}$'s may be the same or different. If ah is 2 or greater, more than two $R_{23}$'s may be the same or different.

In Formulae 3 and 4, the ring $A_5$ may be represented by one of Formulae 8(1) to 8(4) below.

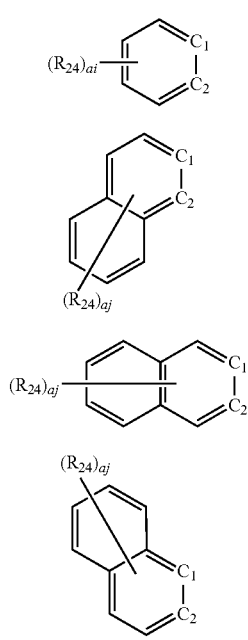

Formula 8(1)

Formula 8(2)

Formula 8(3)

Formula 8(4)

In Formulae 8(1) to 8(4), ai may be an integer from 1 to 4, and aj may be an integer from 1 to 7. If ai is 2 or greater, more than two $R_{24}$'s may be the same or different. If aj is 2 or greater, more than two $R_{24}$'s may be the same or different.

The locations of the carbon atoms represented as $C_1$ to $C_{10}$ in Formulae 5(1) to 5(5), 6(1) to 6(5), 7(1) to 7(3), and 8(1) to 8(4) are the same as those shown in Formulae 3 and 4.

In Formulae 5(1) to 5(5), 6(1) to 6(5), 7(1) to 7(3), and 8(1) to 8(4), $R_{21}$ to $R_{24}$ may be each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, and -$(L_2)_{ao}$-$(R_{12})_{ap}$. In this regard, in -$(L_2)_{ao}$-$(R_{12})_{ap}$, $L_2$ may be selected from a substituted or unsubstituted $C_6$-$C_{60}$ arylene group and a substituted or unsubstituted $C_2$-$C_{60}$ heteroarylene group, ao may be an integer from 0 to 5, $R_{12}$ may be selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted $C_2$-$C_{60}$ heteroaryl group, and ap may be an integer from 1 to 10.

For example, $R_{21}$ to $R_{24}$ may be each independently one of: hydrogen; deuterium; a halogen atom; a hydroxyl group; a cyano group; a nitro group; an amino group; an aminidino group; hydrazine; hydrazone; a carboxyl group or a salt thereof; a sulfonic acid group or a salt thereof; a phosphoric acid group or a salt thereof; a $C_1$-$C_{20}$ alkyl group (e.g., a methyl group, an ethyl group, a propyl group, a butyl group, a pentyl group, a hexyl group, a heptyl group, and an octyl group) and a $C_1$-$C_{20}$ alkoxy group (e.g., a methoxy group, an ethoxy group, a propoxy group, a butoxy group, and a pentoxy group); a $C_1$-$C_{20}$ alkyl group and a $C_1$-$C_{20}$ alkoxy group substituted with at least one of deuterium, a halogen atom, a hydroxyl group, a cyano group, a nitro group, an amino group, an aminidino group, hydrazine, hydrazone, a carboxyl group or a salt thereof, a sulfonic acid of a salt thereof, a phosphoric acid group or a salt thereof, a phenyl group, a naphthyl group, and an anthryl group; a $C_6$-$C_{14}$ aryl group (e.g., a phenyl group, a naphthyl group, and an anthryl group) and a $C_2$-$C_{14}$ heteroaryl group (e.g., a pyridinyl group, a pyrimidinyl group, a pyrazinyl group, and a triazinyl group); a $C_6$-$C_{14}$ aryl group and a $C_2$-$C_{14}$ heteroaryl group substituted with at least one of deuterium, a halogen atom, a hydroxyl group, a cyano group, a nitro group, an amino group, an aminidino group, hydrazine, hydrazone, a carboxyl group or a salt thereof, a sulfonic acid of a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and -$(L_2)_{ao}$-$(R_{12})_{ap}$, but are not limited thereto. In this regard, $L_2$ may be a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group; and ao may be 0, 1, or 2; and $R_{12}$ may be a substituted or unsubstituted 5-membered hetero ring, a substituted or unsubstituted 6-membered hetero ring, a substituted or unsubstituted 9-membered hetero ring, or a substituted or unsubstituted 10-membered hetero ring which include at least one nitrogen (N) as a ring-forming atom; and ap may be 1 or 2.

According to another embodiment of the present invention, $R_{21}$ to $R_{24}$ may be each independently one of: hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a phenyl group, a naphthyl group, an anthryl group, a pyridinyl group, a pyrimidinyl group, a pyrazinyl group, and a triazinyl group; a phenyl group, a naphthyl group, an anthryl group, a pyridinyl group, a pyrimidinyl group, a pyrazinyl group, and a triazinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and -$(L_2)_{ao}$-$(R_{12})_{ap}$. In this regard, $L_2$ may be one of: a phenylene group, a naphthylene group, a fluorenylene group, and an anthrylene group; and a phenylene group, a naphthylene group, a fluorenylene group, and an anthrylene group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; ao may be 0, 1, or 2; $R_{12}$ may be one of: a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group; and a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and ap may be 1 or 2, but they are not limited thereto.

According to an embodiment of the present invention, the condensed-cyclic compound may be represented by Formula 3, and the ring $A_1$ in Formula 3 may be represented by one of Formulae 5(1) to 5(3). The compounds of Formulae 5(1) to 5(3) are described above.

According to another embodiment of the present invention, the condensed-cyclic compound may be represented by Formula 3, the ring $A_1$ in Formula 3 may be represented by one of Formulae 5(1) to 5(3), the ring $A_3$ may be represented by one of Formulae 6(1) and 6(2), the $A_4$ ring may be represented by one of Formulae 7(1) and 7(3), and the $A_5$ ring may be represented by one of Formulae 8(1) and 8(3), but they are not limited thereto. The descriptions for Formulae 5(1) to 5(3), 6(1), 6(2), 7(1), 7(3), 8(1), and 8(3) are described above.

According to another embodiment of the present invention, the condensed-cyclic compound may be represented by Formula 4, and the ring $A_1$ in Formula 4 may be represented by Formula 5(3).

According to another embodiment of the present invention, the condensed-cyclic compound may be represented by Formula 4, the ring $A_1$ in Formula 4 may be represented by Formula 5(3), the ring $A_3$ may be represented by one of Formulae 6(1) and 6(2), the $A_4$ ring may be represented by one of Formulae 7(1) and 7(3), and the $A_5$ ring may be represented by one of Formulae 8(1) and 8(3), but they are not limited thereto. The description for Formulae 5(3), 6(1), 6(2), 7(1), 7(3), 8(1), and 8(3) are described above.

In Formula 2, $Y_1$ may be selected from O, S, and N-$(L_1)_{aa}$-$(R_{11})_{ab}$.

For example, in Formula 2, $Y_1$ may be N-$(L_1)_{aa}$-$(R_{11})_{ab}$.

In N-$(L_1)_{aa}$-$(R_{11})_{ab}$, $L_1$ may be selected from a substituted or unsubstituted $C_6$-$C_{60}$ aryl group and a substituted or unsubstituted $C_2$-$C_{60}$ heteroaryl group. For example, $L_1$ may be a substituted or unsubstituted $C_6$-$C_{60}$ aryl group.

According to the current embodiment, $L_1$ may be selected from a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group.

For example, $L_1$ may be selected from a substituted or unsubstituted phenylene group, a substituted or unsubstituted naphthylene group, a substituted or unsubstituted a fluorenylene group, a substituted or unsubstituted spiro-fluorenylene group, a substituted or unsubstituted an anthrylene group, and a substituted or unsubstituted pyrenylene group.

For example, $L_1$ may be one of: a phenylene group, a naphthylene group, a fluorenylene group, a spiro-fluorenylene group, an anthrylene group and pyrenylene group; and a phenylene group, a naphthylene group, a fluorenylene group, a spiro-fluorenylene group, an anthrylene group, and a pyrenylene group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl, a naphthyl group, and an anthryl group, but they are not limited thereto.

In N-$(L_1)_{aa}$-$(R_{11})_{ab}$, aa may be an integer from 0 to 5. For example, aa may be 0, 1, or 2. If aa is 2 or greater, more than two $L_1$'s may be the same or different.

In N-$(L_1)_{aa}$-$(R_{11})_{ab}$, $R_{11}$ may be selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted $C_2$-$C_{60}$ heteroaryl group.

$R_{11}$ may be selected from a substituted or unsubstituted $C_6$-$C_{14}$ aryl group and a substituted or unsubstituted $C_2$-$C_{60}$ heteroaryl group.

For example, $R_{11}$ may be selected from a substituted or unsubstituted 5-membered hetero ring, a substituted or unsubstituted 6-membered hetero ring, a substituted or unsubstituted 9-membered hetero ring, and a substituted or unsubstituted 10-membered hetero ring, each of which includes at least one nitrogen (N) as a ring-forming atom.

According to an embodiment, $R_{11}$ may be selected from a substituted or unsubstituted pyrrolyl group, a substituted or unsubstituted pyrazolyl group, a substituted or unsubstituted imidazolyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted benzoimidazolyl group, a substituted or unsubstituted quinolinyl group, and a substituted or unsubstituted isoquinolinyl group.

$R_{11}$ may be one of: a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group; and a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group, but they are not limited thereto.

In N-$(L_1)_{aa}$-$(R_{11})_{ab}$, $R_{11}$ may be represented by one of Formulae 9 to 15 below.

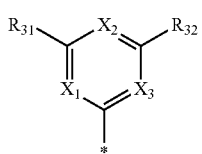

Formula 9

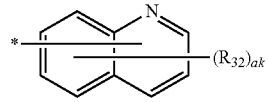

Formula 10

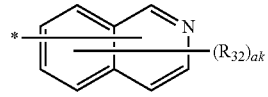

Formula 11

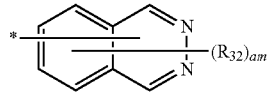

Formula 12

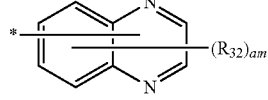

Formula 13

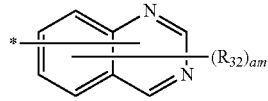

Formula 14

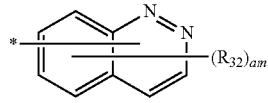

Formula 15

In Formulae 9 to 15, $X_1$ may be selected from N and $C(R_{33})$, $X_2$ may be selected from N and $C(R_{34})$, and $X_3$ may be selected from N and $C(R_{35})$, at least one of $X_1$, $X_2$, and $X_3$ may be N; $R_{31}$ to $R_{35}$ are each independently selected from hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; ak may be an integer from 1 to 6; am may be an integer from 1 to 5; and * may be a binding site to $L_1$ or nitrogen in $Y_1$.

In Formula 9, $X_1$ may be selected from N and $C(R_{33})$, $X_2$ may be selected from N and $C(R_{34})$, and $X_3$ may be selected from N and $C(R_{35})$, at least one of $X_1$, $X_2$, and $X_3$ may be N; $R_{31}$ to $R_{35}$ are each independently selected from hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group.

In Formula 9, for example, $X_1$, $X_2$ and $X_3$ are N; $X_1$ and $X_3$ are N, and $X_2$ may be $C(R_{34})$; or $X_1$ and $X_2$ are N, and $X_3$ may be $C(R_{35})$, but they are not limited thereto.

Meanwhile, in Formula 1, $Y_1$ may be selected from S and O. In this regard, in Formula 1, the ring $A_5$ may be represented by one of Formulae 8(1) to 8(4), and at least one of the ai $R_{24}$'s of Formula 8(1) and at least one of aj $R_{24}$'s of Formula 8(2) may be -$(L_2)_{ao}$-$(R_{12})_{ap}$ as described above. The -$(L_2)_{ao}$-$(R_{12})_{ap}$ is defined as described above.

For example, the condensed-cyclic compound of Formula 1 may be represented by Formula 3A below.

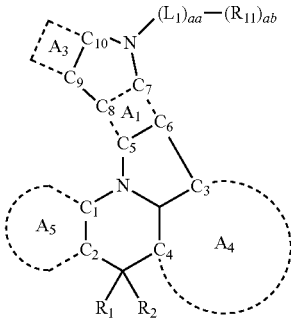

Formula 3A

In Formula 3A, the ring $A_1$ may be represented by any one of Formulae 5(1) to 5(5), the ring $A_3$ may be represented by any one of Formulae 6(1) to 6(4), the ring $A_4$ may be represented by any one of Formulae 7(1) to 7(3), and the ring $A_5$ may be represented by any one of Formulae 8(1) to 8(4). In this regard, in Formulae 5(1) to 5(5), 6(1) to 6(4), 7(1) to 7(3), and 8(1) to 8(4), $R_{21}$ to $R_{24}$ may be hydrogen.

Alternatively, in Formula 3A, the ring $A_1$ may be represented by any one of Formulae 5(1) to 5(3), the ring $A_3$ may be represented by any one of Formulae 6(1) and 6(2), the ring $A_4$ may be represented by any one of Formulae 7(1) and 7(3), and the ring $A_5$ may be represented by any one of Formulae 8(1) and 8(3). In this regard, in Formulae 5(1) to 5(3), 6(1), 6(2), 7(1), 7(3), and 8(1) and 8(3), $R_{21}$ to $R_{24}$ may be hydrogen.

Alternatively, the condensed-cyclic ring of Formula 1 may be represented by Formula 3B or 3C below.

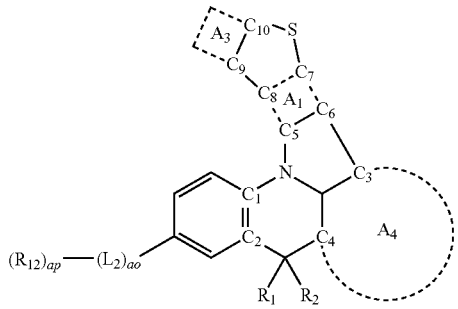

Formula 3B

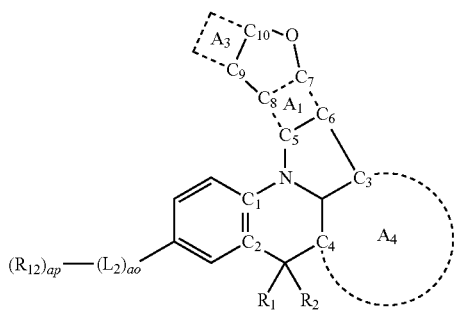

Formula 3C

In Formulae 3B and 3C, the ring $A_1$ may be represented by any one of Formulae 5(1) to 5(5), the ring $A_3$ may be represented by any one of Formulae 6(1) to 6(4), and the ring $A_4$ may be represented by any one of Formulae 7(1) to 7(3). In this regard, in Formulae 5(1) to 5(5), 6(1) to 6(4), and 7(1) to 7(3), $R_{21}$ to $R_{23}$ may be hydrogen. In Formulae 3B and 3C, $L_2$, ao, $R_{12}$, and ap are defined as described above.

Alternatively, in Formulae 3B and 3C, the ring $A_1$ may be represented by any one of Formulae 5(1) to 5(3), the ring $A_3$ may be represented by any one of Formulae 6(1) and 6(2), and the ring $A_4$ may be represented by any one of Formulae 7(1) and 7(3). In this regard, in Formulae 5(1) to 5(3), 6(1) to 6(2), and 7(1) to 7(3), $R_{21}$ to $R_{23}$ may be hydrogen. In Formulae 3B and 3C, $L_2$, ao, $R_{12}$, and ap are defined as described above.

In Formula 1, $R_1$ and $R_2$ are each independently selected from hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group and a substituted or unsubstituted $C_2$-$C_{60}$ heteroaryl group, $R_1$ and $R_2$ being non-ring forming substituents which are not linked to each other and do not form a ring. That is, in Formula 1, $R_1$ and $R_2$ are not linked to each other and do not form a ring.

In Formula 1, $R_1$ and $R_2$ may be each independently selected from a substituted or unsubstituted $C_1$-$C_{10}$ alkyl group, a substituted or unsubstituted $C_1$-$C_{10}$ alkoxy group and a substituted or unsubstituted $C_6$-$C_{14}$ aryl group.

For example, in Formula 1, $R_1$ and $R_2$ may be each independently one of: a $C_1$-$C_{20}$ alkyl group and a $C_1$-$C_{20}$ alkoxy group; a $C_1$-$C_{20}$ alkyl group and a $C_1$-$C_{20}$ alkoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a $C_6$-$C_{14}$ aryl group; or a $C_6$-$C_{14}$ aryl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group.

For example, in Formula 1, $R_1$ and $R_2$ may be each independently one of: a methyl group, an ethyl group, a propyl group, a butyl group, a pentyl group, a hexyl group, a heptyl group, an octyl group, a methoxy group, an ethoxy group, a propoxy group, a butoxy group, and a pentoxy group; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a phenyl group, a naphthyl group, and an anthryl group; and a phenyl group, a naphthyl group, and an anthryl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group.

According to an embodiment, the condensed-cyclic compound may be represented by any one of Formulae 3-1 to 3-27 below, but is not limited thereto.

Formula 3-1
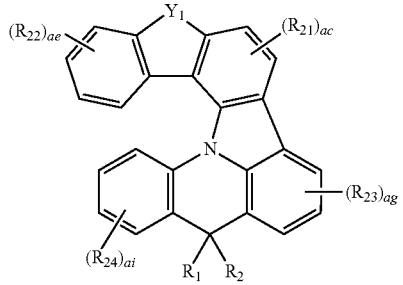

Formula 3-2
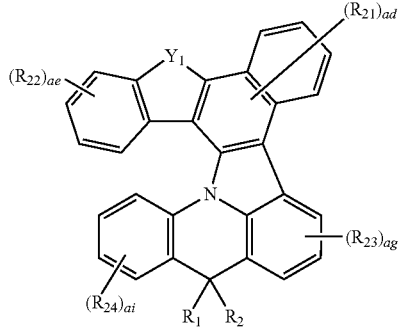

Formula 3-3
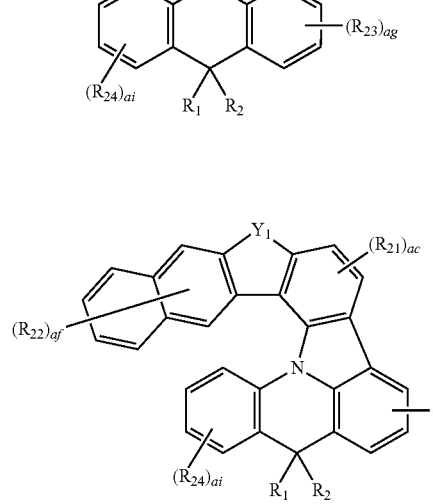

Formula 3-4
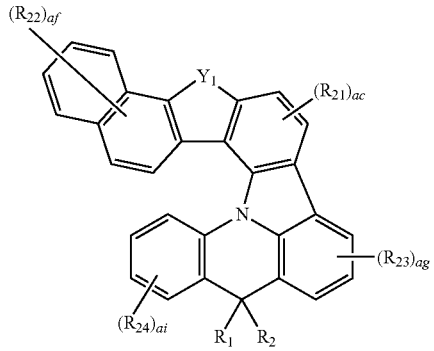

Formula 3-5
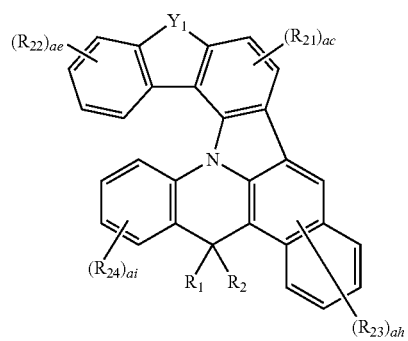

Formula 3-6
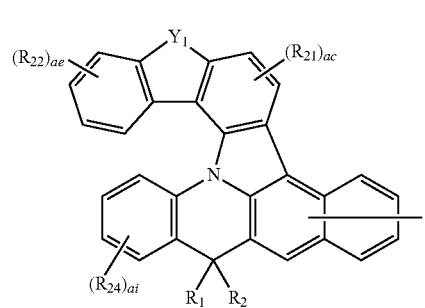

Formula 3-7
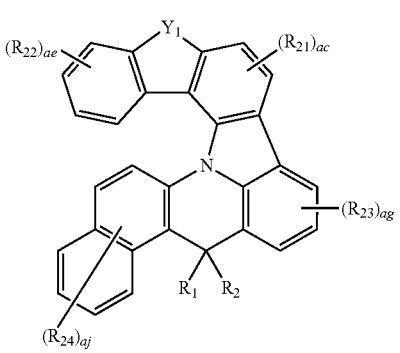

Formula 3-8

-continued
Formula 3-9
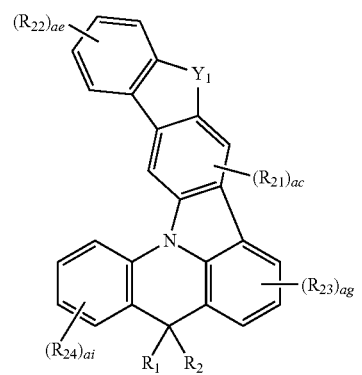
Formula 3-10
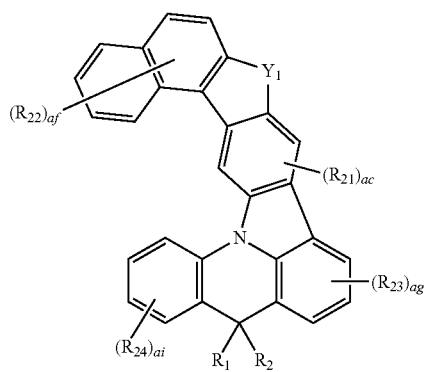
Formula 3-11
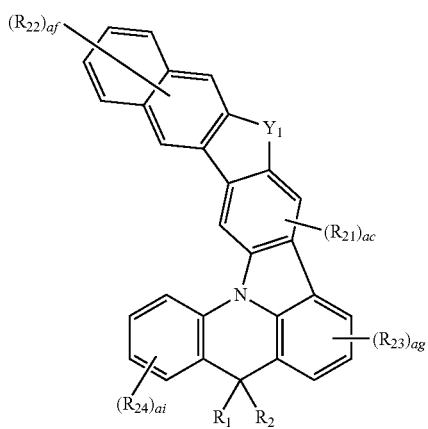
Formula 3-12
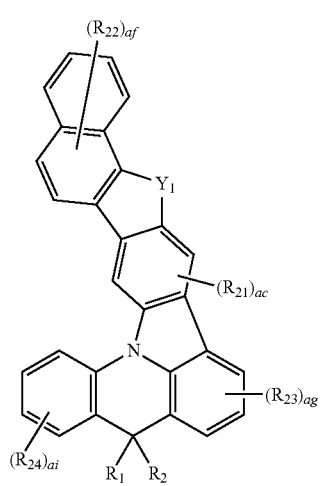
Formula 3-13
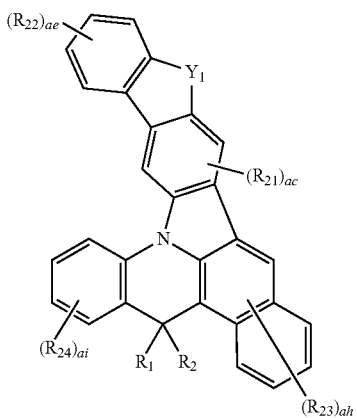
Formula 3-14
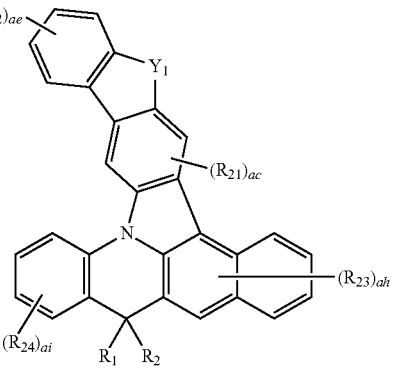
Formula 3-15
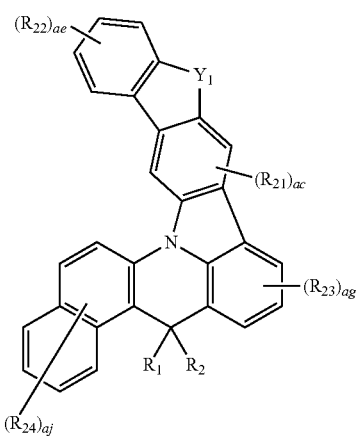
Formula 3-16
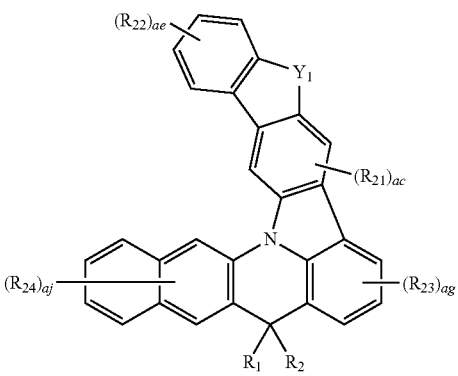

Formula 3-17
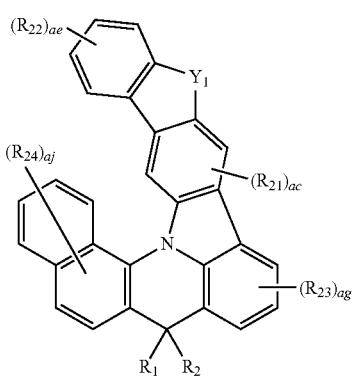
Formula 3-18
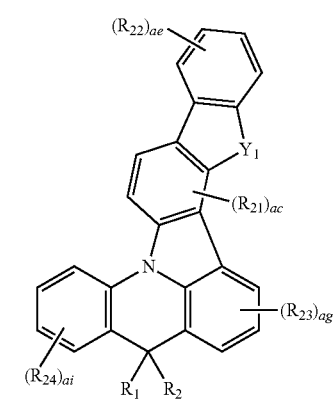
Formula 3-19
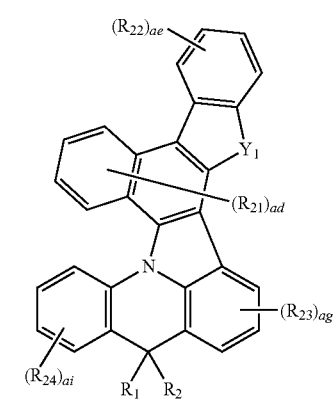
Formula 3-20
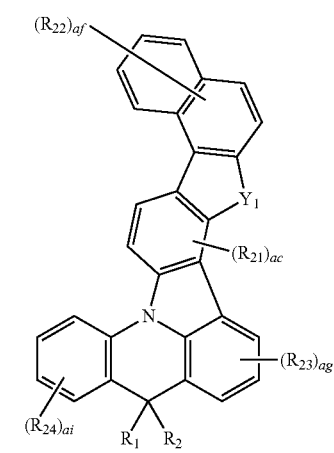
Formula 3-21
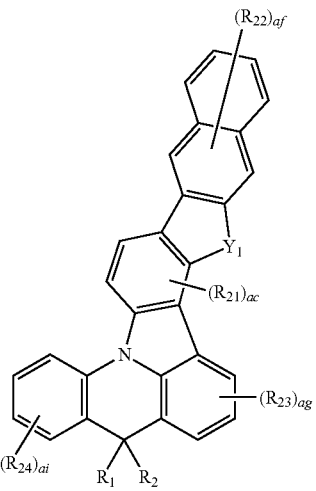
Formula 3-22
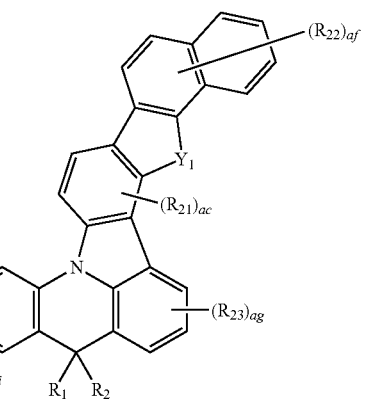
Formula 3-23
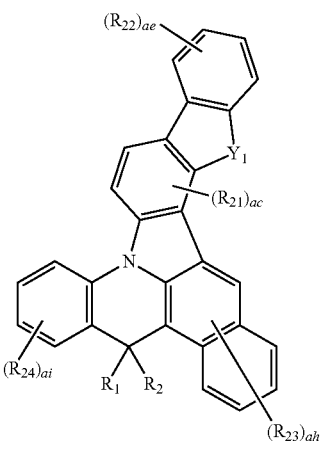

-continued

Formula 3-24
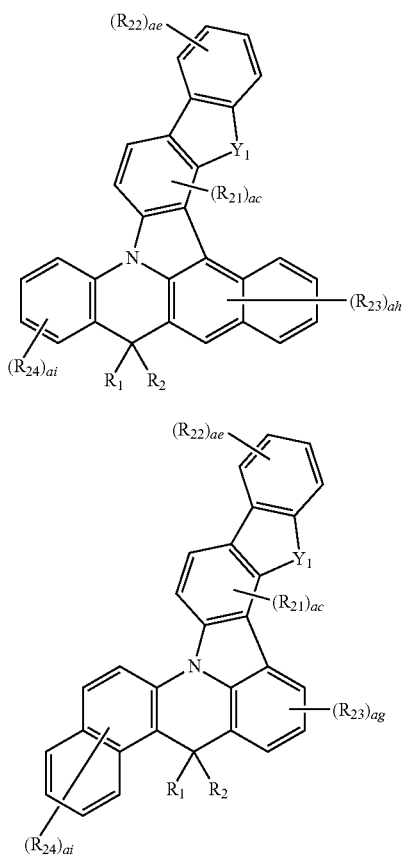

Formula 3-25
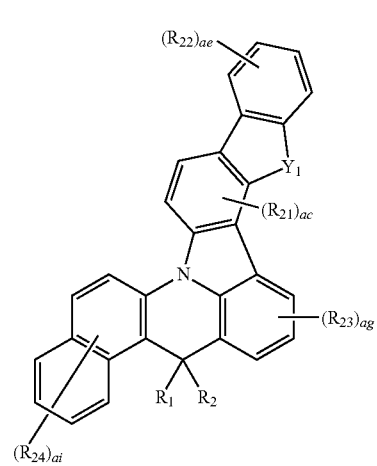

Formula 3-26
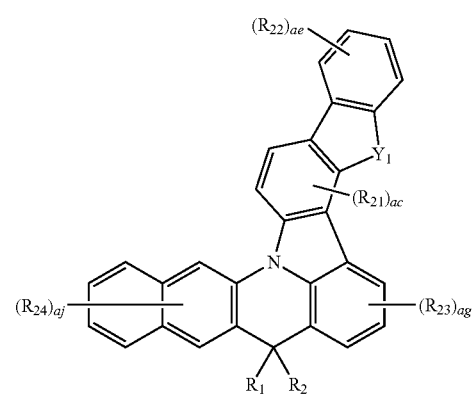

Formula 3-27
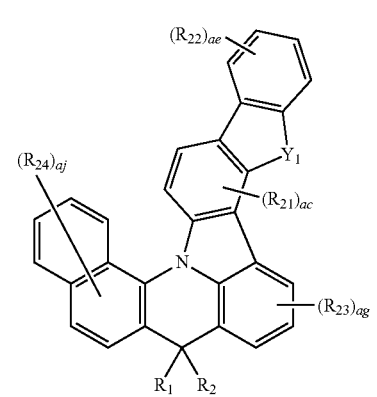

In Formulae 3-1 to 3-27, $R_1$, $R_2$, $R_{21}$ to $R_{24}$, $Y_1$, and ac to aj are defined as described above.

For example, in Formulae 3-1 to 3-27, $Y_1$ may be N-$(L_1)_{aa}$-$(R_{11})_{ab}$; and $R_{21}$ to $R_{24}$ may be hydrogen, but are not limited thereto.

Alternatively, for example, in Formulae 3-1 to 3-27, $Y_1$ may be S or O; $R_{21}$ to $R_{23}$ are hydrogen; ai and aj are 1; and $R_{24}$ may be -$(L_2)_{ao}$-$(R_{12})_{ap}$, but they are not limited thereto. $L_2$, ao, $R_{12}$, and ap are defined as described above.

According to an embodiment, the condensed-cyclic compound may be represented by any one of Formulae 4-1 to 4-19 below, but is not limited thereto.

Formula 4-1
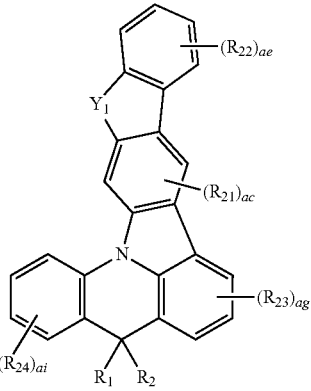

Formula 4-2
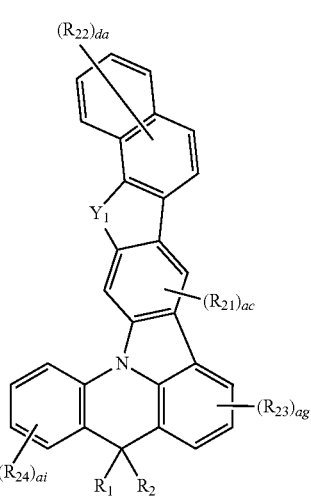

Formula 4-3
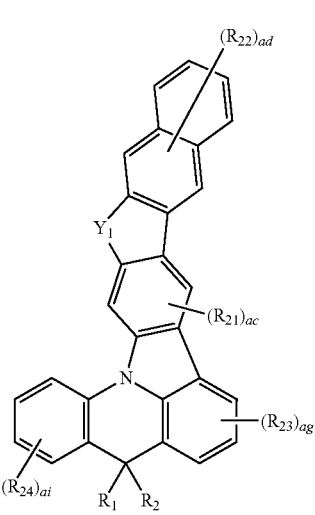

Formula 4-4
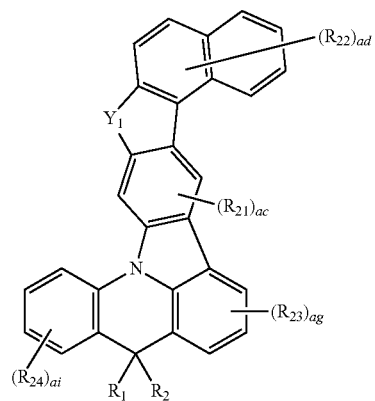
Formula 4-5
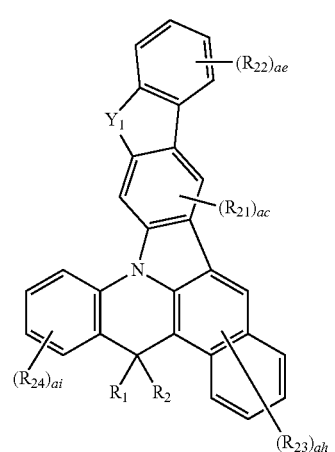
Formula 4-6
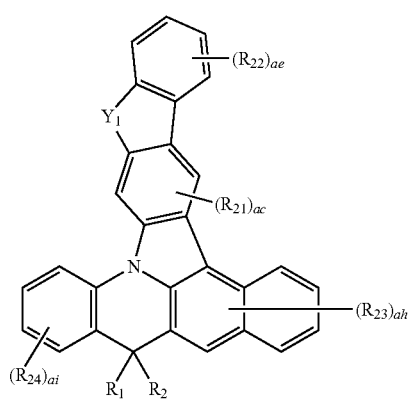
Formula 4-7
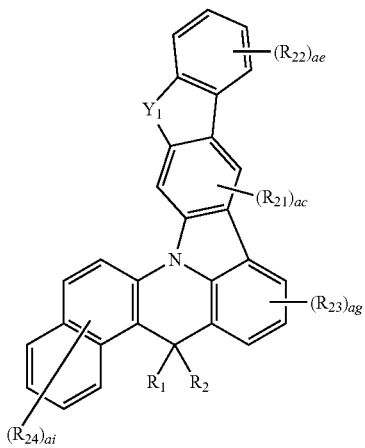
Formula 4-8
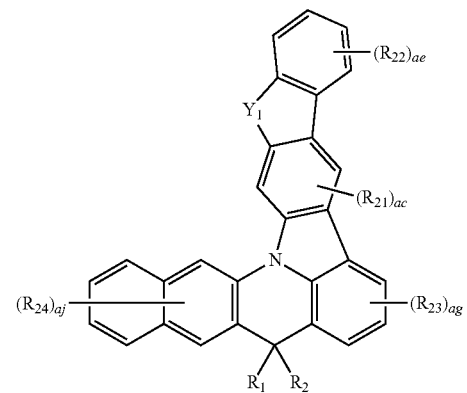
Formula 4-9
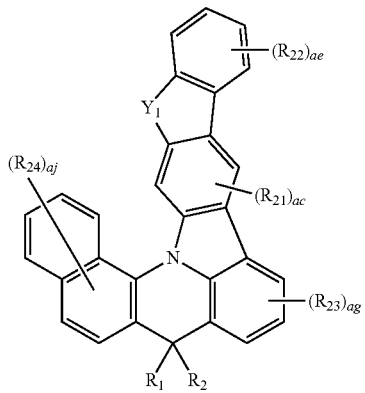
Formula 4-10
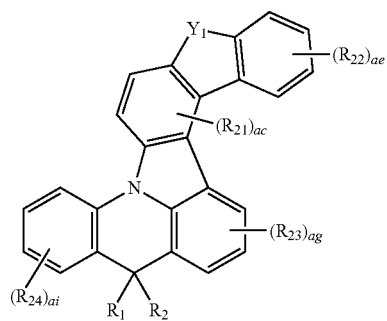

Formula 4-11
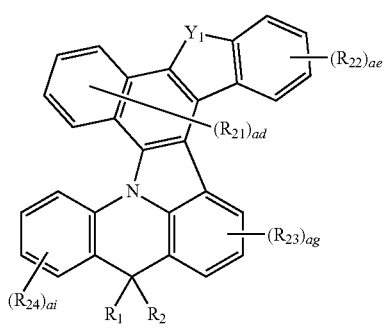
Formula 4-12
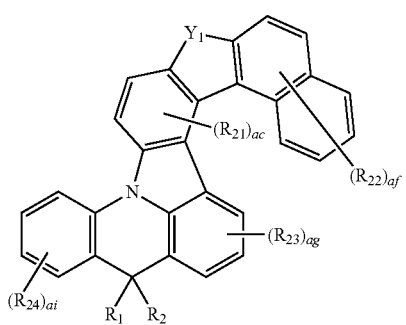
Formula 4-13
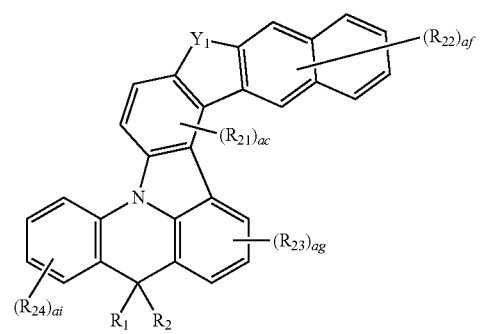
Formula 4-14
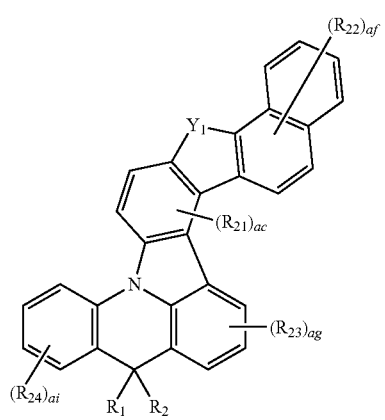
Formula 4-15
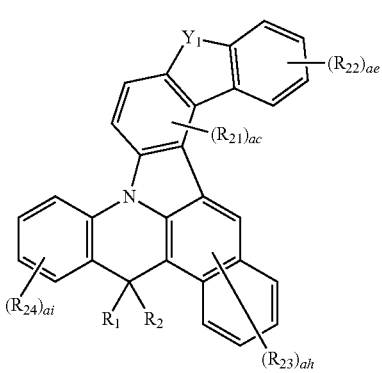
Formula 4-16
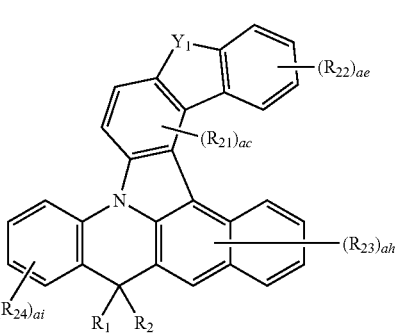
Formula 4-17
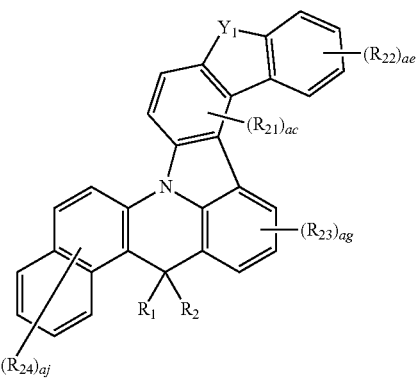
Formula 4-18
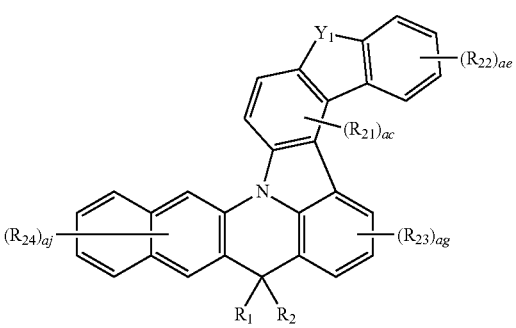

Formula 4-19

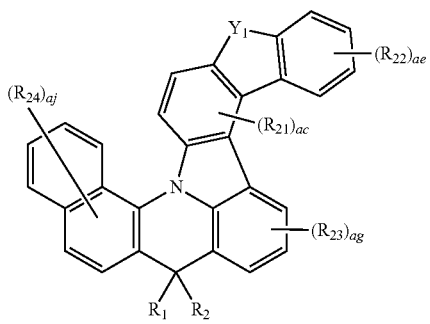

In Formulae 4-1 to 4-19, $R_1$, $R_2$, $R_{21}$ to $R_{24}$, $Y_1$, and ac to aj are defined as described above.

For example, in Formulae 3-1 to 3-27 and 4-1 to 4-19, $R_1$ and $R_2$ may be each independently selected from a substituted or unsubstituted $C_1$-$C_{10}$ alkyl group, a substituted or unsubstituted $C_1$-$C_{10}$ alkoxy group, and a substituted or unsubstituted $C_6$-$C_{14}$ aryl group; $R_{21}$ to $R_{24}$ may be each independently one of: hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a phenyl group, a naphthyl group, an anthryl group, a pyridinyl group, a pyrimidinyl group, a pyrazinyl group, and a triazinyl group; a phenyl group, a naphthyl group, an anthryl group, a pyridinyl group, a pyrimidinyl group, a pyrazinyl group, and a triazinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and -$(L_2)_{ao}$-$(R_{12})_{ap}$; $Y_1$ may be O, S, or N-$(L_1)_{aa}$-$(R_{11})_{ab}$; and ac to aj may be 1 or 2.

In this regard, $L_1$ may be one of a substituted or unsubstituted phenylene group, a substituted or unsubstituted naphthylene group, or a substituted or unsubstituted anthrylene group; aa may be 0, 1, or 2; $R_{11}$ may be one of: a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, and an isoquinolinyl group; and a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, and an isoquinolinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and ab may be 1 or 2.

For example, in Formulae 3-1 to 3-27 and 4-1 to 4-19, $R_1$ and $R_2$ may be each independently one of: a methyl group, an ethyl group, a propyl group, a butyl group, a pentyl group, a hexyl group, a heptyl group, an octyl group, a methoxy group, an ethoxy group, a propoxy group, a butoxy group, and a pentoxy group; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a phenyl group, a naphthyl group, and an anthryl group; and a phenyl group, a naphthyl group, and an anthryl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, and an anthryl group; $R_{21}$ to $R_{24}$ may be each independently hydrogen; $Y_1$ may be O, S, or N-$(L_1)_{aa}$-$(R_{11})_{ab}$; and ac to aj may be 1 or 2. For example, $L_1$ may be selected from a substituted or unsubstituted phenylene group, a substituted or unsubstituted naphthylene group, and a substituted or unsubstituted anthrylene group; aa may be 0, 1, or 2; $R_{11}$ may be represented by Formula 9; and ab may be 1 or 2.

For example, the condensed-cyclic compound may be represented by any one of Formulae 3-1, 3-3, 3-6, 3-8, and 3-9, $Y_1$ may be N-$(L_1)_{aa}$-$(R_{11})_{ab}$; $L_1$ may be selected from a substituted or unsubstituted phenylene group, a substituted or unsubstituted naphtylene group, a substituted or unsubstituted fluorenylene group, a substituted or unsubstituted spirofluorenylene group, a substituted or unsubstituted anthrylene group, a substituted or unsubstituted fluoranthenylene group, a substituted or unsubstituted triphenylenylene group, and a substituted or unsubstituted pyrenylene; aa may be 0, 1, or 2; $R_{11}$ may be represented by Formula 9; ab may be 1 or 2; and $R_1$ and $R_2$ are each independently selected from a methyl group, an ethyl group, a propyl group, a butyl group, a pentyl group, a phenyl group, a naphthyl group, and an anthryl group, but they are not limited thereto.

According to an embodiment, the condensed-cyclic compound may be any one of Compounds 1 to 13 below, but is not limited thereto.

1

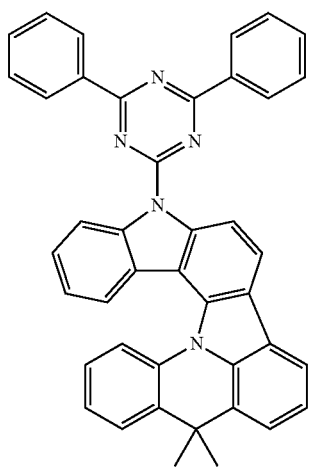

-continued
2
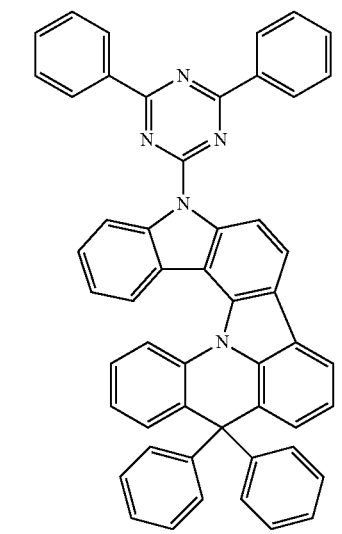
3
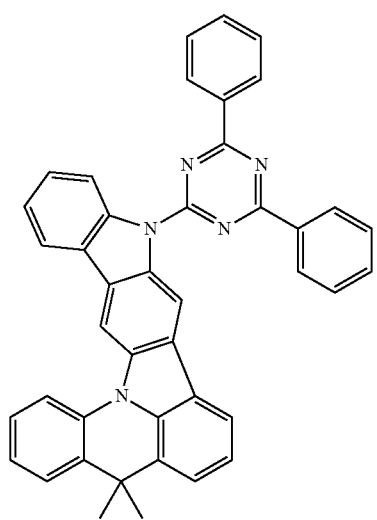
4
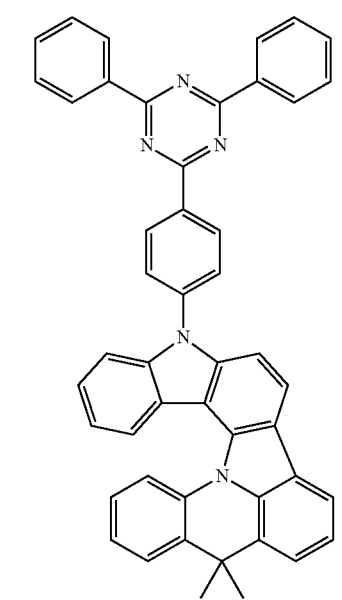
-continued
5
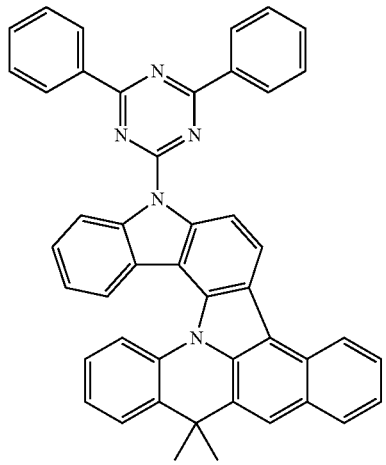
6
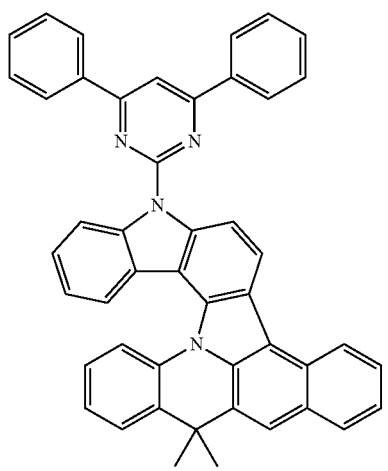
7
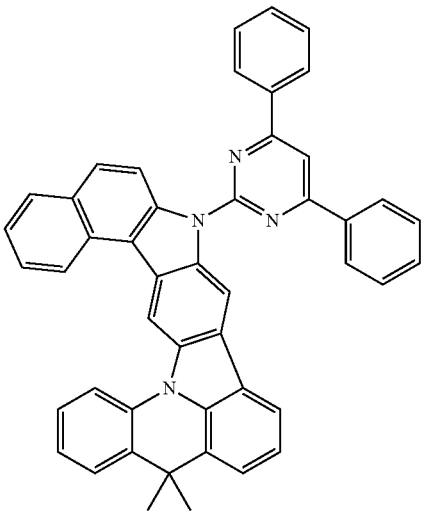

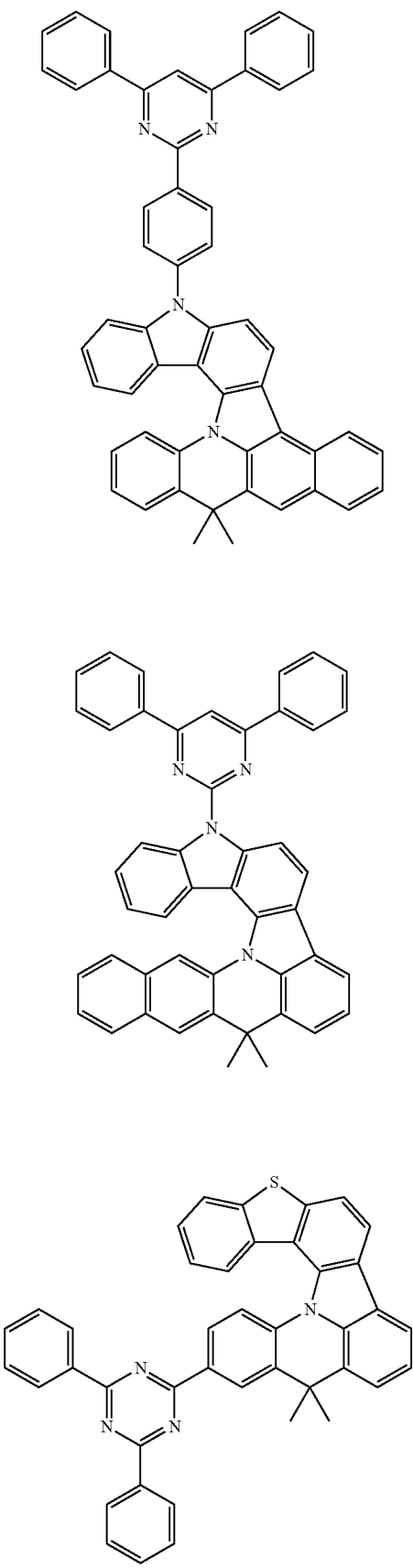
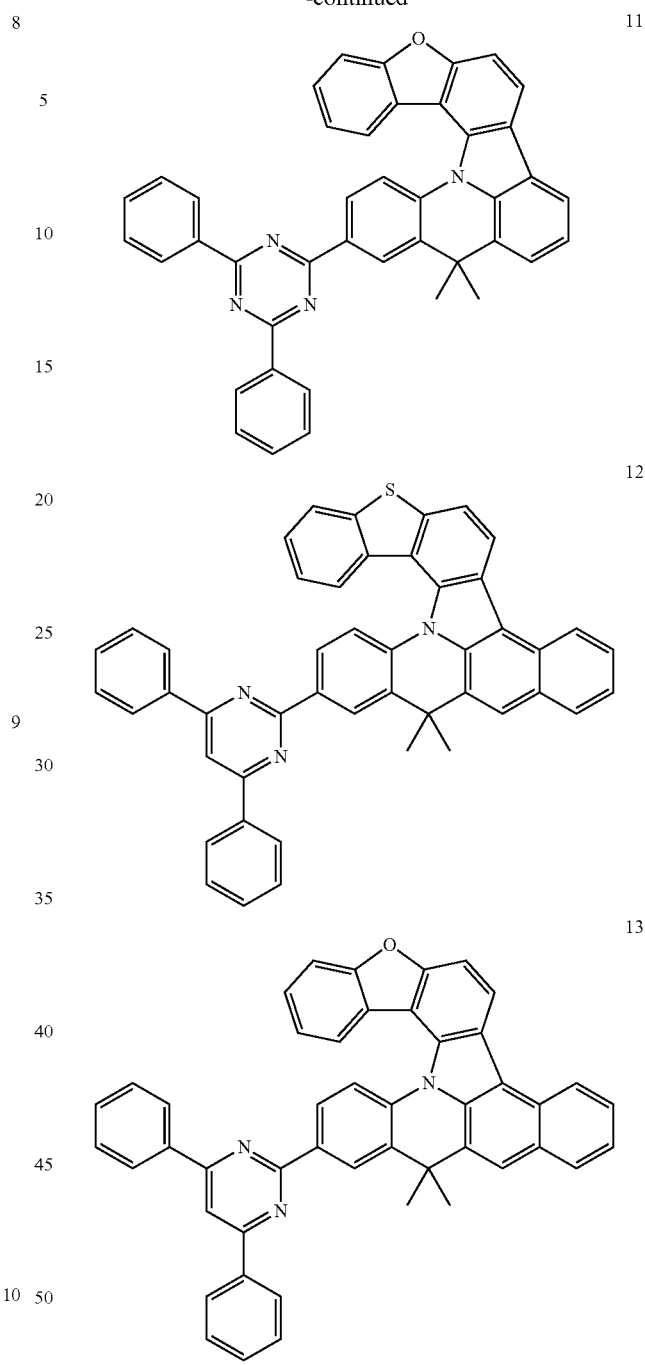

Since $Y_1$ of Formula 2, which may be the ring $A_2$ of the condensed-cyclic compound represented by Formula 1, may be O, S, or $N\text{-}(L_1)_{aa}\text{-}(R_{11})_{ab}$, the condensed-cyclic compound of Formula 1 may improve hole mobility and electron mobility in a balanced way. Thus, the condensed-cyclic compound may be efficiently used as a light-emitting material, particularly, a phosphorescent host material, of an organic light-emitting diode.

In addition, in the condensed-cyclic compound of Formula 1, $R_1$ and $R_2$ are not linked to each other. The condensed-cyclic compound of Formula 1 is easily synthesized and has a molecular weight suitable for deposition. Because the compound of Formula 1 has thermal resistance, an organic light-emitting diode including the same may have a long lifespan.

The organic light-emitting diode including the condensed-cyclic compound may have low driving voltage, high efficiency, high brightness and long lifespan.

The condensed-cyclic compound represented by Formula 1 may be synthesized using known organic synthesis methods. The method of synthesizing the condensed-cyclic compound will be obvious to one or ordinary skill in the art with reference to examples that will be described later.

The condensed-cyclic compound of Formula 1 may be interposed between a pair of electrodes of an organic light-emitting diode. For example, the condensed-cyclic compound may be used in an emission layer (EML).

According to another embodiment of the present invention, there is provided an organic light-emitting diode including a first electrode, a second electrode disposed opposite to the first electrode, and an organic layer interposed between the first electrode and the second electrode, the organic layer including at least one condensed-cyclic compound represented by Formula 1 as described above.

The phrase "(the organic layer) includes at least one condensed-cyclic compound" used herein may be interpreted as "(the organic layer) includes one condensed-cyclic compound represented by Formula 1, or at least two different condensed-cyclic compounds represented by Formula 1".

For example, the organic layer may include Compound 1 alone as the condensed-cyclic compound. In this regard, Compound 1 may be present in the EML of the organic light-emitting diode. Alternatively, the organic layer may include Compound 1 and Compound 2 as the condensed-cyclic compounds. In this regard, Compound 1 and Compound 2 may be disposed in the same layer (for example, Compound 1 and Compound 2 may be disposed in the EML), or in different layers (for example, Compound 1 may be disposed in the EML and Compound 2 may be disposed in the electron transport layer (ETL)).

The organic layer may include at least one layer selected from the group consisting of a hole injection layer (HIL), a hole transport layer (HTL), a functional layer having both hole injecting and hole transporting capabilities (H-functional layer), a buffer layer, an electron blocking layer (EBL), an EML, a hole blocking layer (HBL), an ETL, an electron injection layer (EIL), and a functional layer having both electron injecting and electron transporting capabilities (E-functional layer).

The term "organic layer" used herein refers to a single layer and/or multiple layers interposed between the first and second electrodes of the organic light-emitting diode.

The organic layer may include an EML that includes the condensed-cyclic compound.

The condensed-cyclic compound contained in the EML may be used as a host, for example, a phosphorescent host. In this regard, the EML may further include a dopant. The dopant may be a phosphorescent dopant. For example, the phosphorescent dopant may be an organometallic compound comprising a metal selected from Ir, Pt, Os, Ti, Zr, Hf, Eu, Tb, and Tm.

FIG. 1 is a schematic sectional view of an organic light-emitting diode 10 according to an embodiment of the present invention. Hereinafter, the organic light-emitting diode 10 and a method of fabricating the organic light-emitting diode 10 will be described with reference to FIG. 1.

A substrate 11, which may be any substrate that is commonly used in organic light-emitting diodes, may be a glass substrate or a transparent plastic substrate with excellent mechanical strength, thermal stability, transparency, surface smoothness, ease of handling, and waterproofness.

A first electrode 13 may be formed on the substrate 11 by depositing or sputtering a material that is used to form the first electrode 13. When the first electrode 13 constitutes an anode, the material used to form the first electrode 13 may be a high work function material so as to facilitate hole injection. The first electrode 13 may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using one of magnesium (Mg), aluminum (Al), aluminum-lithium (Al—Li), calcium (Ca), magnesium-indium (Mg—In), magnesium-silver (Mg—Ag), and the like.

The first electrode 13 may have a single-layered or a multi-layered structure. For example, the first electrode 13 may have a triple-layered structure of ITO/Ag/ITO, but is not limited thereto.

The organic emission layer 15 is formed on the first electrode 13.

The organic layer 15 may include an HIL, an HTL, a buffer layer, an EML, an ETL, and an EIL.

The HIL may be formed on the first electrode 13 by vacuum deposition, spin coating, casting, Langmuir-Blodgett (LB) deposition, or the like.

When the HIL is formed using vacuum deposition, the deposition conditions may vary depending upon the compound that is used to form the HIL and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of about 0.01 to about 100 Å/sec, but are not limited thereto.

When the HIL is formed using spin coating, coating conditions may vary depending upon the compound that is used to form the HIL and the structure and thermal characteristics of the HIL to be formed. For example, the coating conditions may include a coating speed of about 2000 rpm to about 5000 rpm and a thermal treatment temperature of about 80° C. to about 200° C., the thermal treatment having the purpose of removing a solvent after coating. However, the coating conditions are not limited thereto.

Any known hole injecting materials may be used to form the HIL, and examples of known hole injecting materials may be N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and (polyaniline)/poly(4-styrene-sulfonate) (PANI/PSS), but are not limited thereto.

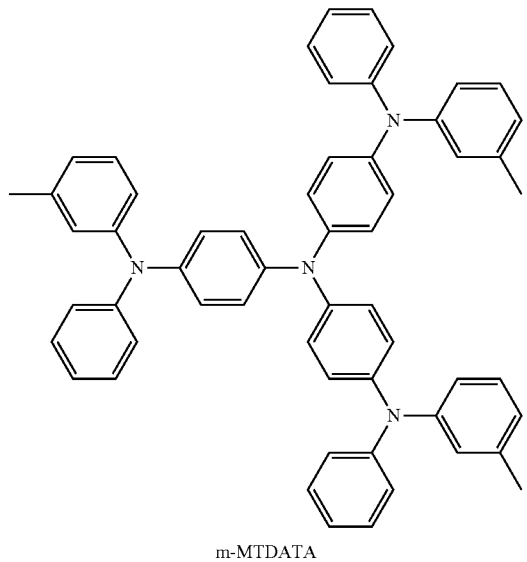

m-MTDATA

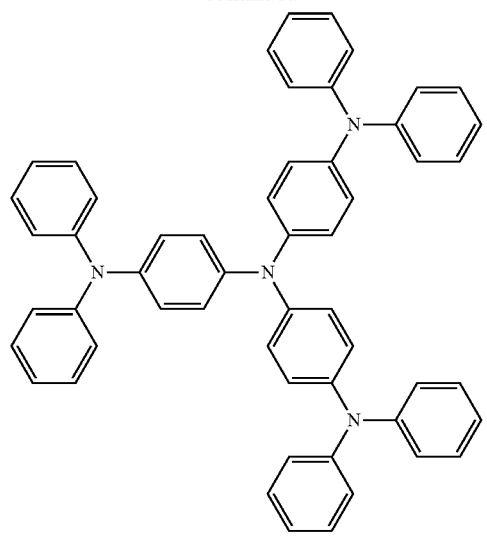

TDATA

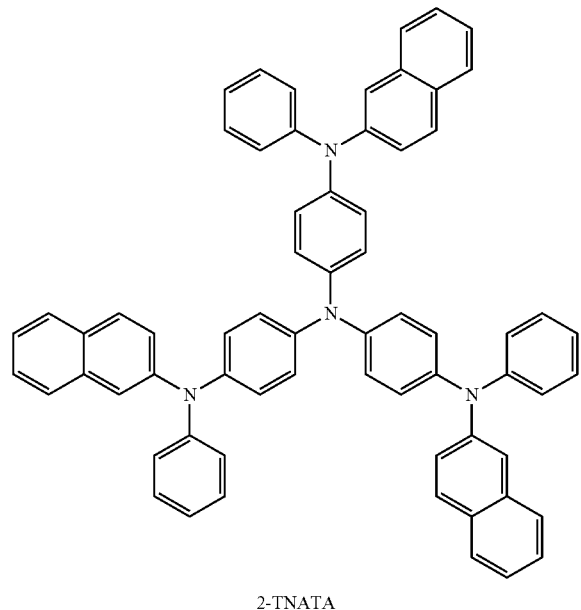

2-TNATA

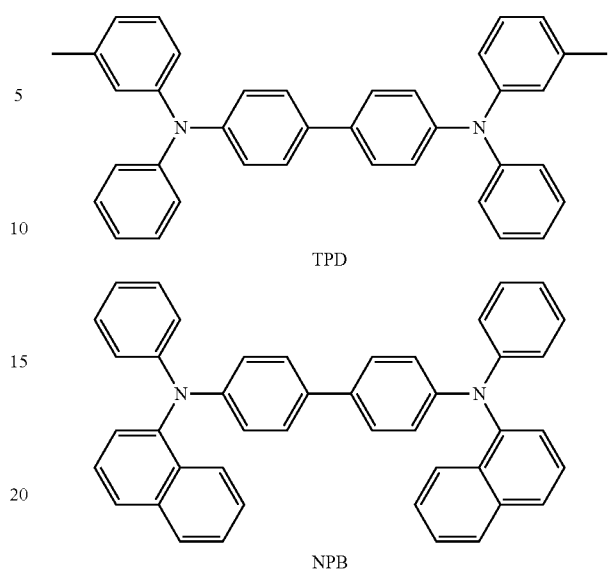

TPD

NPB

The thickness of the HTL may be in a range of about 50 to about 2,000 Å or, for example, about 100 to about 1,500 Å. When the thickness of the HTL is within this range, the HTL may have excellent hole transporting ability without a substantial increase in driving voltage.

The H-functional layer may include at least one of the hole injecting materials and hole transporting materials as described above, and the thickness of the H-functional layer may be in the range of about 500 Å to about 10,000 Å, or for example, about 100 Å to about 1,000 Å. When the thickness of the H-functional layer is within this range, the H-functional layer may have excellent hole injecting and transporting abilities without a substantial increase in driving voltage.

Meanwhile, at least one of the HIL, HTL, and the H-functional layer may include at least one of the compounds represented by Formulae 300 and 350 below.

The thickness of the HIL may be about 100 to about 10,000 Å, and for example, about 100 to about 1,000 Å. When the thickness of the HIL is within this range, the HIL may have excellent hole injecting ability without a substantial increase in driving voltage.

Then, the HTL may be formed on the HIL by using vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used to form the HTL.

Examples of the known hole transporting material include carbazole derivatives such as N-phenylcarbazole and polyvinyl carbazole, N,N-bis(3-methylphenyl)-N,N-diphenyl-[1,1-biphenyl]-4,4'-diamine (TPD), 4,4',4"-tris (N-carbazolyl) triphenylamine (TCTA), and N,N'-di(1-naphthyl)-N,N'-diphenylbenzidine (NPB), but are not limited thereto.

Formula 300

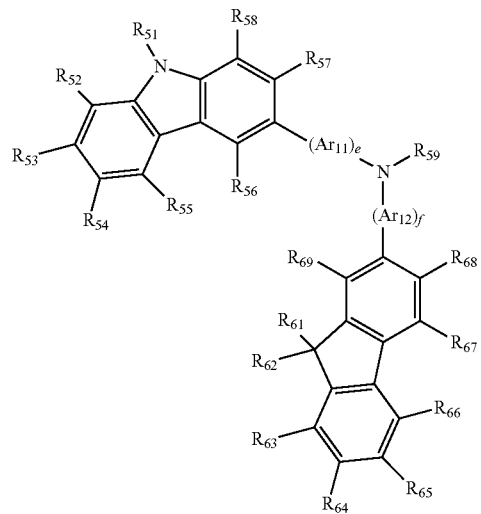

Formula 350

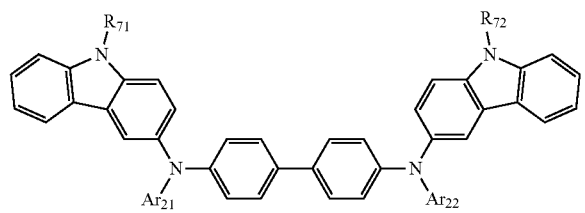

In Formulae 300 and 350, $Ar_{11}$ and $Ar_{12}$ may be each independently a substituted or unsubstituted $C_5$-$C_{60}$ arylene group, and $Ar_{21}$ and $Ar_{22}$ may be a substituted or unsubstituted $C_5$-$C_{60}$ aryl group. $Ar_{11}$ and $Ar_{12}$ are defined as described above with reference to $L_1$. $Ar_{21}$ and $Ar_{22}$ are defined as described above with reference to $R_{11}$.

In Formula 300, e and f are each independently an integer from 0 to 5, or 0, 1, or 2. For example, e may be 1, and f may be 0, but they are not limited thereto.

In Formulae 300 and 350, $R_{51}$ to $R_{58}$, $R_{61}$ to $R_{69}$, $R_{71}$, and $R_{72}$ may be each independently selected from hydrogen, deuterium, a halogen atom, a hydroxyl group, a cyano group, a nitro group, an amino group, an amidino group, hydrazine, hydrazone, a carboxyl group or salts thereof, a sulfonic acid group or salts thereof, a phosphoric acid or salts thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. For example, $R_{51}$ to $R_{58}$, $R_{61}$ to $R_{69}$, $R_{71}$, and $R_{72}$ may be each independently one of: hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, and a hexyl group); a $C_1$-$C_{10}$ alkoxy group (e.g., a methoxy group, an ethoxy group, a propoxy group, a butoxy group, and a pentoxy group); a $C_1$-$C_{10}$ alkyl group and a $C_1$-$C_{10}$ alkoxy group substituted with at least one selected from the group consisting of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group substituted with at least one selected from the group consisting of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group, but are not limited thereto.

In Formula 300, $R_{59}$ may be one of: a phenyl group; a naphthyl group; an anthryl group; a biphenyl group; a pyridyl group; and a phenyl group, a naphthyl group, an anthryl group, a biphenyl group, and a pyridyl group substituted with at least one selected from the group consisting of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

According to an embodiment of the present invention, the compound of Formula 300 may be represented by Formula 300A below, but is not limited thereto.

Formula 300A

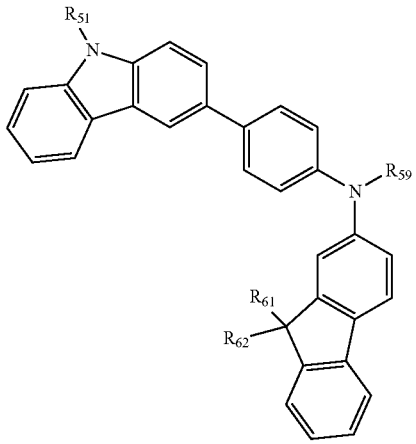

In Formula 300A, $R_{51}$, $R_{60}$, $R_{61}$ and $R_{59}$ are defined as described above.

For example, at least one of the HIL, the HTL, and the H-functional layer may include at least one of Compounds 301 to 320 below, but is not limited thereto.

301

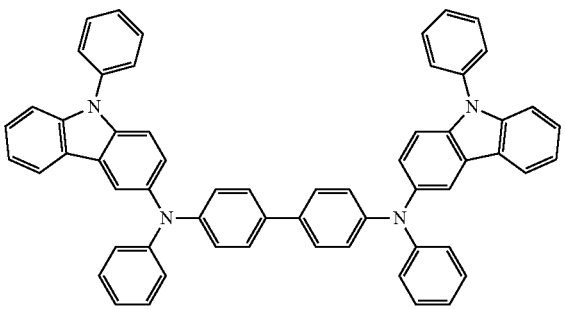

302

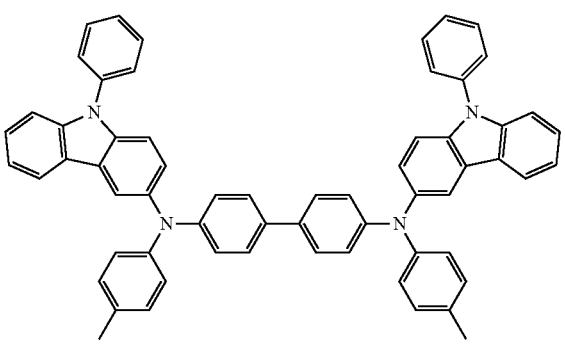

303
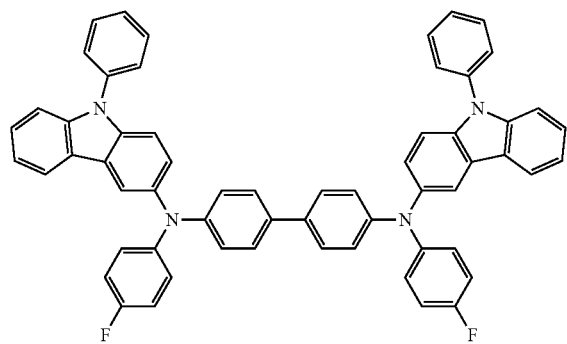
304
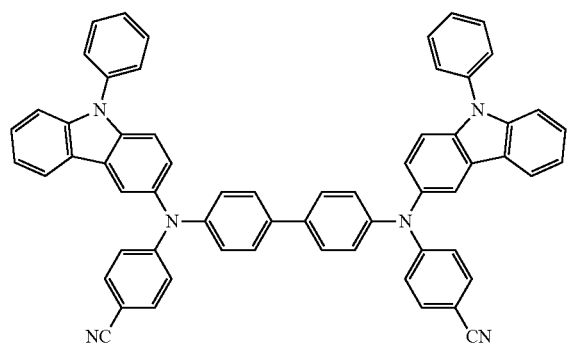
305
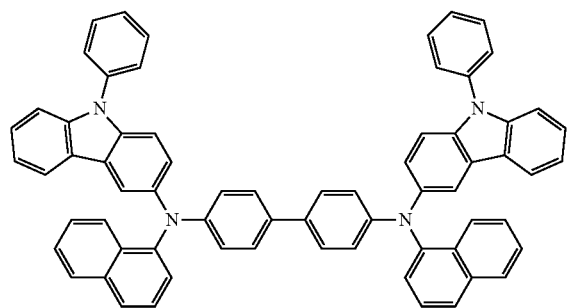
306
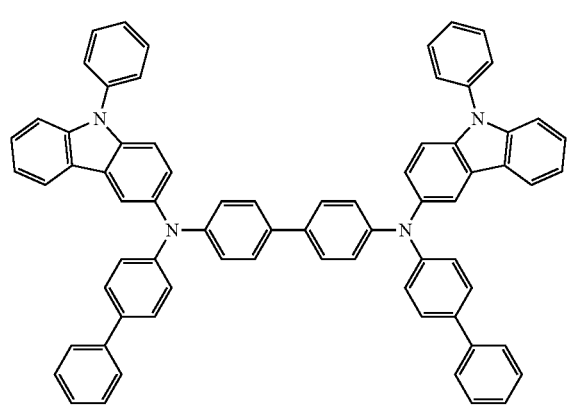
307
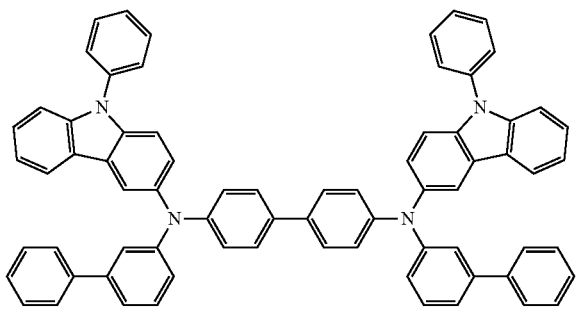
308
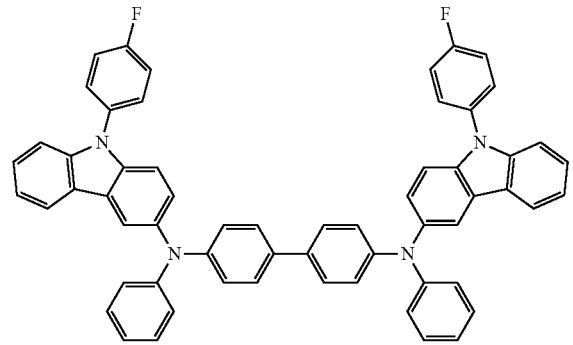
309
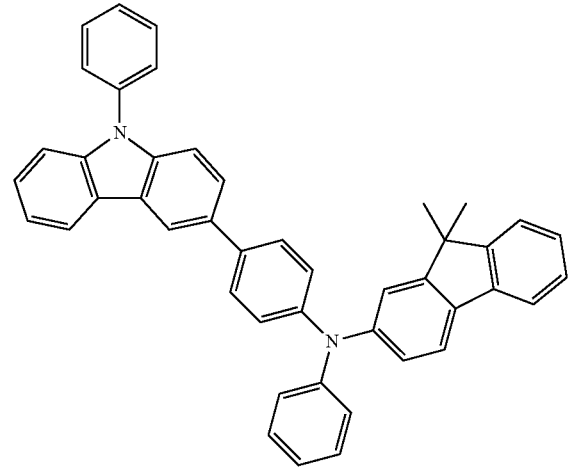

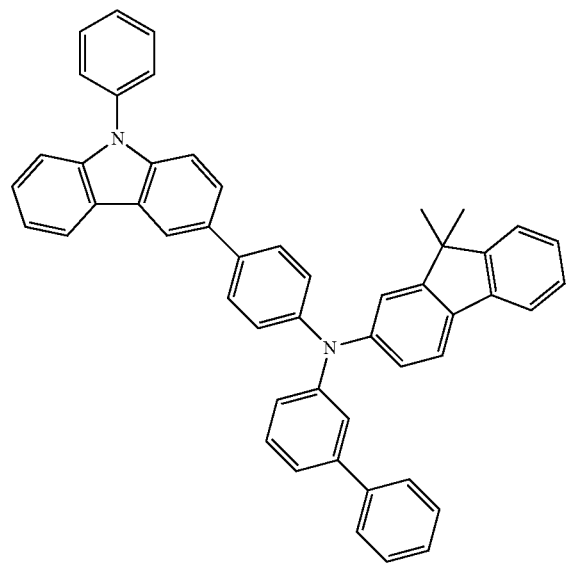
310
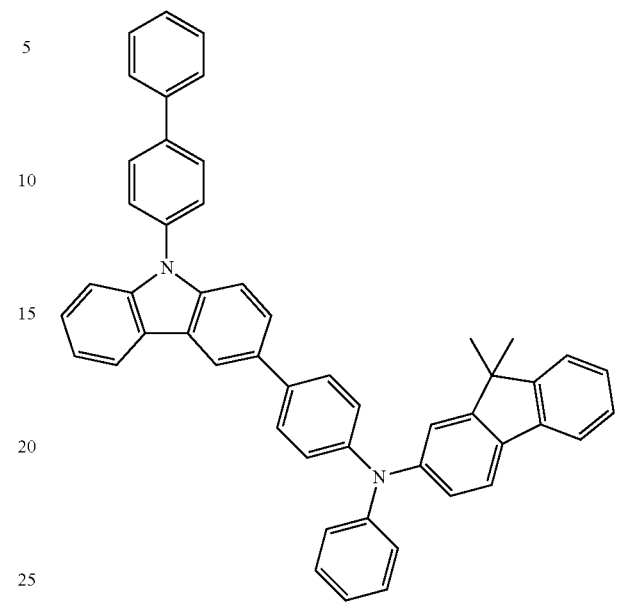
312
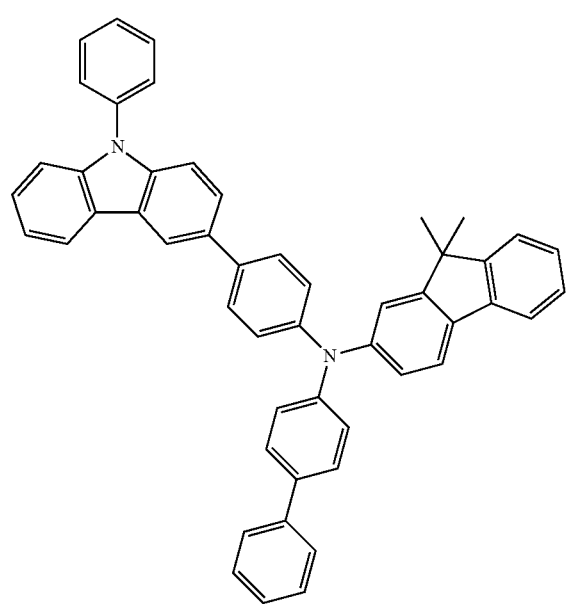
311
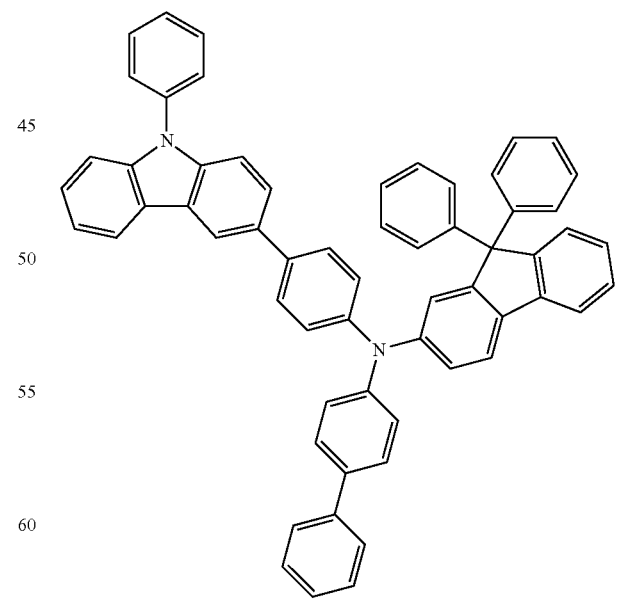
313

314
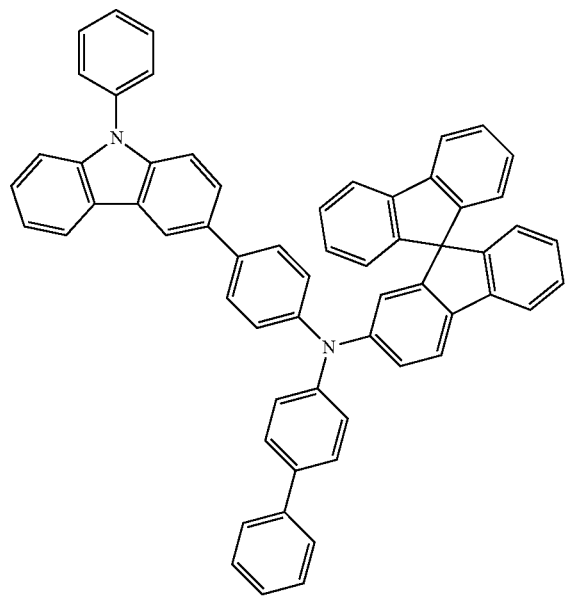
316
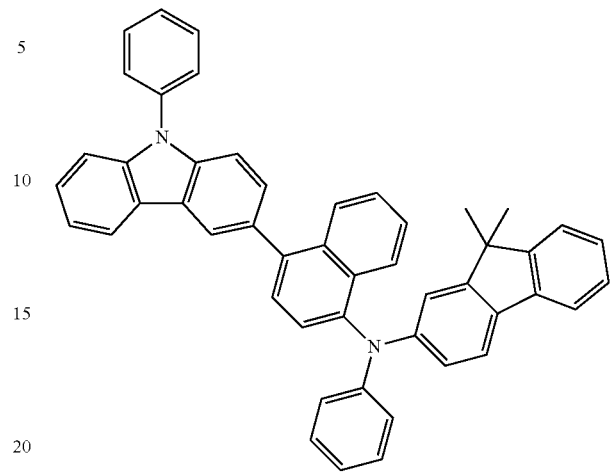
317
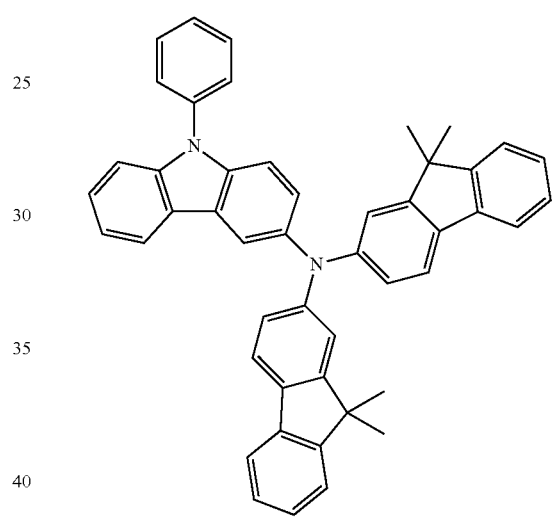
315
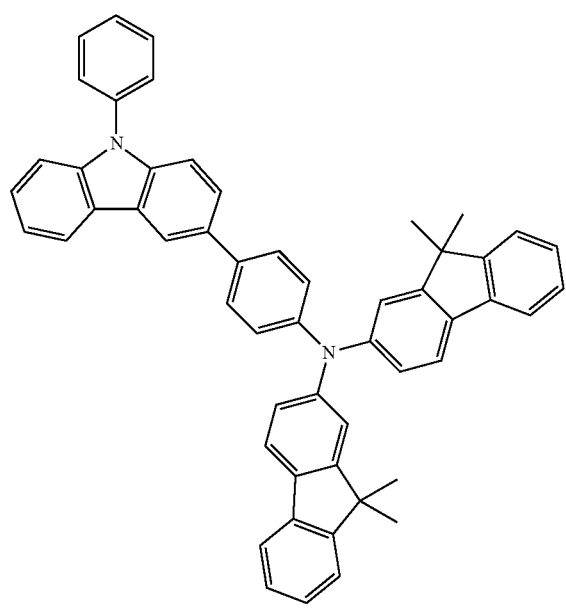
318
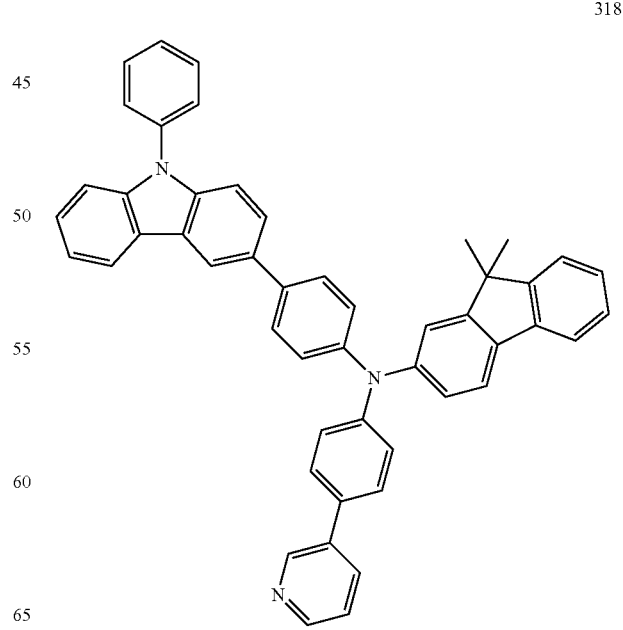

319

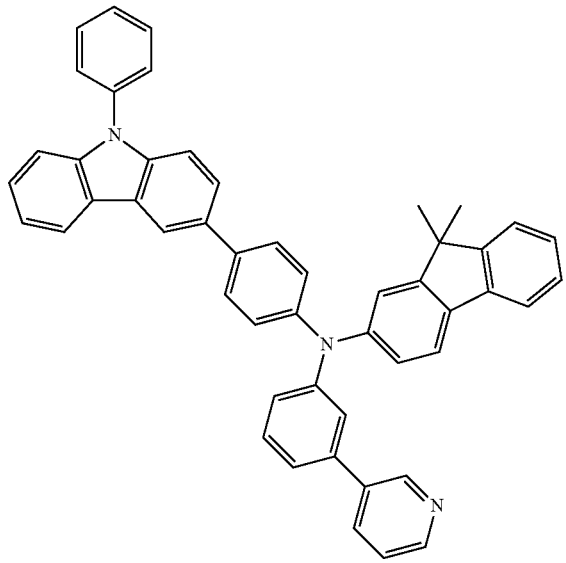

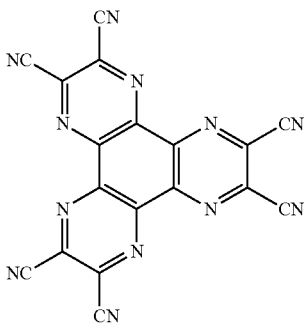
Compound 200

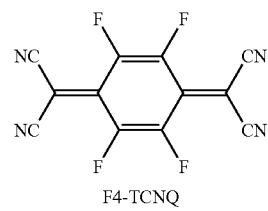
F4-TCNQ

320

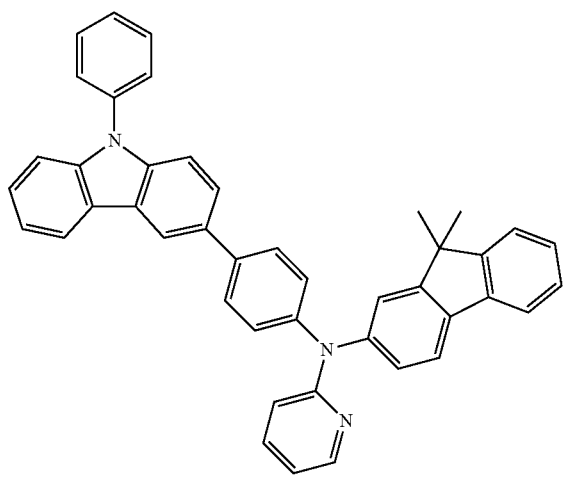

At least one of the HIL, the HTL, and the H-functional layer may further include a charge-generating material in addition to known hole injecting materials, known hole transporting materials, and/or materials having both hole injecting and hole transporting capabilities in order to improve conductivity of the layer.

The charge-generating material may be a p-dopant. The p-dopant may be a quinone derivative, a metal oxide, or a cyano group-containing compound, but is not limited thereto. Examples of the p-dopant include a quinine derivative such as tetracyanoquinonedimethane (TCNQ) and 2,3,5,6-tetrafluoro-tetracyano-1,4-benzoquinonedimethane (F4TCNQ); a metal oxide such as tungsten oxide and molybdenum oxide; and a cyano group-containing compound such as Compound 200 below, but are not limited thereto.

If the HIL, the HTL, or the H-functional layer further includes the charge-generating material, the charge-generating material may be homogeneously or non-homogeneously dispersed in the HIL, the HTL, or the H-functional layer, or a variety of modifications may be possible.

A buffer layer may be interposed between the EML and at least one of the HIL, the HTL, and the H-functional layer. The buffer layer may increase efficiency by compensating an optical resonant distance according to a wavelength of light emitted from the EML. The buffer layer may include known hole injecting materials and known hole transporting materials. The buffer layer may also include a material that is the same as one of the materials contained in the HIL, the HTL, and the H-functional layer disposed under the buffer layer.

The EML may be formed on the HTL, the H-functional layer, or the buffer layer by vacuum deposition, spin coating, casting, LB deposition, or the like. When the EML is formed by using vacuum deposition or spin coating, the deposition and coating conditions may be similar to those used to form the HIL, although the deposition and coating conditions may vary according to a compound that is used to form the EML.

The EML may include a host and a dopant.

As the host, the condensed-cyclic compound represented by Formula 1 as described above may be used.

If the organic light-emitting diode is a full-color organic light-emitting diode, the EML may be patterned to a red EML, a green EML, and a blue EML. Alternatively, the EML may have a structure in which a red EML, a green EML, and/or a blue EML are deposited and may emit a white light.

Meanwhile, at least one of the red, green, and blue EMLs may include the following dopant (ppy=phenylpyridine).

For example, the following compounds may be used as a blue dopant, but it is not limited thereto.

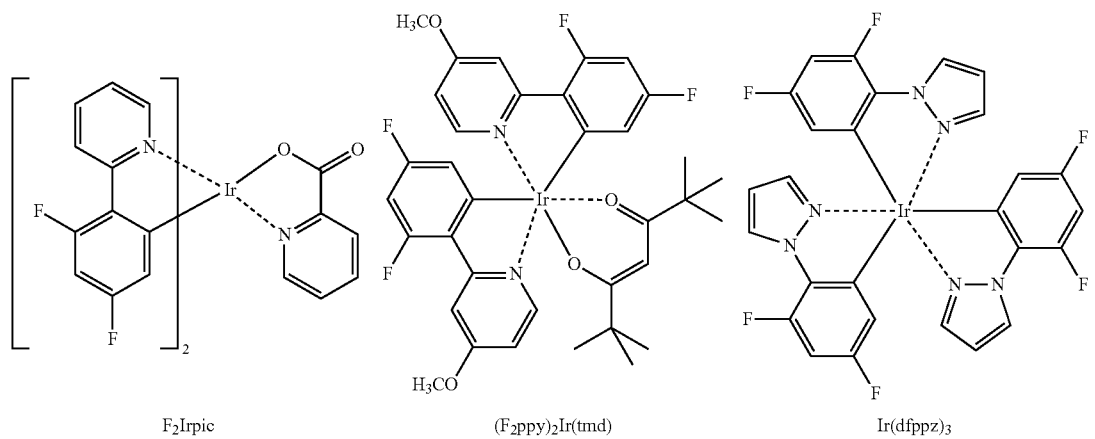
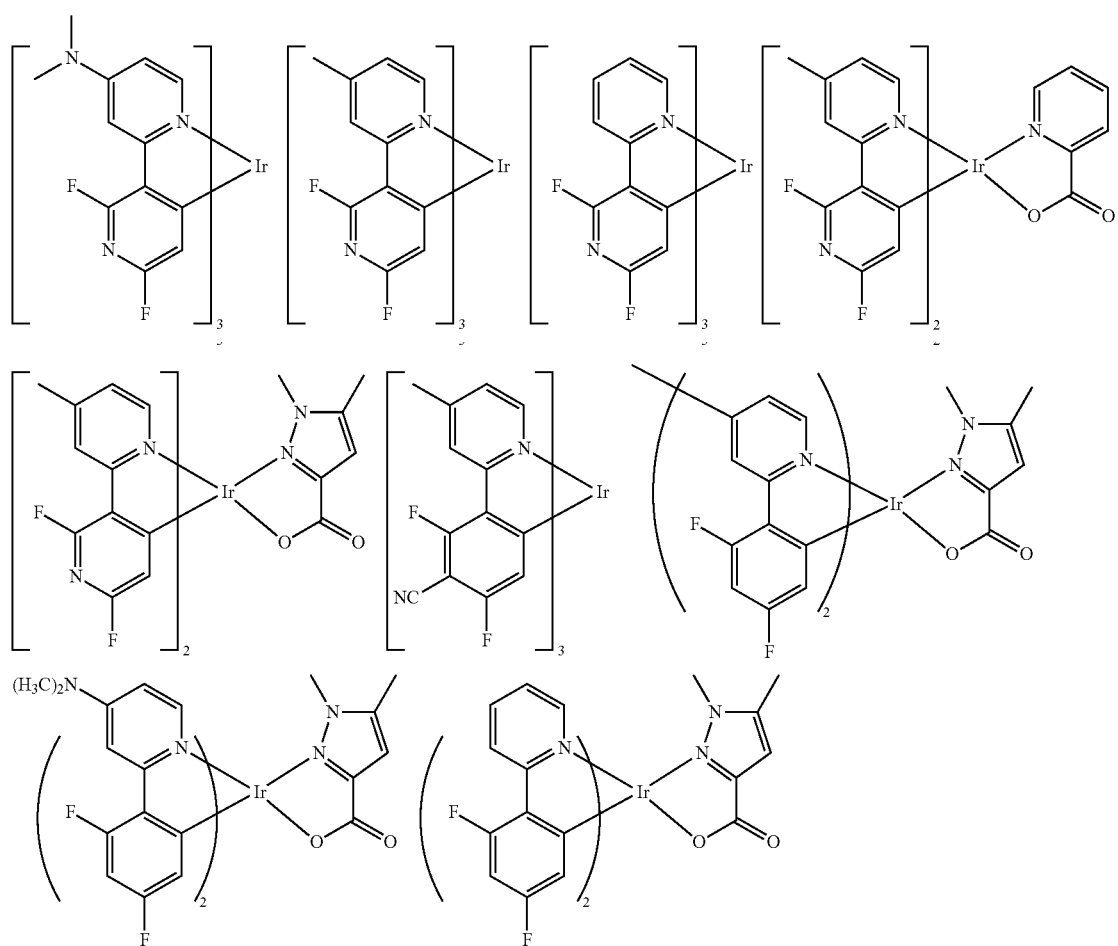
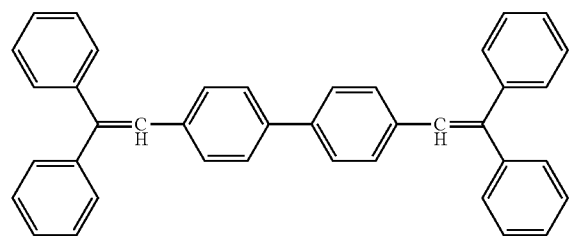

-continued
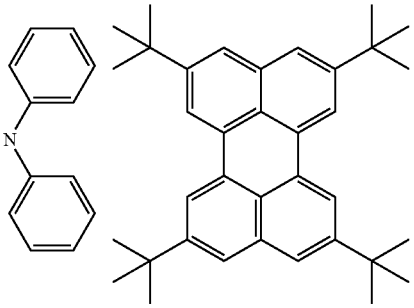
DPAVBi
TBPe
For example, the following compounds may be used as a red dopant, but useful red dopants are not limited thereto. Alternatively, DCM or DCJTB, which will be described later, may be used as a red dopant.
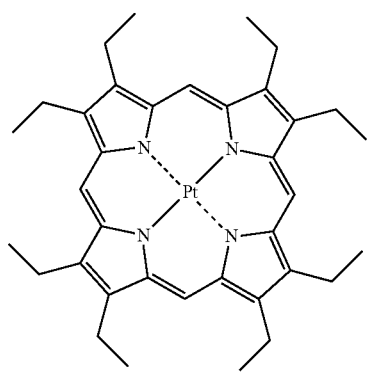
PtOEP
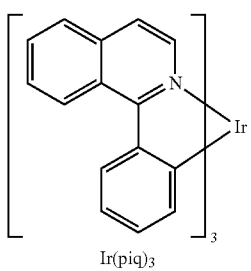
Ir(piq)₃
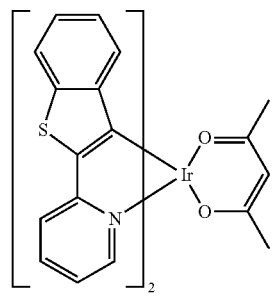
Btp₂Ir(acac)
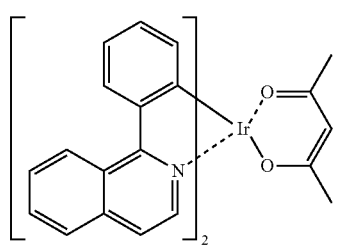
-continued
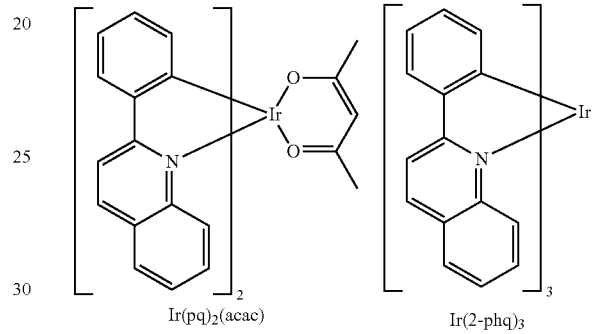
Ir(pq)₂(acac)  Ir(2-phq)₃
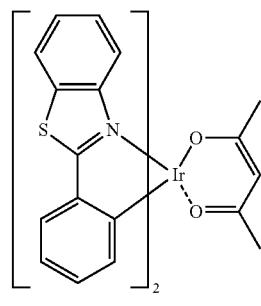
Ir(BT)₂(acac)
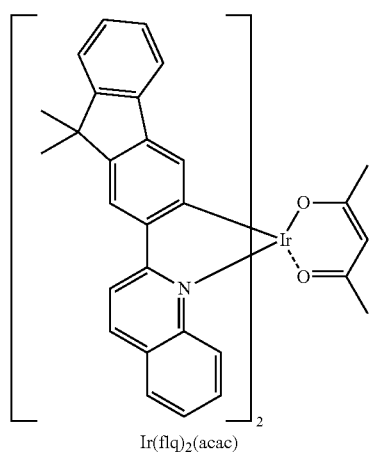
Ir(flq)₂(acac)

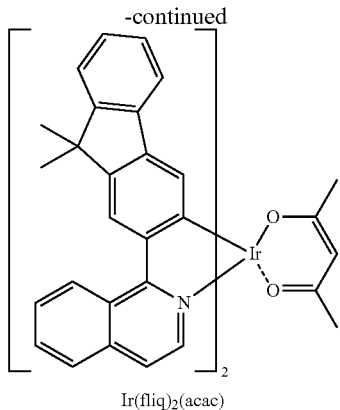
Ir(fliq)₂(acac)
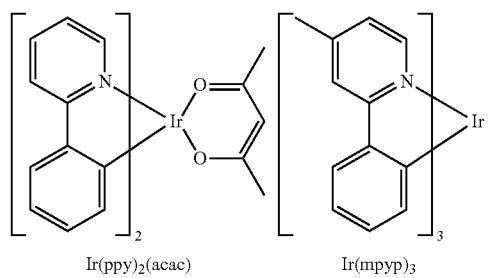
Ir(ppy)₂(acac)  Ir(mpyp)₃
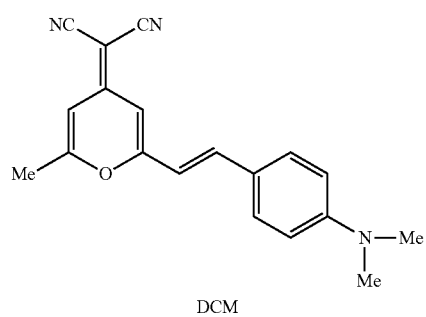
DCM
C545T
Meanwhile, the dopant used in the EML may be a Pt-complex, which will be described later, but is not limited thereto.
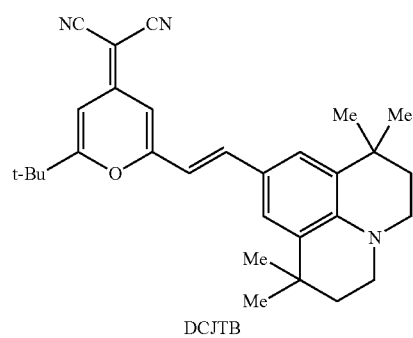
DCJTB
For example, the following compounds may be used as green dopants, but useful green dopants are not limited thereto. Alternatively, C545T below may be used as a green dopant.
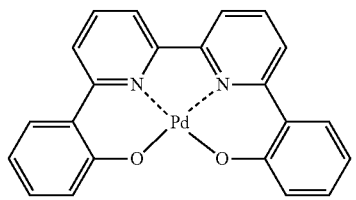
D1
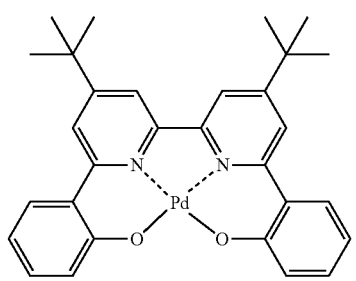
D2
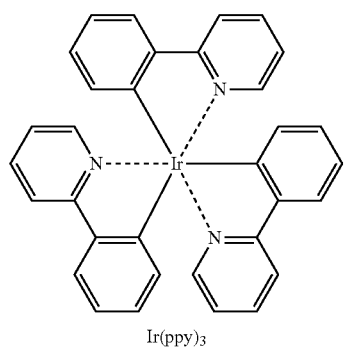
Ir(ppy)₃
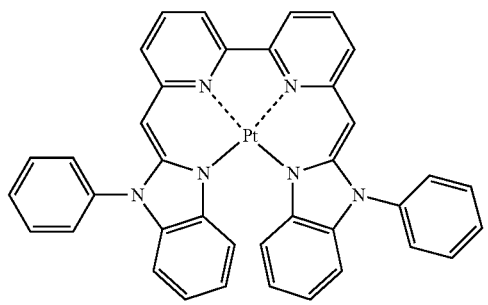
D3

D4
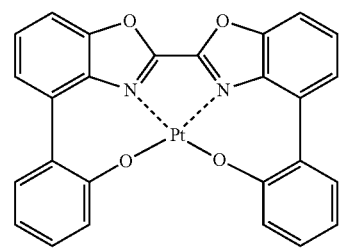
D5
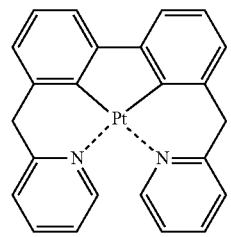
D6
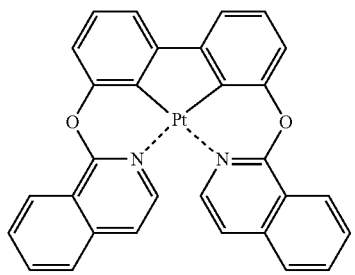
D7
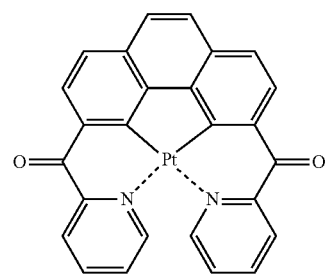
D8
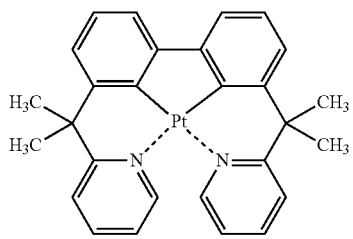
D9
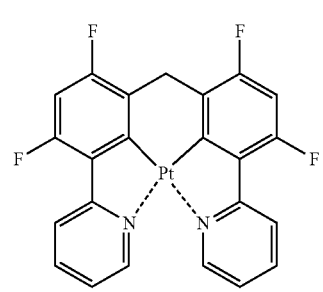
D10
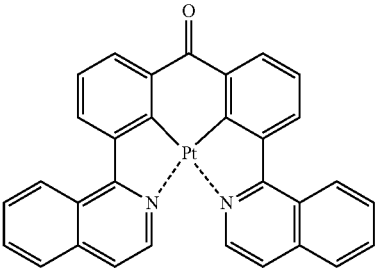
D11
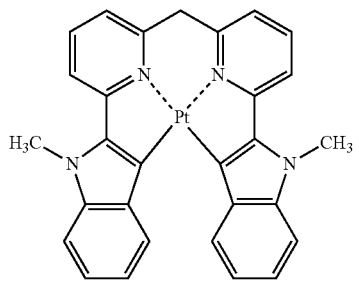
D12
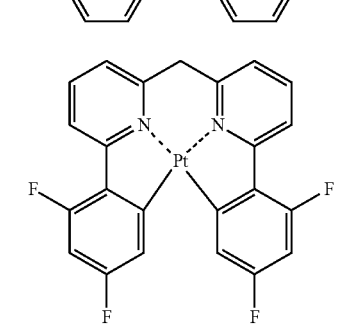
D13
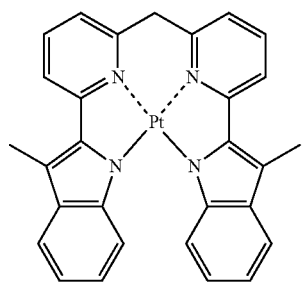
D14
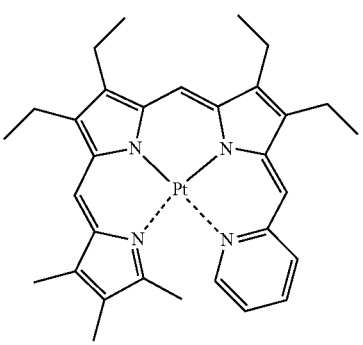

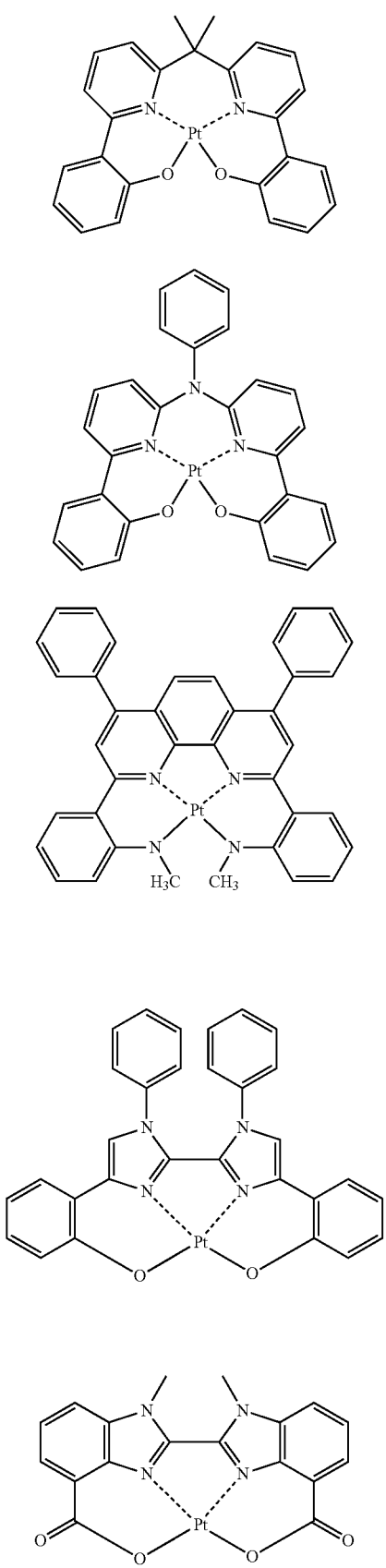

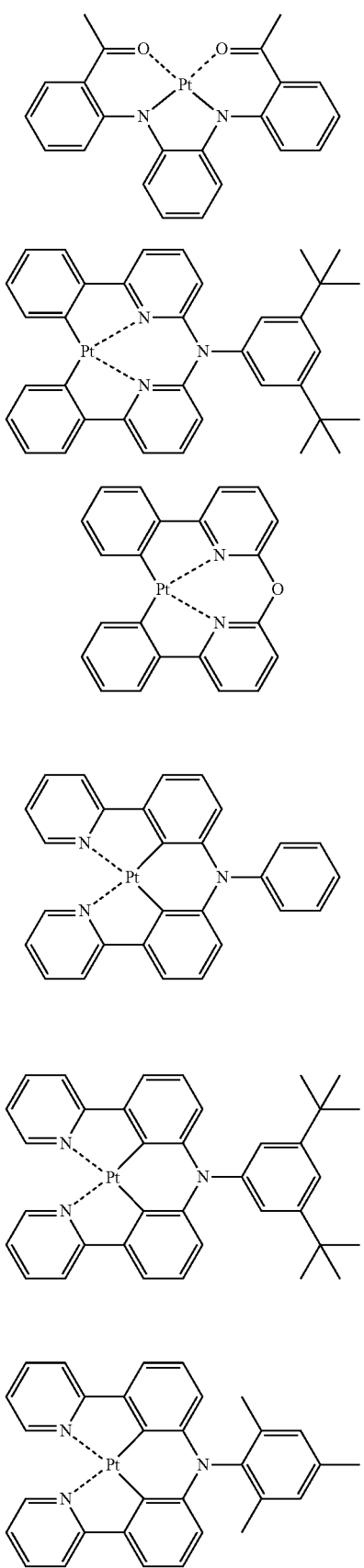
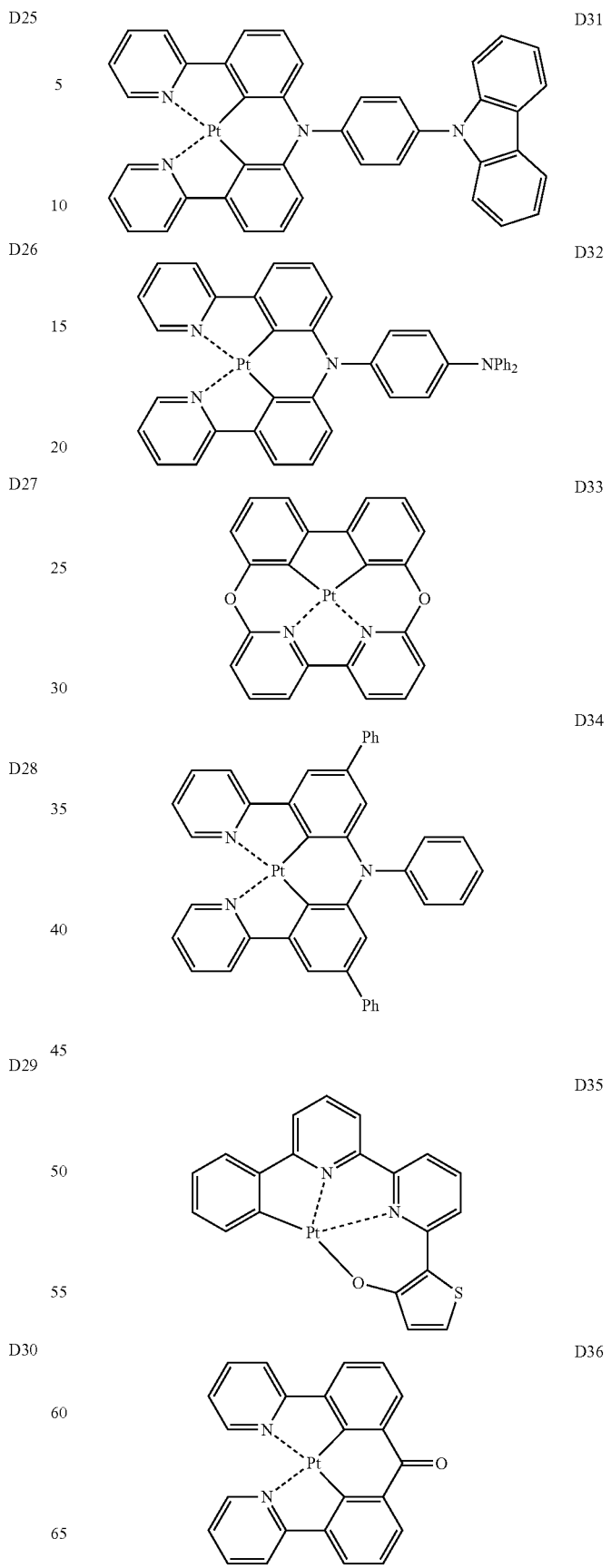

D37 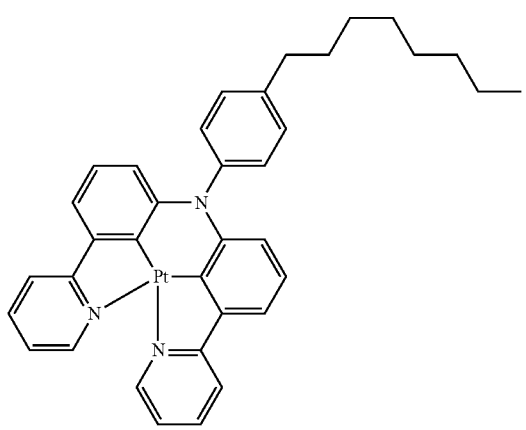
D38 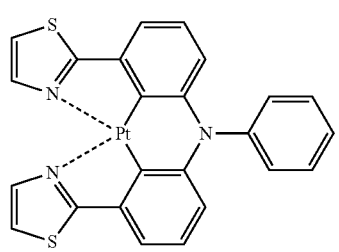
D39 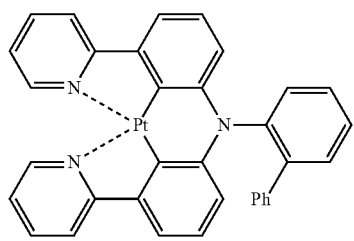
D40 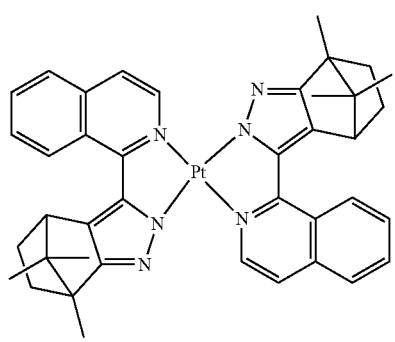
D41 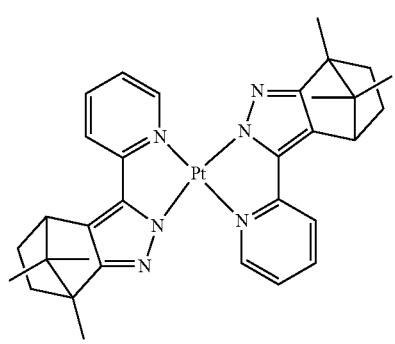
D42 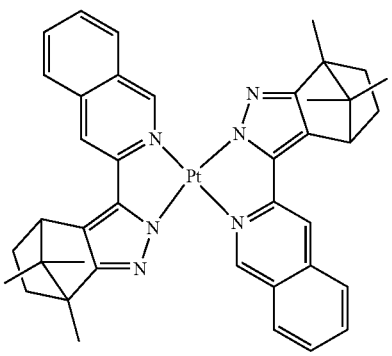
D43 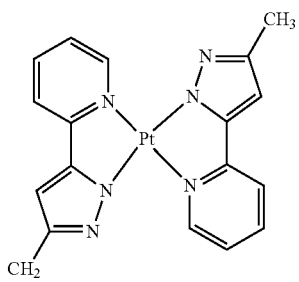
D44 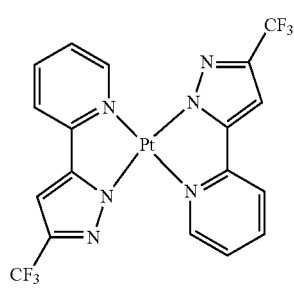
D45 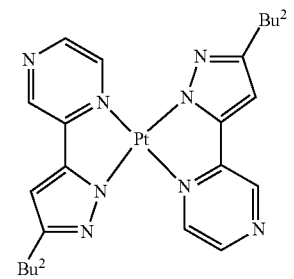
D46 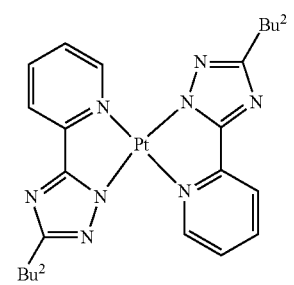

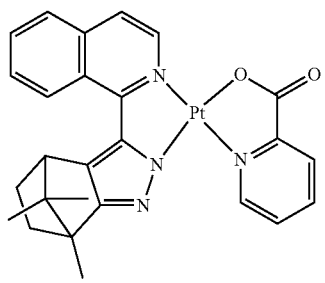
D47

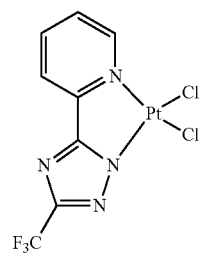
D48

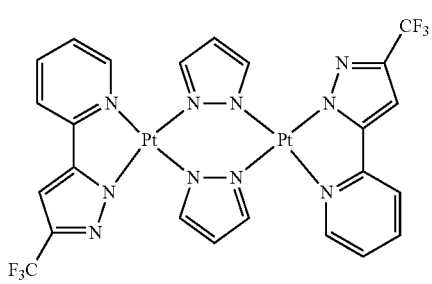
D49

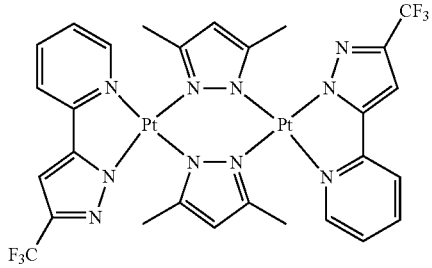
D50

In addition, the dopant used in the EML may be an Os-complex, which will be described later, but is not limited thereto.

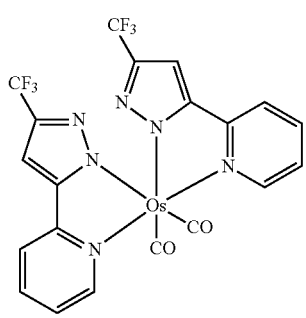
Os(fppz)₂(CO)₂

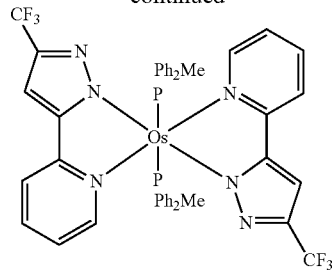
Os(fppz)₂(PPh₂Me)₂

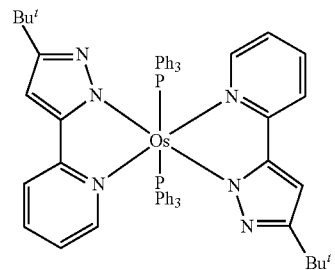
Os(bppz)₂(PPh₃)₂

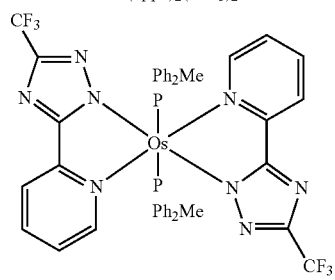
Os(fptz)₂(PPh₂Me)₂

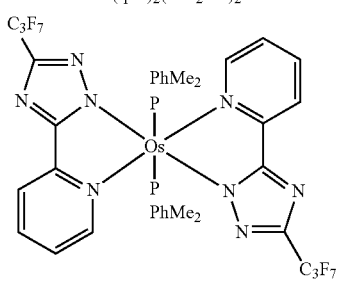
Os(hptz)₂(PPhMe₂)₂

If the EML includes a host and a dopant, the amount of the dopant may be in the range of about 0.01 to about 15 parts by weight based on 100 parts by weight of the host, but is not limited thereto.

The thickness of the EML may be in the range of about 100 Å to about 1000 Å, or for example, about 200 Å to about 600 Å. When the thickness of the EML is within this range, the EML may have excellent light emitting ability without a substantial increase in driving voltage.

Then, the ETL may be formed on the EML by vacuum deposition, spin coating, casting, or the like. When the ETL is formed using vacuum deposition or spin coating, the deposition and coating conditions may be similar to those for formation of the HIL, although the deposition and coating conditions may vary according to a compound that is used to form the ETL. A material that is used to form the ETL may be any material stably transporting electrons injected from the electron injecting electrode (cathode). Examples of known electron transporting materials include quinoline derivatives, such as tris-(8-hydroxyquinoline) aluminum (Alq3), TAZ, Balq, beryllium bis(benzoquinolin-10-olate) (Balq$_2$), ADN, Compound 201, and Compound 202, but are not limited thereto.

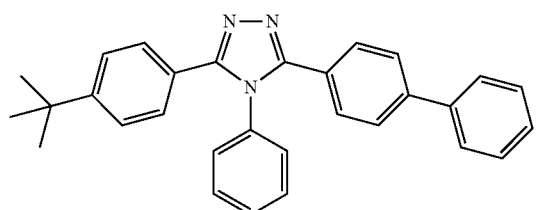

TAZ

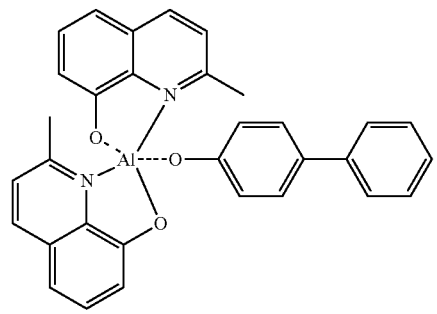

BAlq

Compound 201

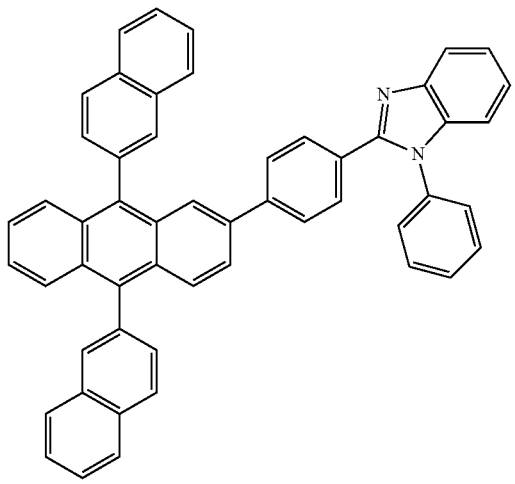

Compound 202

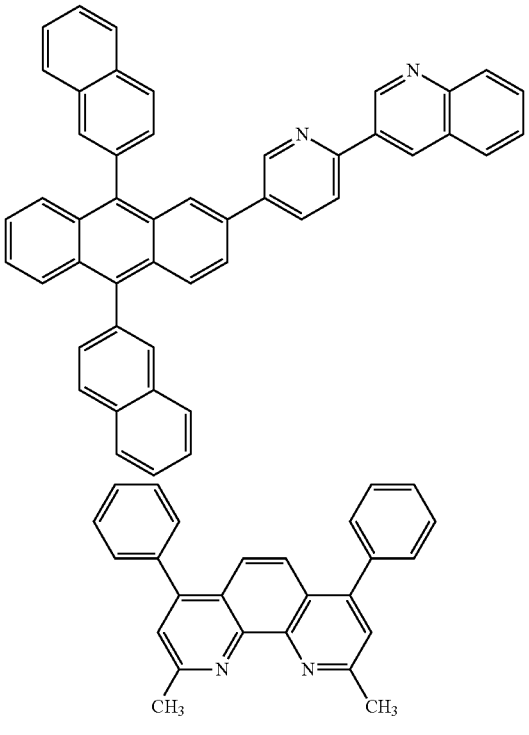

BCP

The thickness of the ETL may be in the range of about 100 Å to about 1,000 Å, for example, about 150 Å to about 500 Å. When the thickness of the ETL is within the described range, the ETL may have excellent electron transporting ability without imparting a substantial increase in driving voltage.

Alternatively, the ETL may further include a metal-containing material in addition to known electron transporting organic compounds.

The metal-containing material may include a Li complex. Examples of the Li complex include lithium quinolate (LiQ) or Compound 203 below but are not limited thereto.

Compound 203

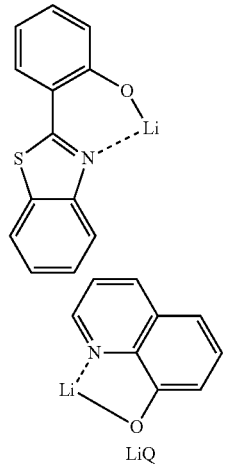

LiQ

In addition, the EIL may be formed on the ETL using any material that allows electrons to be easily injected from the cathode.

Examples of electron injecting materials include LiF, NaCl, CsF, $Li_2O$, and BaO, which are known in the art. The conditions for deposition of the EIL are similar to those for formation of the HIL, although the deposition conditions may vary depending upon the material that is used to form the EIL.

The thickness of the EIL may be in the range of about 1 to about 100 Å, or, for example, in the range of about 3 to about 90 Å. When the thickness of the EIL is within this range, the EIL may have excellent electron injecting ability without imparting a substantial increase in driving voltage.

A second electrode 17 is disposed on the organic layer 15. The second electrode 17 may be a cathode, which is an electron injecting electrode. A metal used to form the second electrode 17 may be a metal, an alloy, an electrically conductive compound that has a low work function, or a mixture thereof. For example, the second electrode 17 may be selected from a transmissive electrode formed of lithium (Li), magnesium (Mg), aluminum (Al), an Al:Li alloy, calcium (Ca), a Mg:In alloy, and a Mg:Ag alloy in a thin film. Meanwhile, in order to manufacture a top-emission type organic light-emitting device, a transmissive electrode formed of ITO or IZO may be used, and various modifications may be applied thereto.

The organic light-emitting diode is described with reference to FIG. 1, but is not limited thereto.

In addition, when a phosphorescent dopant is used to form the EML, an HBL may be formed between the HTL and the EML or between the H-functional layer and the EML by using vacuum deposition, spin coating, casting, LB deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole blocking material that is commonly used in the art may be used. Examples of known hole blocking materials include an oxadiazole derivative, a triazole derivative, and a phenanthroline derivative. For example, BCP may be used as the hole blocking material.

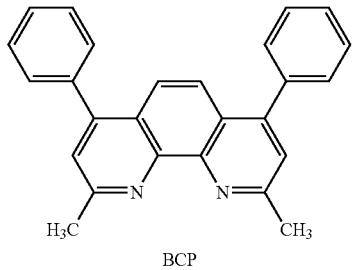

BCP

The thickness of the HBL may be in a range of about 20 to about 1,000 Å, or, for example, about 30 to about 300 Å. When the thickness of the HBL is within this range, the HBL may have excellent hole blocking ability without a substantial increase in driving voltage.

Hereinafter, one or more embodiments will be described in detail with reference to the following examples. These examples are not intended to limit the purpose and scope of the one or more embodiments of the present invention.

Examples of the unsubstituted $C_1$-$C_{60}$ alkyl group (or the $C_1$-$C_{60}$ alkyl group) used herein are a linear or branched $C_1$-$C_{60}$ alkyl group such as methyl, ethyl, propyl, isobutyl, sec-butyl, pentyl, iso-amyl, and hexyl. The substituted $C_1$-$C_{60}$ alkyl group is obtained by substituting at least one hydrogen atom of the unsubstituted $C_1$-$C_{60}$ alkyl group with one of deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —$N(Q_{11})(Q_{12})$, and $Si(Q_{13})(Q_{14})(Q_{15})$, where $Q_{11}$ to $Q_{15}$ are each independently hydrogen, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group.

The unsubstituted $C_1$-$C_{60}$ alkoxy group (or the $C_1$-$C_{60}$ alkoxy group) used herein may be represented by —OA, A being an unsubstituted $C_1$-$C_{60}$ alkyl group. Examples of the $C_1$-$C_{60}$ alkoxy group include methoxy, ethoxy, and isopropyloxy, and at least one hydrogen atom of the $C_1$-$C_{60}$ alkoxy group may be substituted with the same substituent groups described above with reference to the $C_1$-$C_{60}$ alkyl group.

The unsubstituted $C_2$-$C_{60}$ alkenyl group (or $C_2$-$C_{60}$ alkenyl group) used herein refers to a hydrocarbon chain having at least one carbon-carbon double bond within or at a terminal of the unsubstituted $C_2$-$C_{60}$ alkyl group. Examples of the $C_2$-$C_{60}$ alkenyl group include ethenyl, propenyl, and butenyl. At least one hydrogen atom in the unsubstituted $C_2$-$C_{60}$ alkenyl group may be substituted with the same substituent groups described above with reference to the $C_1$-$C_{60}$ alkyl group.

The unsubstituted $C_2$-$C_{60}$ alkynyl group (or the $C_2$-$C_{60}$ alkynyl group) used herein refers to a hydrocarbon chain having at least one carbon-carbon triple bond within or at a terminal of the unsubstituted $C_2$-$C_{60}$ alkyl group. Examples of the $C_2$-$C_{60}$ alkenyl group include ethynyl and propynyl. At least one hydrogen atom in the unsubstituted $C_2$-$C_{60}$ alkynyl group may be substituted with the same substituent groups described above with reference to the $C_1$-$C_{60}$ alkyl group.

The unsubstituted $C_5$-$C_{60}$ aryl group used herein refers to a monovalent group having a $C_5$-$C_{60}$ carbocyclic aromatic system including at least one aromatic ring. The unsubstituted $C_5$-$C_{60}$ arylene group used herein refers to a divalent group having a $C_5$-$C_{60}$ carbocyclic aromatic system including at least one aromatic ring. If the aryl group and arylene group include at least two rings, they may be fused to each other. At least one hydrogen atom in the aryl group and arylene group may be substituted with the same substituent groups described above with reference to the $C_1$-$C_{60}$ alkyl group.

Examples of the substituted or unsubstituted $C_5$-$C_{60}$ aryl group are a phenyl group, a $C_1$-$C_{10}$ alkylphenyl group (e.g., ethylphenyl group), a $C_1$-$C_{10}$ alkylbiphenyl group (e.g., ethylbiphenyl group), a halophenyl group (e.g., o-, m-, and p-fluorophenyl group and dichlorophenyl group), a dicyanophenyl group, a trifluoromethoxyphenyl group, an o-, m-, and p-tolyl group, an o-, m-, and p-cumenyl group, a mesityl group, a phenoxyphenyl group, an (α,α-dimethylbenzene) phenyl group, an (N,N'-dimethyl)aminophenyl group, an (N,N'-diphenyl)aminophenyl group, a pentalenyl group, an indenyl group, a naphthyl group, a halonaphthyl group (e.g., fluoronaphthyl group), a $C_1$-$C_{10}$ alkylnaphthyl group (e.g., methylnaphthyl group), a $C_1$-$C_{10}$ alkoxynaphthyl group (e.g., methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group. Examples of the substituted $C_5$-$C_{60}$ aryl group may be easily derived from examples of the unsubstituted $C_5$-$C_{60}$ aryl group as described above and the substituents of the substituted $C_1$-$C_{60}$ alkyl group. Examples of the substituted or unsubstituted $C_5$-$C_{60}$ arylene group may be easily derived from examples of the substituted or unsubstituted $C_5$-$C_{60}$ aryl group.

The unsubstituted $C_2$-$C_{60}$ heteroaryl group is a monovalent group having at least one aromatic ring having at least one of the heteroatoms selected from N, O, P, and S. The unsubstituted $C_2$-$C_{60}$ heteroarylene group is a divalent group having at least one aromatic ring having at least one of the heteroatoms selected from N, O, P, and S. In this regard, when the heteroaryl group and the heteroarylene group have at least two rings, they may be fused to each other. At least one hydrogen atom in the heteroaryl group and the heteroarylene group may be substituted with the same substituent groups described above with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily derived from examples of the substituted or unsubstituted $C_2$-$C_{60}$ arylene group.

The substituted or unsubstituted $C_5$-$C_{60}$ aryloxy group is —$OA_2$, $A_2$ being a substituted or unsubstituted $C_5$-$C_{60}$ aryl group. The substituted or unsubstituted $C_5$-$C_{60}$ arylthio group is —$SA_3$, $A_3$ being a substituted or unsubstituted $C_5$-$C_{60}$ aryl group.

EXAMPLES

Synthesis Example 1

Synthesis of Compound 1

Compound 1 was synthesized through Reaction Scheme 1 below.

Reaction Scheme 1

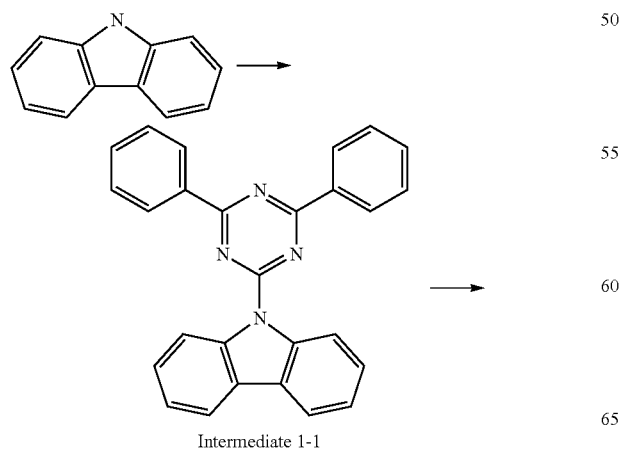

Intermediate 1-1

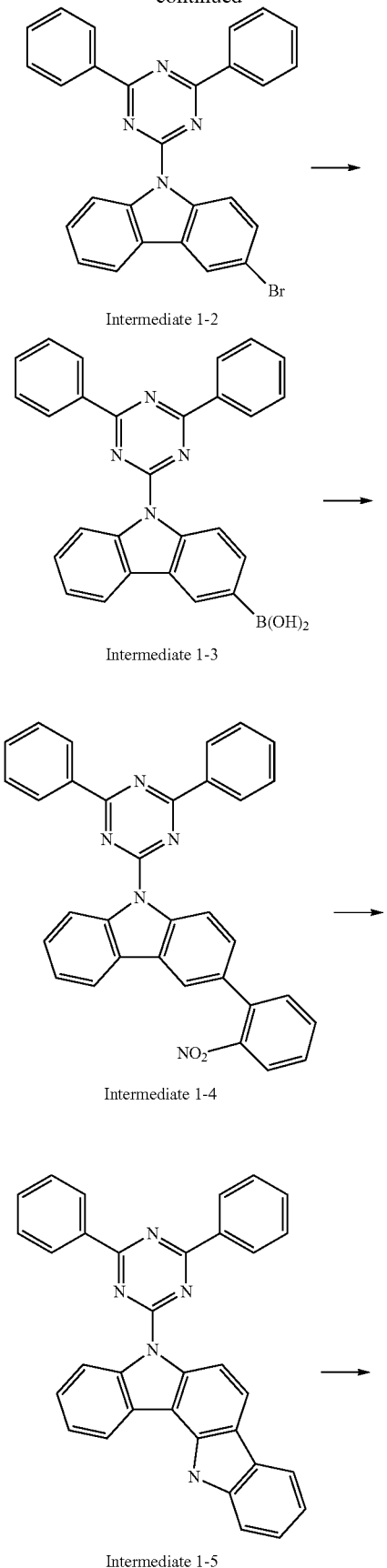

Intermediate 1-2

Intermediate 1-3

Intermediate 1-4

Intermediate 1-5

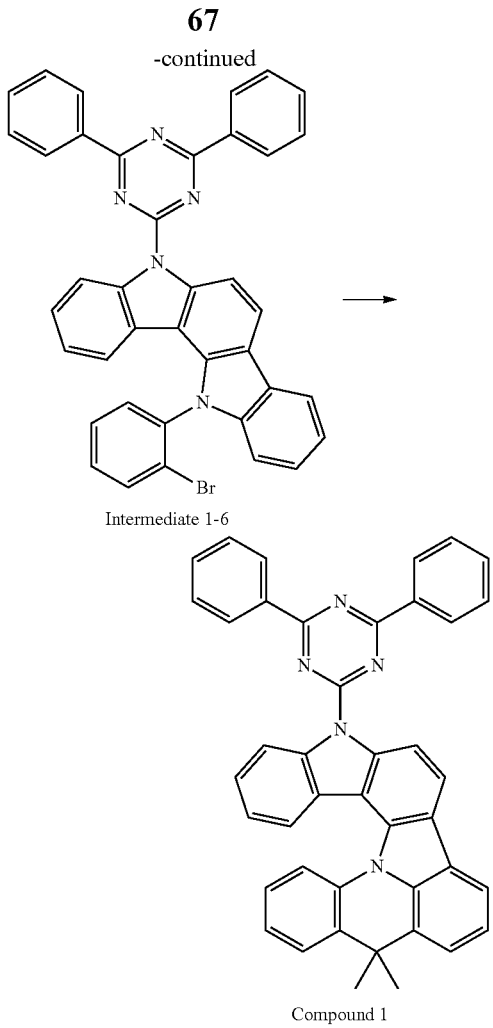

Intermediate 1-6

Compound 1

Synthesis of Intermediate 1-1

20 g (119.61 mmol) of carbazole was dissolved in 100 ml of dimethylformamide (DMF), and the solution was added to a reactor in which 7.07 g (179.42 mmol, 60% dispersion in mineral oil) of NaH was dissolved in 100 ml of DMF. After one hour, 38.42 g (143.53 mmol) of 2-chloro-4,6-diphenyl-triazine dissolved in 100 ml of DMF was added thereto. The mixture was stirred for 12 hours, and then distilled water was added thereto to obtain a solid. The solid was filtered under reduced pressure and recrystallized using ethyl acetate (EA) and DMF to obtain 25.74 g (64.59 mmol, 54%) of Intermediate 1-1.

Synthesis of Intermediate 1-2

20 g (50.19 mmol) of Intermediate 1-1 was dissolved in 200 ml of DMF, and 9.83 g (55.21 mmol) of N-bromosuccinimide (NBS) was added thereto. After the mixture was stirred at room temperature for 10 hours, the organic solvent was distilled under reduced pressure, and water was added thereto. The resultant was subjected to extraction using acetate (EA). The resultant was dried using magnesium sulfate, distilled under reduced pressure, and separately purified using column chromatography to obtain 22.04 g (41.90 mmol, 92%) of Intermediate 1-2.

Synthesis of Intermediate 1-3

20 g (41.90 mmol) of Intermediate 1-2 was dissolved in 200 ml of tetrahydrofuran (THF), and 16.76 ml (41.90 mmol, 2.5M in hexane) of n-buLi was slowly added thereto at −78° C. After stifling for 1 hour, 6.07 ml (54.47 mmol) of trimethyl borate was added thereto, and the mixture was heated to room temperature and stirred for 12 hours. Distilled water was added thereto and the mixture was subjected to extraction using EA, dried using magnesium sulfate, and distilled under reduced pressure. The resultant was separately purified using column chromatography to obtain 7.41 g (16.67 mmol, 40%) of Intermediate 1-3.

Synthesis of Intermediate 1-4

10 g (22.61 mmol) of Intermediate 1-3 and 5.48 g (27.13 mmol) of bromo-2-nitrobenzene, 0.79 g (0.68 mmol) of tetrakis(triphenylphosphine)palladium(0)(Pd(PPh$_3$)$_4$), 22.18 ml (45.22 mmol) of 2M K$_2$CO$_3$ aqueous solution, 80 ml of toluene, and 30 ml of ethanol were refluxed while stifling. After 4 hours, the mixture was cooled to room temperature, and distilled water was added thereto. The mixture was subjected to extraction using EA, dried using magnesium sulfate, and distilled under reduced pressure. The resultant was separately purified using column chromatography to obtain 8.69 g (16.73 mmol, 74%) of Intermediate 1-4.

Synthesis of Intermediate 1-5

10 g (19.25 mmol) of Intermediate 1-4 was mixed with 100 ml of triethylphosphite, and the mixture was stirred at 180° C. After 10 hours, the mixture was cooled to room temperature, and an organic solvent was distilled under reduced pressure. Distilled water was added thereto, and the mixture was subjected to extraction using EA, dried using magnesium sulfate, and distilled under reduced pressure. The resultant was separately purified using column chromatography to obtain 5.62 g (11.55 mmol, 60%) of Intermediate 1-5.

Synthesis of Intermediate 1-6

10 g (20.55 mmol) of Intermediate 1-5, 11.63 g (41.11 mmol) of 2-bromoiodobenzene, 1.96 g (10.28 mmol) of CuI, and 5.68 g (41.11 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using methyl chloride (MC), dried using magnesium sulfate, and distilled under reduced pressure. The resultant was separately purified using column chromatography to obtain 5.55 g (8.63 mmol, 42%) of Intermediate 1-6.

Synthesis of Compound 1

10 g (15.56 mmol) of Intermediate 1-6 was dissolved in 100 ml of THF, and 6.22 ml (15.56 mmol, 2.5M in hexane) of n-buLi was slowly added thereto at −78° C. After stifling for 2 hours, 1.20 ml (20.23 mmol) of acetone was added thereto, and the mixture was heated to room temperature slowly. Then, a NaHCO$_3$ aqueous solution was added thereto, and the mixture was subjected to extraction using methylene chloride (MC). The resultant was dried using magnesium sulfate, distilled under reduced pressure, and added to a separate two-neck flask to be mixed with 100 ml of acetic acid. A HCl aqueous solution (5 mol %, 12N) in a catalytic amount was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 5.45 g (9.03 mmol, 58%) of Compound 1.

MS: m/z 603.24 [M]$^+$ $^1$H NMR (CDCl$_3$) δ 7.55 (2H), 7.48 (4H), 7.40 (1H), 7.37 (1H), 7.32 (4H), 7.22 (2H), 7.20 (2H), 7.10 (2H), 7.08 (1H), 7.00 (2H), 6.95 (1H), 6.92 (1H), 1.67 (6H)

Synthesis Example 2

Synthesis of Compound 2

10 g (15.56 mmol) of Intermediate 1-6 that was prepared in the same manner as in Synthesis Example 1 was dissolved in 100 ml of THF, and 6.22 ml (15.56 mmol, 2.5M in hexane) of n-buLi was slowly added thereto at −78° C. After stifling for 2 hours, 3.69 g (20.23 mmol) of benzophenone dissolved in 50 ml of THF was added thereto, and the mixture was heated to room temperature slowly. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. Then, a HCl aqueous solution (5 mol %, 12N) was added thereto, and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 6.12 g (8.40 mmol, 54%) of Compound 2.

MS: m/z 727.27 [M]$^+$ $^1$H NMR (CDCl$_3$) δ 7.55 (2H), 7.48 (4H), 7.40 (1H), 7.36 (1H), 7.32 (4H), 7.22 (2H), 7.14 (4H), 7.10 (4H), 7.08 (1H), 7.07 (2H), 7.06 (4H), 7.00 (2H), 6.88 (2H)

Synthesis Example 3

Synthesis of Compound 3

Compound 3 was synthesized through Reaction Scheme 3 below.

Reaction Scheme 3

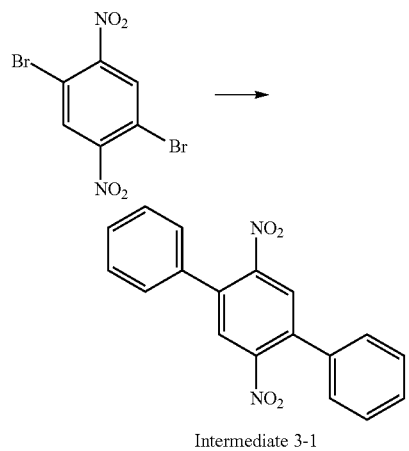

Intermediate 3-1

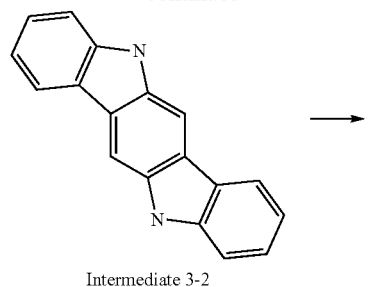

Intermediate 3-2

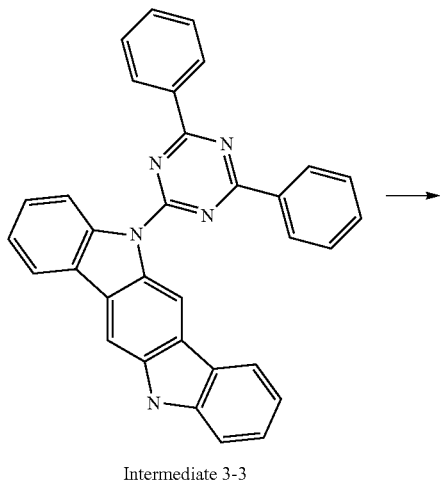

Intermediate 3-3

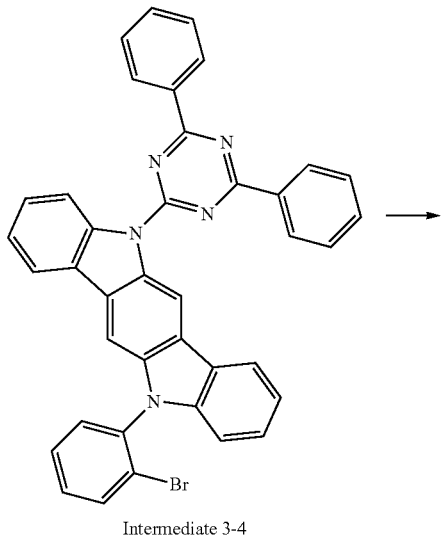

Intermediate 3-4

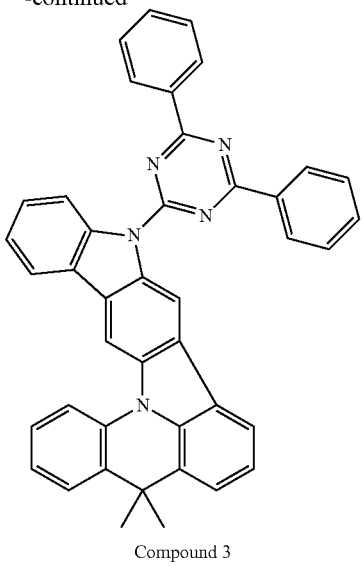

Compound 3

Synthesis of Intermediate 3-1

20 g (61.36 mmol) of 1,4-dibromo-2,5-dinitrobenzene, 18.7 g (153.40 mmol) of 1-phenylboronic acid, 4.30 g (3.68 mmol) of Pd(PPh$_3$)$_4$, 90.29 ml (184.08 mmol) of 2M K$_2$CO$_3$ aqueous solution, 80 ml of toluene, and 100 ml of ethanol were mixed and refluxed while stirring. After 10 hours, the mixture was cooled to room temperature, and distilled water was added thereto. The mixture was subjected to extraction using EA, dried using magnesium sulfate, and distilled under reduced pressure. The resultant was separately purified using column chromatography to obtain 16.99 g (53.38 mmol, 87%) of Intermediate 3-2.

Synthesis of Intermediate 3-2

9.27 g (36.44 mmol, 58%) of Intermediate 3-2 was prepared in the same manner as in the synthesis of Intermediate 1-5 of Synthesis Example 1, except that 20 g (62.83 mmol) of Intermediate 3-1 and 200 ml of triethylphosphite were used instead of 10 g of Intermediate 1-4 and 100 ml of triethylphosphite.

Synthesis of Intermediate 3-3

20 g (78.65 mmol) of Intermediate 3-2 was dissolved in 100 ml of DMF, and the solution was added to a reactor in which 4.65 g (117.98 mmol, 60% dispersion in mineral oil) of NaH was dissolved in 100 ml of DMF. After one hour, 37.90 g (141.57 mmol) of 2-chloro-4,6-diphenyltriazine dissolved in 100 ml of DMF was added thereto. The mixture was stirred for 12 hours, and then distilled water was added thereto to obtain a solid. The solid was filtered under reduced pressure and recrystallized using EA and DMF to obtain 10.71 g (22.02 mmol, 28%) of Intermediate 3-3.

Synthesis of Intermediate 3-4

5.28 g (8.22 mmol, 40%) of Intermediate 3-4 was prepared in the same manner as in the synthesis of Intermediate 1-6 of Synthesis Example 1, except that Intermediate 3-3 was used instead of Intermediate 1-5.

Synthesis of Compound 3

5.07 g (8.40 mmol, 54%) of Compound 3 was prepared in the same manner as in the synthesis of Compound 1 of Synthesis Example 1, except that Intermediate 3-4 was used instead of Intermediate 1-6.

MS: m/z 603.24 [M]$^+$ $^1$H NMR (CDCl$_3$) δ 7.55 (2H), 7.48 (4H), 7.40 (2H), 7.37 (1H), 7.32 (4H), 7.22 (2H), 7.20 (2H), 7.10 (2H), 7.08 (1H), 7.00 (1H), 6.95 (1H), 6.92 (1H), 1.67 (6H)

Synthesis Example 4

Synthesis of Compound 4

Compound 4 was synthesized through Reaction Scheme 4 below.

Reaction Scheme 4

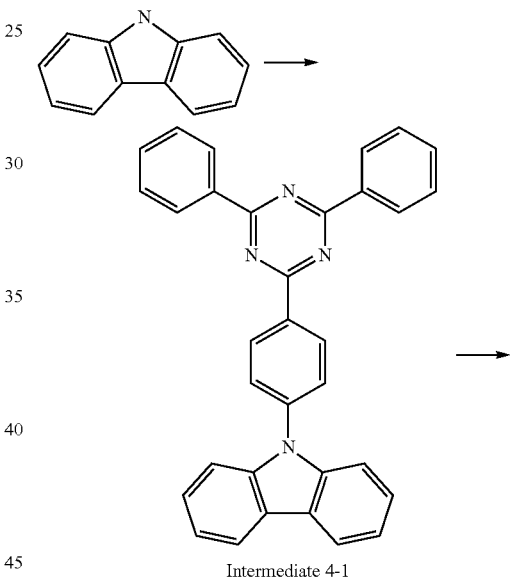

Intermediate 4-1

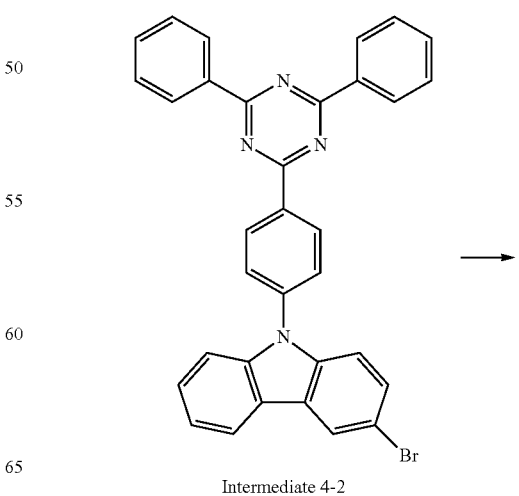

Intermediate 4-2

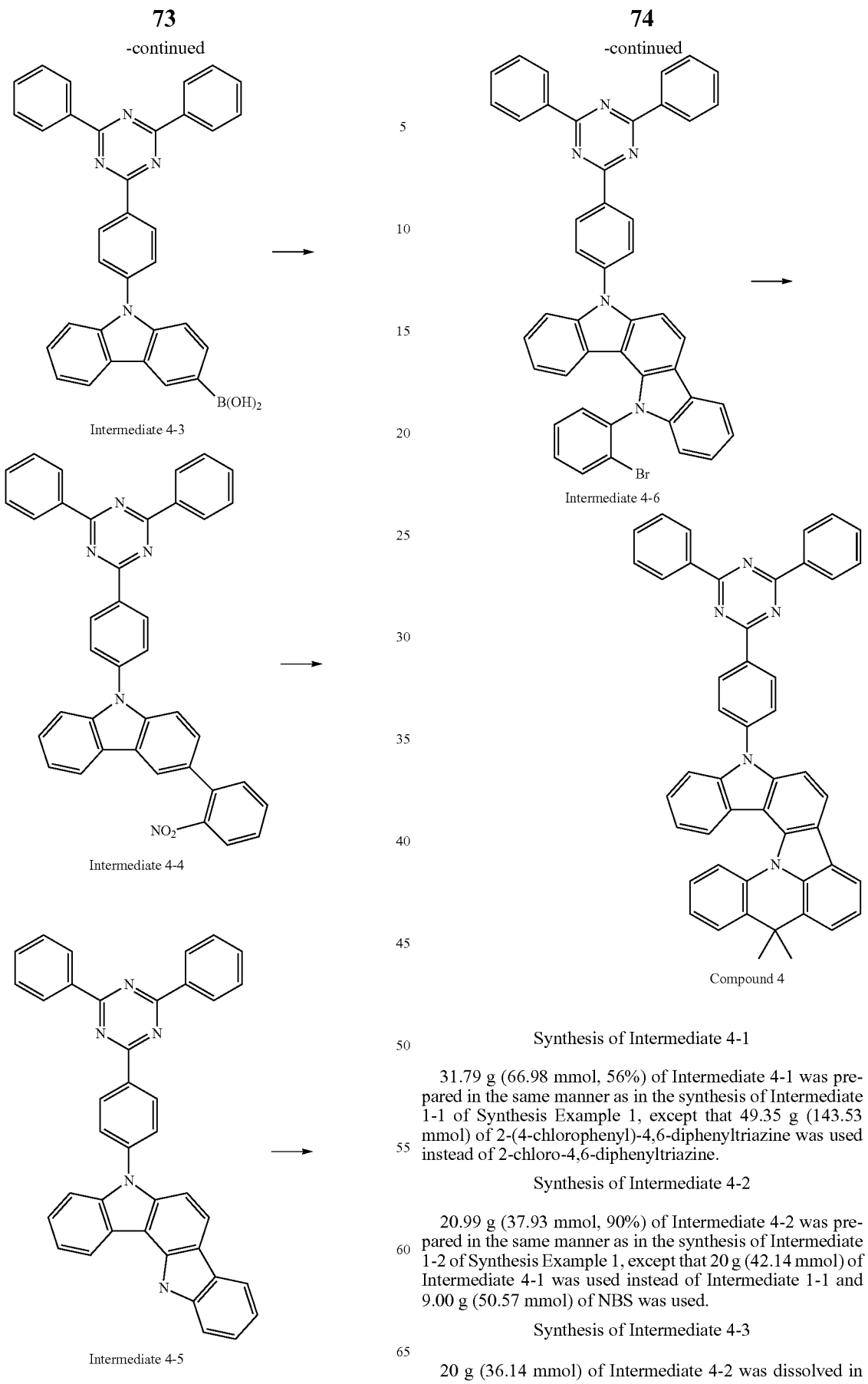

Synthesis of Intermediate 4-1

31.79 g (66.98 mmol, 56%) of Intermediate 4-1 was prepared in the same manner as in the synthesis of Intermediate 1-1 of Synthesis Example 1, except that 49.35 g (143.53 mmol) of 2-(4-chlorophenyl)-4,6-diphenyltriazine was used instead of 2-chloro-4,6-diphenyltriazine.

Synthesis of Intermediate 4-2

20.99 g (37.93 mmol, 90%) of Intermediate 4-2 was prepared in the same manner as in the synthesis of Intermediate 1-2 of Synthesis Example 1, except that 20 g (42.14 mmol) of Intermediate 4-1 was used instead of Intermediate 1-1 and 9.00 g (50.57 mmol) of NBS was used.

Synthesis of Intermediate 4-3

20 g (36.14 mmol) of Intermediate 4-2 was dissolved in 200 ml of tetrahydrofuran (THF), and 14.45 ml (41.90 mmol, 2.5M in hexane) of n-buLi was slowly added thereto at −78° C. After stirring for 1 hour, 5.23 ml (46.98 mmol) of trimethyl borate was added thereto, and the mixture was heated to room temperature and stirred for 12 hours. Distilled water was added thereto and the mixture was subjected to extraction using EA, dried using magnesium sulfate, and distilled under reduced pressure. The resultant was separately purified using column chromatography to obtain 7.49 g (14.45 mmol, 40%) of Intermediate 4-3.

Synthesis of Intermediate 4-4

10 g (19.29 mmol) of Intermediate 4-3 and 4.67 g (23.15 mmol) of bromo-2-nitrobenzene, 0.68 g (0.58 mmol) of Pd(PPh$_3$)$_4$, 18.92 ml (38.58 mmol) of 2M K$_2$CO$_3$ aqueous solution, 80 ml of toluene, and 30 ml of ethanol were refluxed while stifling. After 4 hours, the mixture was cooled to room temperature, and distilled water was added thereto. The mixture was subjected to extraction using EA, dried using magnesium sulfate, and distilled under reduced pressure. The resultant was separately purified using column chromatography to obtain 8.27 g (13.89 mmol, 72%) of Intermediate 4-4.

Synthesis of Intermediate 4-5

5.67 g (10.07 mmol, 60%) of Intermediate 4-5 was prepared in the same manner as in the synthesis of Intermediate 1-5 of Synthesis Example 1, except that 10 g (16.79 mmol) of Intermediate 4-4 was used instead of Intermediate 1-4.

Synthesis of Intermediate 4-6

10 g (17.77 mmol) of Intermediate 4-5, 10.06 g (35.55 mmol) of 2-bromoiodobenzene, 1.69 g (8.89 mmol) of CuI, and 4.91 g (35.55 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 5.11 g (7.11 mmol, 40%) of Intermediate 4-6.

Synthesis of Compound 4

10 g (13.91 mmol) of Intermediate 4-6 was dissolved in 100 ml of THF, and 5.56 ml (13.91 mmol, 2.5M in hexane) of n-buLi was slowly added thereto at −78° C. After stifling for 2 hours, 1.05 ml (18.09 mmol) of acetone was added thereto, and the mixture was heated to room temperature slowly. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. A HCl aqueous solution (5 mol %, 12N) having the same amount as the catalyst was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 5.68 g (8.35 mmol, 60%) of Compound 4.

MS: m/z 679.27 [M]$^+$ $^1$H NMR (CDCl$_3$) δ 7.55 (2H), 7.50 (2H), 7.48 (4H), 7.40 (1H), 7.37 (1H), 7.32 (4H), 7.30 (2H), 7.22 (2H), 7.20 (2H), 7.10 (2H), 7.08 (1H), 7.00 (2H), 6.95 (1H), 6.92 (1H), 1.67 (6H)

Synthesis Example 5

Synthesis of Compound 5

Compound 5 was synthesized through Reaction Scheme 5 below.

Reaction Scheme 5

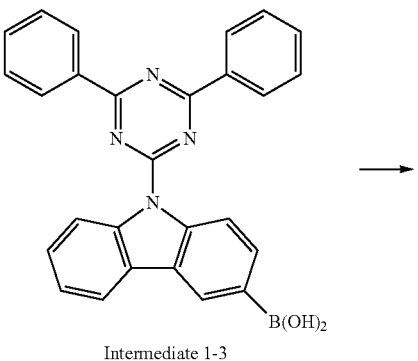

Intermediate 1-3

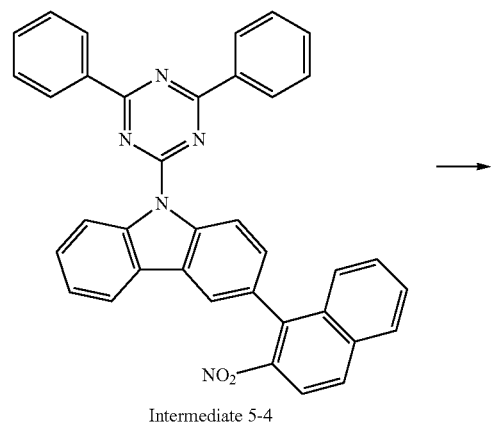

Intermediate 5-4

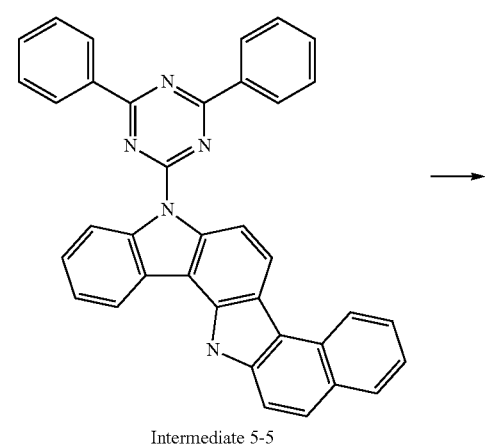

Intermediate 5-5

-continued

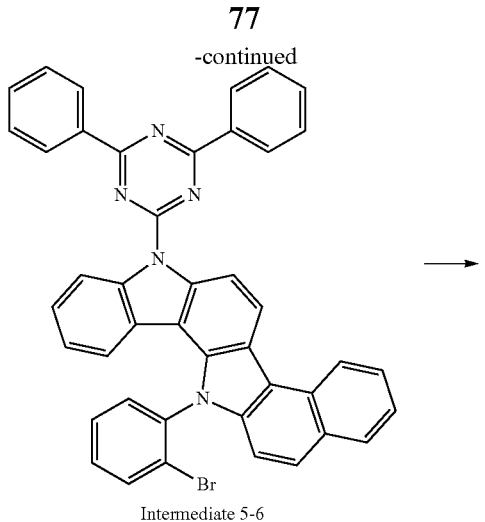

Intermediate 5-6

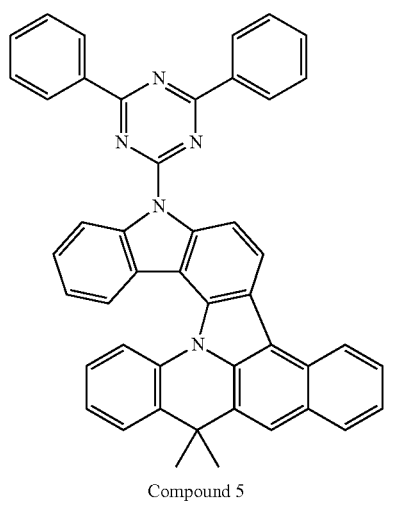 [SMILES: CC1(C)c2ccccc2-n2c3c1cc1ccccc1c3c1ccc3c(c4ccccc4n3-c3nc(-c4ccccc4)nc(-c4ccccc4)n3)c12]

Compound 5

Synthesis of Intermediate 5-4

8.76 g (15.37 mmol, 68%) of Intermediate 5-4 was prepared in the same manner as in the synthesis of Intermediate 1-4 of Synthesis Example 1, except that 6.84 g (27.13 mmol) of bromo-2-nitronaphthalene was used instead of bromo-2-nitrobenzene.

Synthesis of Intermediate 5-5

5.65 g (10.53 mmol, 60%) of Intermediate 5-5 was prepared in the same manner as in the synthesis of Intermediate 1-5 of Synthesis Example 1, except that 10 g (17.56 mmol) of Intermediate 5-4 was used instead of Intermediate 1-4.

Synthesis of Intermediate 5-6

10 g (18.64 mmol) of Intermediate 5-5, 10.54 g (37.27 mmol) of 2-bromoiodobenzene, 1.78 g (9.32 mmol) of CuI and 5.15 g (37.27 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 5.16 g (7.45 mmol, 40%) of Intermediate 5-6.

Synthesis of Compound 5

10 g (14.44 mmol) of Intermediate 5-6 was dissolved in 100 ml of THF, and 5.77 ml (14.44 mmol, 2.5M in hexane) of n-buLi was slowly added thereto at −78° C. After stifling for 2 hours, 1.09 ml (18.77 mmol) of acetone was added thereto, and the mixture was heated to room temperature. Then, a $NaHCO_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. A HCl aqueous solution (5 mol %, 12N) in a catalytic amount was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 5.10 g (7.80 mmol, 54%) of Compound 5.

MS: m/z 653.26 $[M]^+$ $^1$H NMR ($CDCl_3$) δ 7.67 (2H), 7.55 (2H), 7.48 (4H), 7.40 (1H), 7.32 (4H), 7.22 (2H), 7.20 (2H), 7.10 (2H), 7.08 (1H), 7.00 (2H), 6.87 (1H), 1.73 (6H)

Synthesis Example 6

Synthesis of Compound 6

Compound 6 was synthesized through Reaction Scheme 6 below.

Reaction Scheme 6

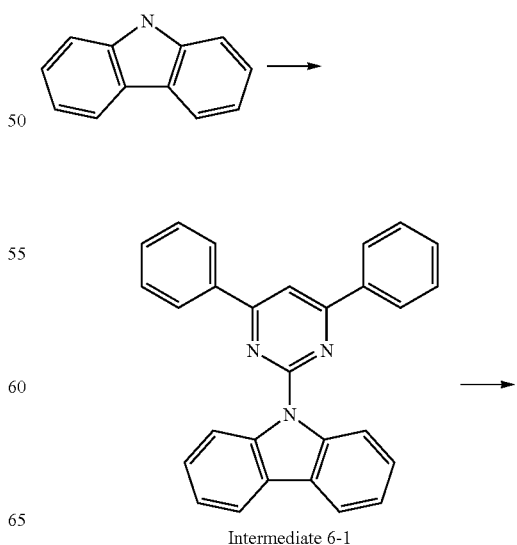

Intermediate 6-1

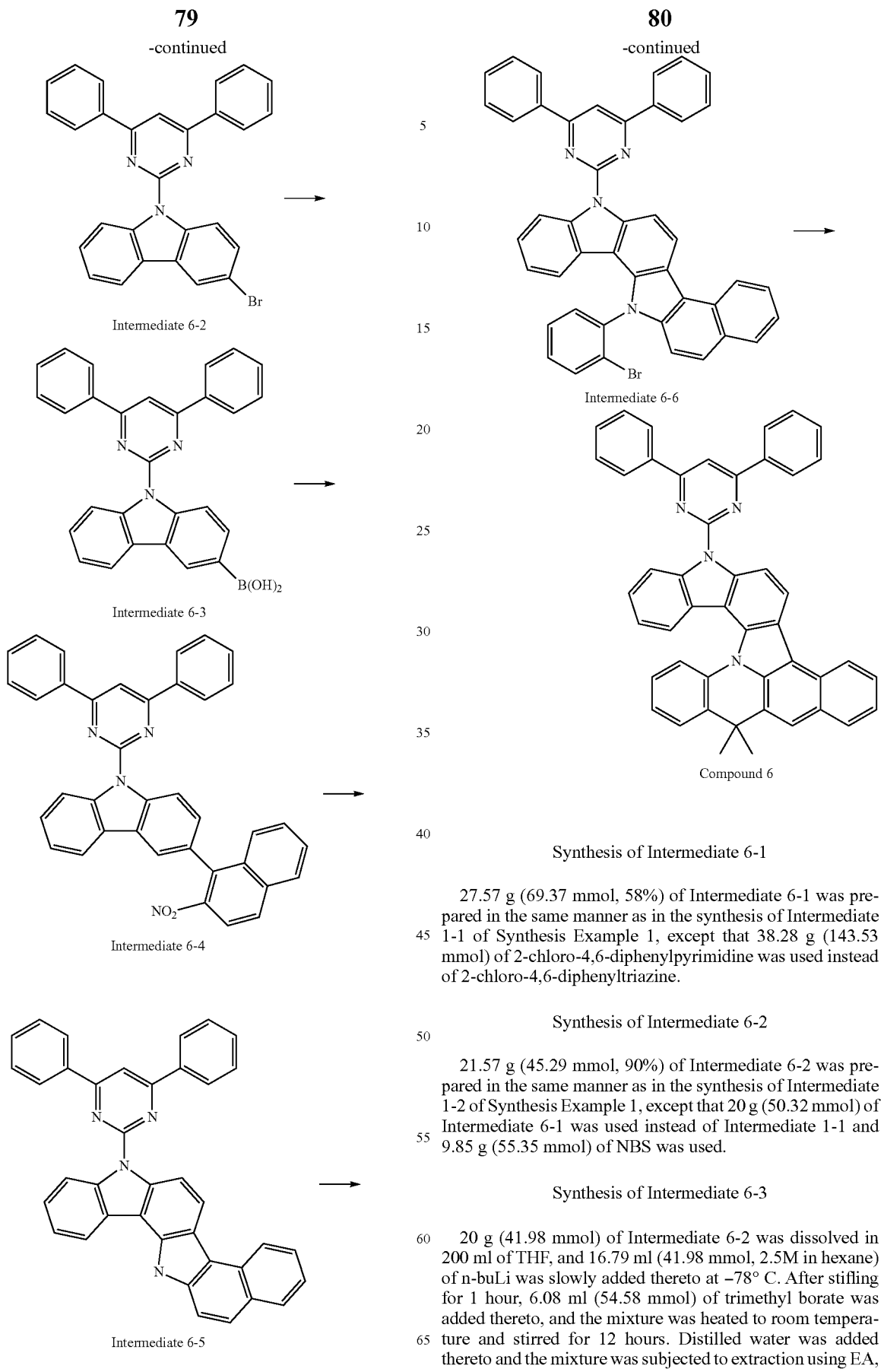

Synthesis of Intermediate 6-1

27.57 g (69.37 mmol, 58%) of Intermediate 6-1 was prepared in the same manner as in the synthesis of Intermediate 1-1 of Synthesis Example 1, except that 38.28 g (143.53 mmol) of 2-chloro-4,6-diphenylpyrimidine was used instead of 2-chloro-4,6-diphenyltriazine.

Synthesis of Intermediate 6-2

21.57 g (45.29 mmol, 90%) of Intermediate 6-2 was prepared in the same manner as in the synthesis of Intermediate 1-2 of Synthesis Example 1, except that 20 g (50.32 mmol) of Intermediate 6-1 was used instead of Intermediate 1-1 and 9.85 g (55.35 mmol) of NBS was used.

Synthesis of Intermediate 6-3

20 g (41.98 mmol) of Intermediate 6-2 was dissolved in 200 ml of THF, and 16.79 ml (41.98 mmol, 2.5M in hexane) of n-buLi was slowly added thereto at −78° C. After stifling for 1 hour, 6.08 ml (54.58 mmol) of trimethyl borate was added thereto, and the mixture was heated to room temperature and stirred for 12 hours. Distilled water was added thereto and the mixture was subjected to extraction using EA, dried using magnesium sulfate, and distilled under reduced pressure. The resultant was separately purified using column chromatography to obtain 7.41 g (16.79 mmol, 40%) of Intermediate 6-3.

Synthesis of Intermediate 6-4

10 g (22.66 mmol) of Intermediate 6-3 and 6.85 g (27.19 mmol) of bromo-2-nitronaphthalene, 0.79 g (0.68 mmol) of Pd(PPh$_3$)$_4$, 22.23 ml (45.32 mmol) of 2M K$_2$CO$_3$ aqueous solution, 80 ml of toluene, and 30 ml of ethanol were refluxed while stirring. After 4 hours, the mixture was cooled to room temperature, and distilled water was added thereto. The mixture was subjected to extraction using EA, dried using magnesium sulfate, and distilled under reduced pressure. The resultant was separately purified using column chromatography to obtain 10.05 g (17.68 mmol, 78%) of Intermediate 6-4.

Synthesis of Intermediate 6-5

5.84 g (10.90 mmol, 62%) of Intermediate 6-5 was prepared in the same manner as in the synthesis of Intermediate 1-5 of Synthesis Example 1, except that 10 g (17.59 mmol) of Intermediate 6-4 was used instead of Intermediate 1-4.

Synthesis of Intermediate 6-6

10 g (18.67 mmol) of Intermediate 6-5, 10.56 g (37.34 mmol) of 2-bromoiodobenzene, 1.78 g (9.33 mmol) of CuI, and 5.16 g (37.34 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 5.68 g (8.21 mmol, 44%) of Intermediate 6-6.

Synthesis of Compound 6

10 g (14.46 mmol) of Intermediate 6-6 was dissolved in 100 ml of THF, and 5.78 ml (14.46 mmol, 2.5M in hexane) of n-buLi was slowly added thereto at −78° C. After stifling for 2 hours, 1.09 ml (18.80 mmol) of acetone was added thereto, and the mixture was heated to room temperature. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. A HCl aqueous solution (5 mol %, 12N) having the same amount as the catalyst was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 5.85 g (8.96 mmol, 62%) of Compound 6.

MS: m/z 652.26 [M]$^+$ $^1$H NMR (CDCl$_3$) δ 7.70 (1H), 7.67 (2H), 7.55 (2H), 7.48 (4H), 7.40 (1H), 7.32 (4H), 7.22 (2H), 7.20 (2H), 7.10 (2H), 7.08 (1H), 7.00 (2H), 6.87 (1H), 1.73 (6H)

Synthesis Example 7

Synthesis of Compound 7

Compound 7 was synthesized through Reaction Scheme 7 below.

Reaction Scheme 7

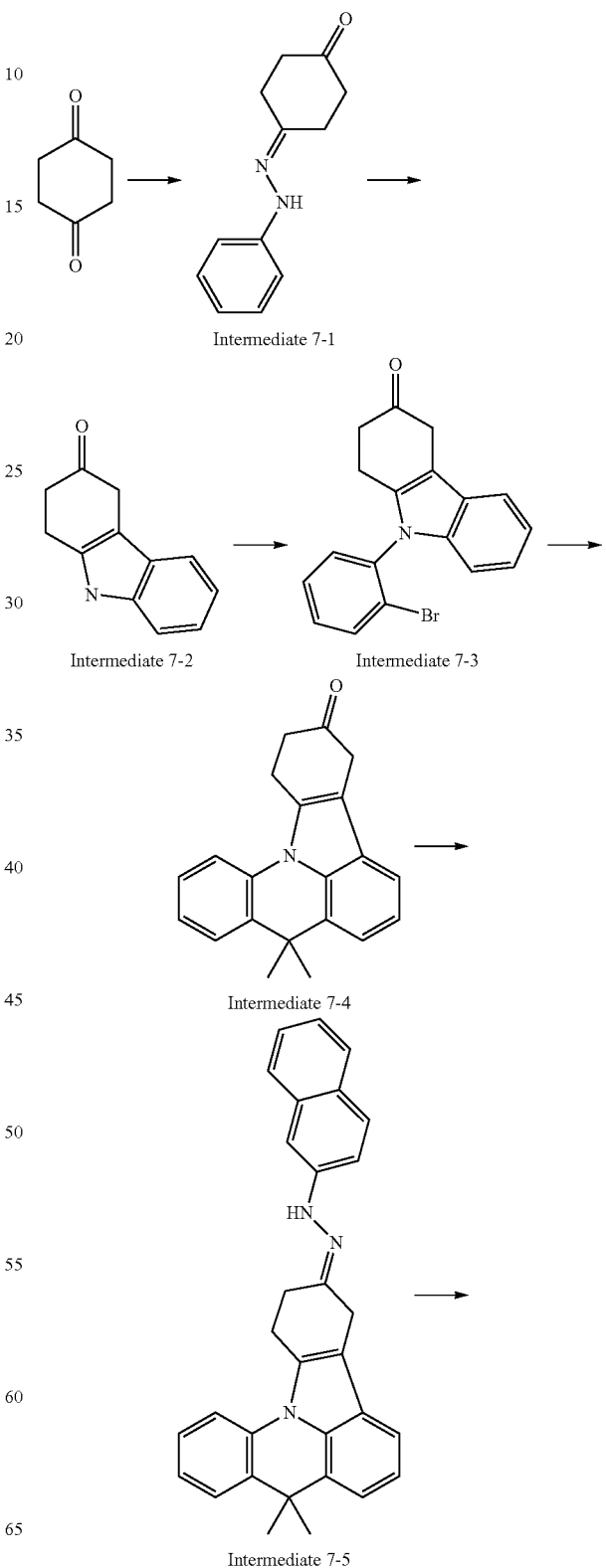

Intermediate 7-1

Intermediate 7-2

Intermediate 7-3

Intermediate 7-4

Intermediate 7-5

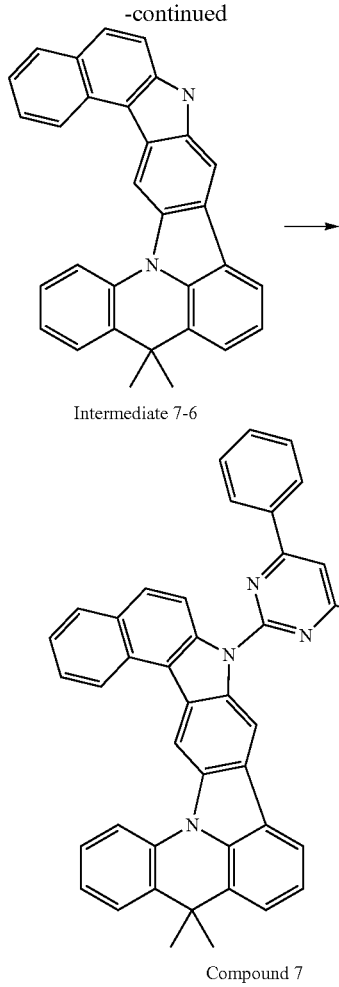

Intermediate 7-6

Compound 7

Synthesis of Intermediate 7-1

20 g (178.40 mmol) of 1,2-cyclohexyldione was dissolved in 500 ml of ethanol, and 6.25 g (58.87 mmol) of phenyl hydrazine was slowly added thereto. 0.13 ml (2.37 mmol) of acetic acid was added thereto, and the mixture was heated to 40° C. Then, the resultant was cooled to room temperature after 2 hours, and distilled water was added thereto to obtain a solid. The solid was filtered under reduced pressure to obtain 19.84 g (98.12 mmol, 55%) of Intermediate 7-1.

Synthesis of Intermediate 7-2

20 g (98.89 mmol) of Intermediate 7-1 was dissolved in 100 ml of acetic acid, and 10 ml of trifluoroacetic acid was added thereto. The mixture was stirred at room temperature for 2 hours, and distilled water was added thereto. Then, the mixture was neutralized with a NaOH aqueous solution, subjected to extraction with EA, and dried with magnesium sulfate. The resultant was distilled under reduced pressure and separately purified using column chromatography to obtain 84 g (64.285 mmol, 65%) of Intermediate 7-2.

Synthesis of Intermediate 7-3

20 g (108.57 mmol) of Intermediate 7-2, 61.43 g (217.14 mmol) of 2-bromoiodobenzene, 10.35 g (54.29 mmol) of CuI, and 30 g (217.14 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 16.62 g (48.86 mmol, 45%) of Intermediate 7-3.

Synthesis of Intermediate 7-4

20 g (58.79 mmol) of Intermediate 7-3 was dissolved in 200 ml of THF, and 23.51 ml (58.79 mmol, 2.5M in hexane) of n-buLi was slowly added thereto at −78° C. After stifling for 2 hours, 4.44 ml (76.42 mmol) of acetone was added thereto, and the mixture was heated to room temperature. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 200 ml of acetic acid. A HCl aqueous solution (5 mol %, 12N) having the same amount as the catalyst was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 11.52 g (38.21 mmol, 47%) of Intermediate 7-4.

Synthesis of Intermediate 7-5

20 g (66.36 mmol) of Intermediate 7-4 was dissolved in 500 ml of ethanol, and 12.60 g (79.63 mmol) of 2-naphthyl hydrazine was slowly added thereto. 0.15 ml (2.65 mmol) of acetic acid was added thereto, and the mixture was heated to 40° C. After 2 hours, the resultant was cooled to room temperature, and distilled water was added thereto to produce a solid. The solid was filtered under reduced pressure to obtain 21.10 g (47.78 mmol, 72%) of Intermediate 7-5.

Synthesis of Intermediate 7-6

10 g (22.65 mmol) of Intermediate 7-5 was dissolved in 50 ml of acetic acid, and 5 ml of trifluoroacetic acid was added thereto. The mixture was stirred at room temperature for 2 hours, and distilled water was added thereto. Then, the mixture was neutralized with a NaOH aqueous solution and dried with magnesium sulfate. The resultant was distilled under reduced pressure and separately purified using column chromatography to obtain 12.69 g (30.10 mmol, 63%) of Intermediate 7-6.

Synthesis of Compound 7

10 g (14.46 mmol) of Intermediate 7-6 was dissolved in 50 ml of dimethylformamide (DMF), and the solution was added to a reactor in which 1.40 g (35.59 mmol, 60% dispersion in mineral oil) of NaH was dissolved in 50 ml of DMF. After one hour, 7.59 g (28.47 mmol) of 2-chloro-4,6-diphenylpyrimidine dissolved in 50 ml of DMF was added thereto. The mixture was stirred for 12 hours, and then distilled water was added thereto to produce a solid. The solid was filtered under reduced pressure and recrystallized using EA and DMF to obtain 6.05 g (13.52 mmol, 57%) of Compound 7.

MS: m/z 652.26 [M]$^+$

¹H NMR (CDCl₃) δ 7.70 (1H), 7.67 (2H), 7.55 (1H), 7.48 (4H), 7.40 (2H), 7.37 (1H), 7.32 (6H), 7.22 (2H), 7.20 (2H), 7.10 (2H), 7.08 (1H), 6.95 (1H), 6.92 (1H), 1.67 (6H)
Synthesis Example 8
Synthesis of Compound 8
Compound 8 was synthesized through Reaction Scheme 8 below.
Reaction Scheme 8
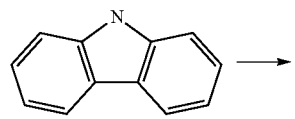
Intermediate 8-1
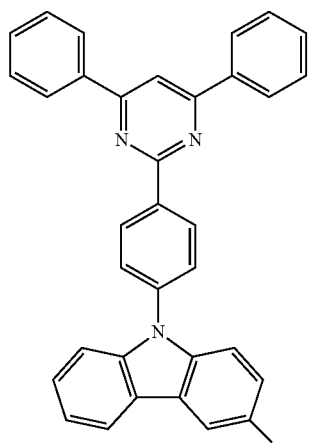
Intermediate 8-2
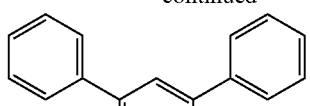
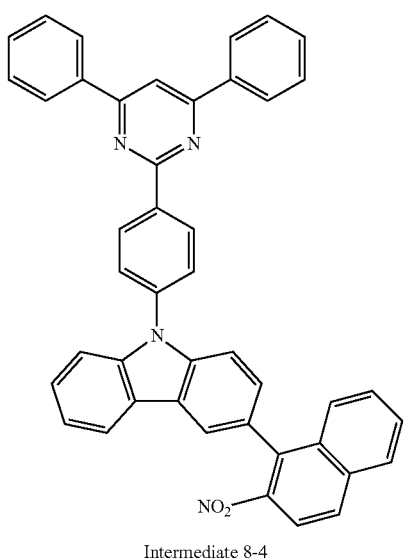
Intermediate 8-3
Intermediate 8-4
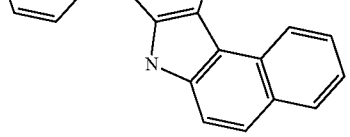
Intermediate 8-5

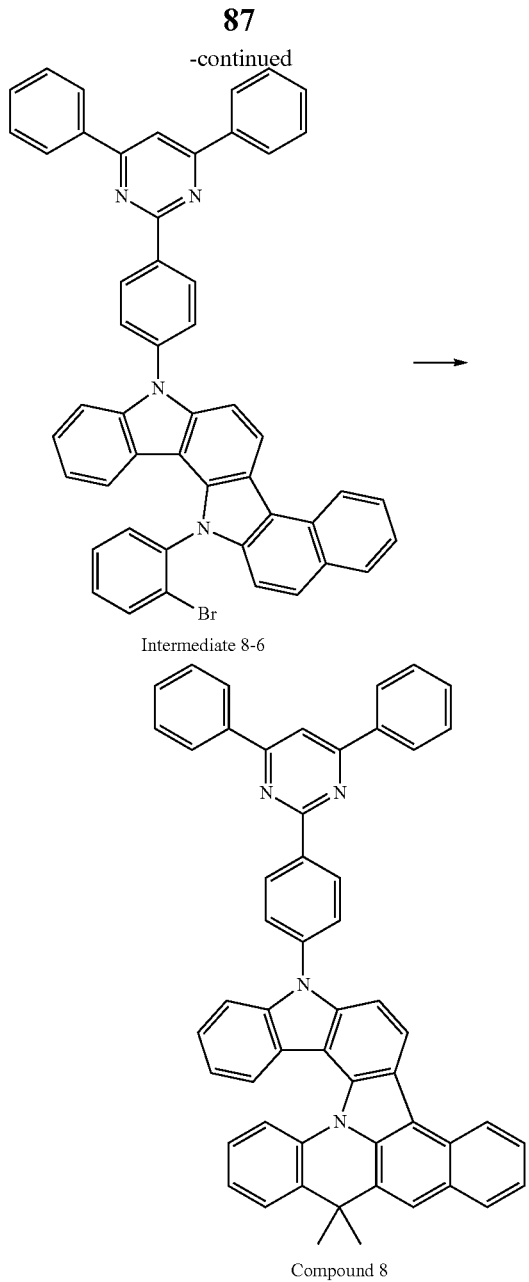

Intermediate 8-6

Compound 8

Synthesis of Intermediate 8-1

33.99 g (71.77 mmol, 60%) of Intermediate 8-1 was prepared in the same manner as in the synthesis of Intermediate 1-1 of Synthesis Example 1, except that 49.21 g (143.53 mmol) of 2-(4-chlorophenyl)-4,6-diphenylpyrimidine was used instead of 2-chloro-4,6-diphenyltriazine.

Synthesis of Intermediate 8-2

19.60 g (35.48 mmol, 84%) of Intermediate 8-2 was prepared in the same manner as in the synthesis of Intermediate 1-2 of Synthesis Example 1, except that 20 g (42.23 mmol) of Intermediate 8-1 was used instead of Intermediate 1-1 and 8.27 g (46.46 mmol) of NBS was used.

Synthesis of Intermediate 8-3

20 g (36.20 mmol) of Intermediate 8-2 was dissolved in 200 ml of tetrahydrofuran (THF), and 14.48 ml (36.20 mmol, 2.5M in hexane) of n-buLi was slowly added thereto at −78° C. After stifling for 1 hour, 5.42 ml (47.06 mmol) of trimethyl borate was added thereto, and the mixture was heated to room temperature and stirred for 12 hours. Distilled water was added thereto, and the mixture was subjected to extraction using EA, dried using magnesium sulfate, and distilled under reduced pressure. The resultant was separately purified using column chromatography to obtain 8.11 g (15.20 mmol, 42%) of Intermediate 8-3.

Synthesis of Intermediate 8-4

10 g (18.75 mmol) of Intermediate 8-3 and 5.67 g (22.50 mmol) of bromo-2-nitronaphthalene, 0.66 g (0.56 mmol) of Pd(PPh$_3$)$_4$, 18.39 ml (37.49 mmol) of 2M K$_2$CO$_3$ aqueous solution, 80 ml of toluene, and 30 ml of ethanol were refluxed while stirring. After 4 hours, the mixture was cooled to room temperature, and distilled water was added thereto. The mixture was subjected to extraction using EA, dried using magnesium sulfate, and distilled under reduced pressure. The resultant was separately purified using column chromatography to obtain 8.92 g (13.50 mmol, 72%) of Intermediate 8-4.

Synthesis of Intermediate 8-5

5.92 g (9.69 mmol, 64%) of Intermediate 8-5 was prepared in the same manner as in the synthesis of Intermediate 1-5 of Synthesis Example 1, except that 10 g (15.13 mmol) of Intermediate 8-4 was used instead of Intermediate 1-4.

Synthesis of Intermediate 8-6

10 g (16.35 mmol) of Intermediate 8-5, 9.25 g (32.69 mmol) of 2-bromoiodobenzene, 1.56 g (8.17 mmol) of CuI and 4.52 g (32.69 mmol) of potassium carbonate were dissolved in xylene in a nitrogen atmosphere, and the mixture was refluxed while stifling. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 5.77 g (7.52 mmol, 46%) of Intermediate 8-6.

Synthesis of Compound 8

10 g (13.03 mmol) of Intermediate 8-6 was dissolved in 100 ml of THF, and 5.21 ml (13.03 mmol, 2.5M in hexane) of n-buLi was slowly added thereto at −78° C. After stifling for 2 hours, 0.98 ml (16.93 mmol) of acetone was added thereto, and the mixture was heated to room temperature. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. A HCl aqueous solution (5 mol %, 12N) in a catalytic amount was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 5.70 g (7.82 mmol, 60%) of Compound 8.

MS: m/z 728.29 [M]$^+$ $^1$H NMR (CDCl$_3$) δ 7.67 (2H), 7.55 (2H), 7.50 (2H), 7.48 (4H), 7.40 (1H), 7.32 (6H), 7.30 (2H), 7.22 (2H), 7.20 (2H), 7.10 (1H), 7.08 (1H), 7.00 (2H), 6.87 (1H), 1.73 (6H)

Synthesis Example 9

Synthesis of Compound 9

Compound 9 was synthesized through Reaction Scheme 9 below.

Reaction Scheme 9

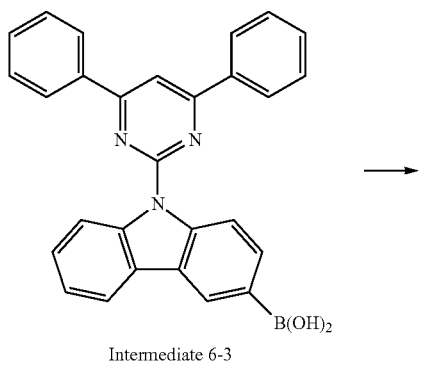
Intermediate 6-3

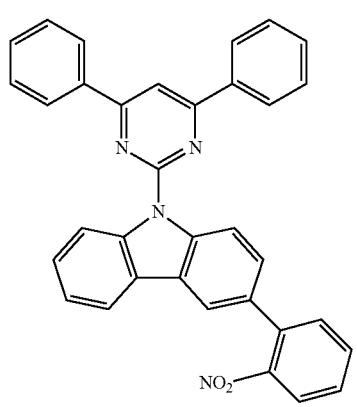
Intermediate 9-4

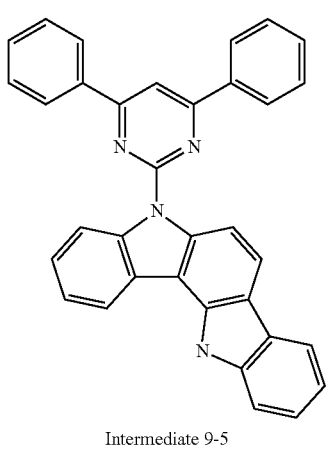
Intermediate 9-5

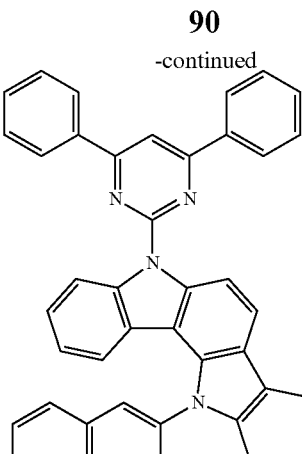
Intermediate 9-6

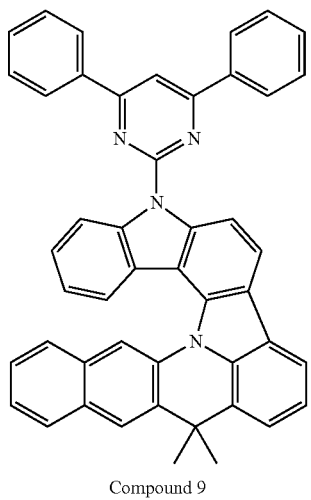 [SMILES: CC1(C)c2cc3ccccc3cc2-n2c3c1cccc3c1ccc3c(c4ccccc4n3-c3nc(-c4ccccc4)cc(-c4ccccc4)n3)c12]
Compound 9

Synthesis of Intermediate 9-4

8.81 g (17.00 mmol, 75%) of Intermediate 9-4 was prepared in the same manner as in the synthesis of Intermediate 6-3 of Synthesis Example 6, except that 5.49 g (27.19 mmol) of bromo-2-nitrobenzene was used instead of bromo-2-nitronaphthalene.

Synthesis of Intermediate 9-5

6.09 g (12.53 mmol, 65%) of Intermediate 9-5 was prepared in the same manner as in the synthesis of Intermediate 1-5 of Synthesis Example 1, except that 10 g (19.28 mmol) of Intermediate 9-4 was used instead of Intermediate 1-4.

Synthesis of Intermediate 9-6

10 g (20.59 mmol) of Intermediate 9-5, 13.71 g (41.19 mmol) of 2-bromoiodonaphthalene, 1.96 g (10.30 mmol) of CuI and 5.69 g (41.19 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using MC, dried using magnesium sulfate, and distilled under reduced pressure. The resultant was separately purified using column chromatography to obtain 6.12 g (8.86 mmol, 43%) of Intermediate 9-6.

Synthesis of Compound 9

10 g (14.46 mmol) of Intermediate 9-6 was dissolved in 100 ml of THF, and 5.78 ml (14.46 mmol, 2.5M in hexane) of n-buLi was slowly added thereto at −78° C. After stifling for 2 hours, 1.09 ml (18.80 mmol) of acetone was added thereto, and the mixture was heated to room temperature. Then, a NaHCO$_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. A HCl aqueous solution (5 mol %, 12N) having the same amount as the catalyst was added thereto and the mixture was refluxed while stifling. After 12 hours, the mixture was cooled to room temperature, and distilled water was added thereto. The mixture was subjected to extraction using MC, dried using magnesium sulfate, and distilled under reduced pressure. The resultant was separately purified using column chromatography to obtain 6.14 g (9.40 mmol, 65%) of Compound 9.

MS: m/z 652.26 [M]$^+$ $^1$H NMR (CDCl$_3$) δ 7.70 (2H), 7.60 (2H), 7.55 (2H), 7.50 (1H), 7.48 (4H), 7.40 (1H), 7.37 (1H), 7.32 (4H), 7.30 (2H), 7.22 (2H), 7.08 (1H), 7.00 (2H), 6.95 (1H), 6.92 (1H), 1.73 (6H)

Synthesis Example 10

Synthesis of Compound 10

Compound 10 was synthesized through Reaction Scheme 10 below.

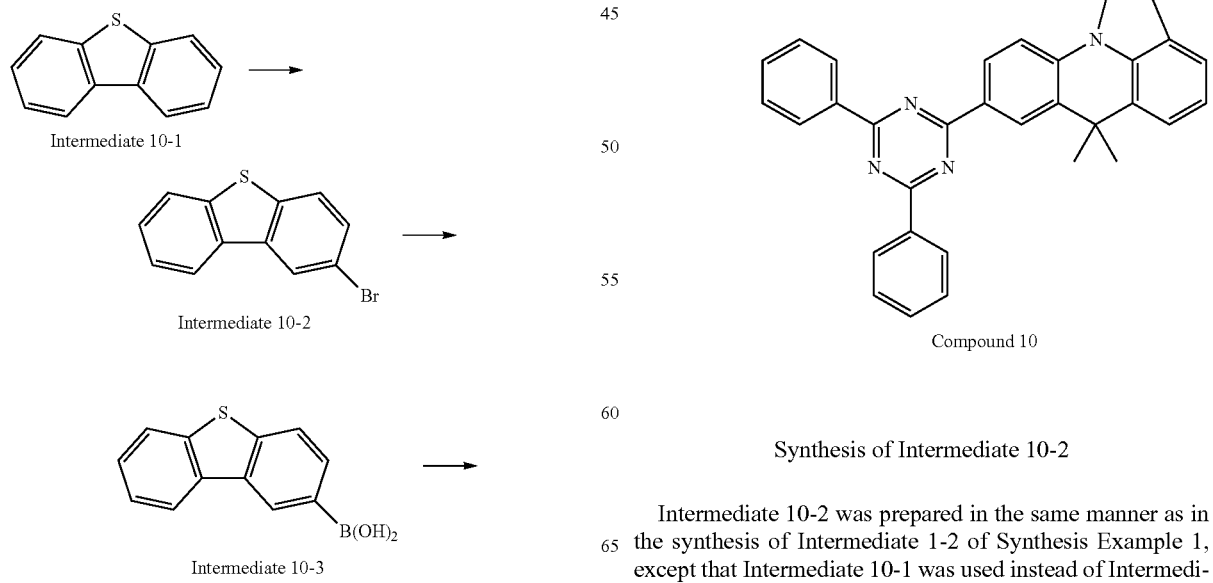

Synthesis of Intermediate 10-2

Intermediate 10-2 was prepared in the same manner as in the synthesis of Intermediate 1-2 of Synthesis Example 1, except that Intermediate 10-1 was used instead of Intermediate 1-1.

Synthesis of Intermediate 10-3

Intermediate 10-3 was prepared in the same manner as in the synthesis of Intermediate 1-3 of Synthesis Example 1, except that Intermediate 10-2 was used instead of Intermediate 1-2.

Synthesis of Intermediate 10-4

Intermediate 10-4 was prepared in the same manner as in the synthesis of Intermediate 1-4 of Synthesis Example 1, except that Intermediate 10-3 was used instead of Intermediate 1-3.

Synthesis of Intermediate 10-5

Intermediate 10-5 was prepared in the same manner as in the synthesis of Intermediate 1-5 of Synthesis Example 1, except that Intermediate 10-4 was used instead of Intermediate 1-4.

Synthesis of Intermediate 10-6

Intermediate 10-6 was prepared in the same manner as in the synthesis of Intermediate 1-6 of Synthesis Example 1, except that Intermediate 10-5 was used instead of Intermediate 1-5 and 2-(4-bromo-3-iodo-phenyl)-4,6-diphenyl-triazine was used instead of 2-bromoidobenzene.

Synthesis of Compound 10

Compound 10 was synthesized with a yield of 52% in the same manner as in the synthesis of Compound 1 of Synthesis Example 1, except that Intermediate 10-6 was used instead of Intermediate 1-6.

MS: m/z 620.20 [M]$^+$ $^1$H NMR (CDCl$_3$) δ 7.86 (2H), 7.78 (1H), 7.48 (4H), 7.37 (1H), 7.33 (1H), 7.32 (4H), 7.30 (2H), 7.22 (2H), 7.20 (1H), 6.95 (1H), 6.92 (1H), 1.67 (6H)

Synthesis Example 11

Synthesis of Compound 11

Compound 11 was prepared with a yield of 54% in the same manner as in the synthesis of Synthesis Example 10, except that Intermediate 11-1 was used instead of Intermediate 10-1.

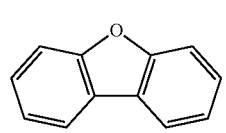

Intermediate 11-1

MS: m/z 604.23 [M]$^+$ $^1$H NMR (CDCl$_3$) δ 7.49 (1H), 7.48 (4H), 7.42 (2H), 7.37 (1H), 7.32 (4H), 7.30 (2H), 7.22 (2H), 7.20 (1H), 7.19 (2H), 7.13 (1H), 6.95 (1H), 6.92 (1H), 1.67 (6H)

Synthesis Example 12

Synthesis of Compound 12

Compound 12 was synthesized through Reaction Scheme 12 below.

Reaction Scheme 12

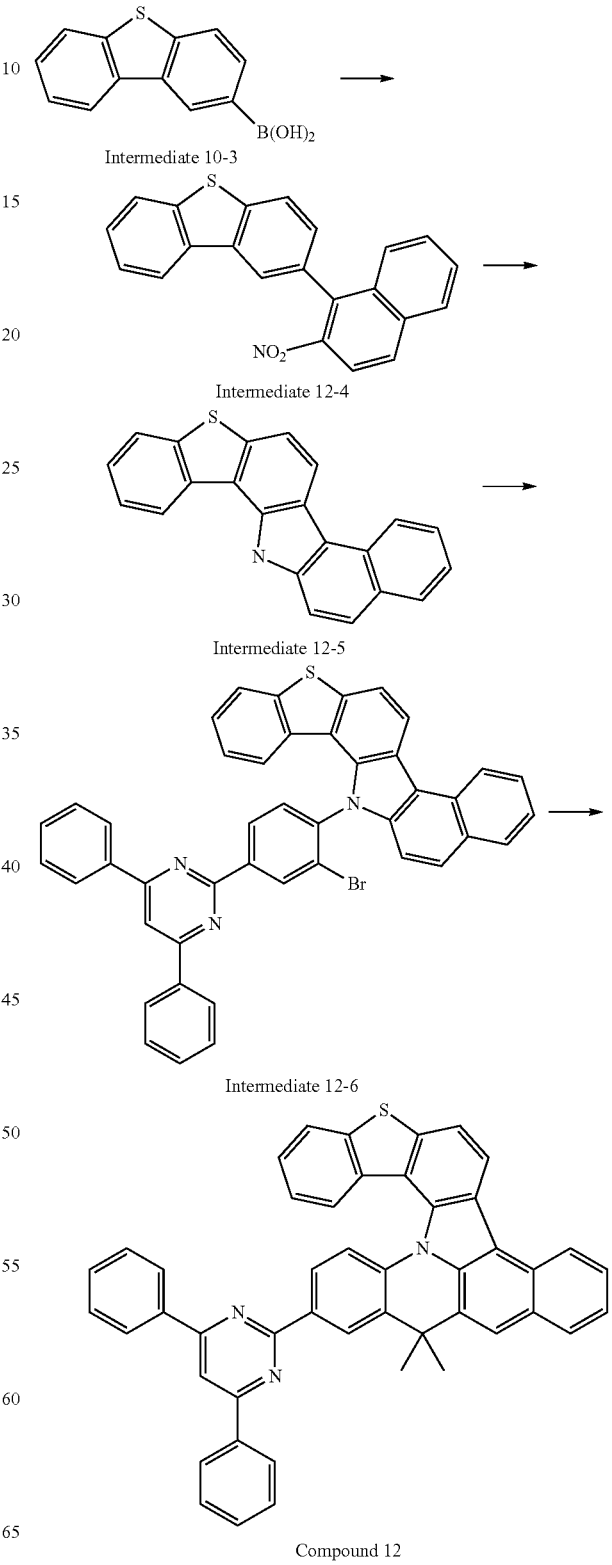

Synthesis of Intermediate 12-4

Intermediate 12-4 was prepared in the same manner as in the synthesis of Intermediate 12-4 of Synthesis Example 1, except that Intermediate 10-3 was used instead of Intermediate 1-3 and bromo-2-nitronaphthalene was used instead of bromo-2-nitrobenzene.

Synthesis of Intermediate 12-5

Intermediate 12-5 was prepared in the same manner as in the synthesis of Intermediate 12-5 of Synthesis Example 1, except that Intermediate 12-4 was used instead of Intermediate 1-4.

Synthesis of Intermediate 12-6

Intermediate 12-6 was prepared in the same manner as in the synthesis of Intermediate 12-6 of Synthesis Example 1, except that Intermediate 12-5 was used instead of Intermediate 5-5 and 2-(4-bromo-3-iodo-phenyl)-4,6-diphenyl-pyrimidine was used instead of 2-bromoidobenzene.

Synthesis of Compound 12

Compound 12 was synthesized with a yield of 48% in the same manner as in the synthesis of Compound 1 of Synthesis Example 1, except that Intermediate 12-6 was used instead of Intermediate 1-6.

MS: m/z 669.22 $[M]^+$
$^1$H NMR (CDCl$_3$) δ 7.86 (2H), 7.78 (1H), 7.67 (2H), 7.48 (4H), 7.32 (6H), 7.31 (2H), 7.30 (2H), 7.28 (1H), 7.22 (2H), 7.20 (1H), 6.87 (1H), 1.73 (6H)

Synthesis Example 13

Synthesis of Compound 13

Compound 13 was prepared with a yield of 49% in the same manner as in the synthesis of Synthesis Example 12, except that Intermediate 13-3 was used instead of Intermediate 12-3.

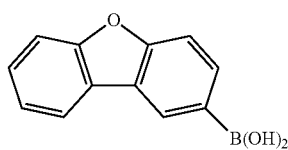

Intermediate 13-3

MS: m/z 653.25 $[M]^+$
$^1$H NMR (CDCl$_3$) δ 7.67 (2H), 7.49 (1H), 7.48 (4H), 7.42 (2H), 7.32 (6H), 7.30 (2H), 7.28 (1H), 7.22 (2H), 7.20 (1H), 7.19 (2H), 7.13 (1H), 6.87 (1H), 1.73 (6H)

Example 1

An ITO glass substrate (50×50 mm, 15 Ω/cm$^2$) that is a glass substrate for an organic light-emitting diode (OLED) manufactured by Samsung-Corning was ultrasonically cleaned by using distilled water and then isopropanol and UV/ozone cleaned for 30 minutes. The cleaned glass substrate to which a transparent electrode line is attached was installed on a substrate holder of a vacuum deposition apparatus, and 4,4',4''-tris(N-(2-naphthyl)-N-phenyl-amino)-triphenylamine (2T-NATA) was deposited (using a resistance heating deposition method) on an ITO electrode (anode) to form an HIL with a thickness of 60 nm. N,N'-bis(naphthalen-1-yl)-N,N-bis(phenyl)benzidine (NPB) was deposited on the HIL to form an HTL with a thickness of 20 nm, and Compound 1 (host) and tris(2-phenylpyridine)iridium (III) (Ir(ppy)$_3$) (dopant, 8 wt %) were co-deposited on the HTL to form an EML with a thickness of 30 nm. Then, tris-(8-hydroxyquinoline)aluminium-(III) (Alq$_3$) was deposited thereon to form an ETL with a thickness of 20 nm. 8-hydroxyquinolinolato-lithium (LiQ) was deposited on the ETL to form an EIL with a thickness of 1 nm, and Al was deposited on the EIL to form a cathode with a thickness of 100 nm, thereby manufacturing an organic light-emitting diode.

Example 2

An organic light-emitting diode was manufactured in the same manner as in Example 1, except that Compound 2 was used instead of Compound 1 as a host when the EML was formed.

Example 3

An organic light-emitting diode was manufactured in the same manner as in Example 1, except that Compound 3 was used instead of Compound 1 as a host when the EML was formed.

Example 4

An organic light-emitting diode was manufactured in the same manner as in Example 1, except that Compound 4 was used instead of Compound 1 as a host when the EML was formed.

Example 5

An organic light-emitting diode was manufactured in the same manner as in Example 1, except that Compound 10 was used instead of Compound 1 as a host when the EML was formed.

Example 6

An organic light-emitting diode was manufactured in the same manner as in Example 1, except that Compound 11 was used instead of Compound 1 as a host when the EML was formed.

Comparative Example 1

An organic light-emitting diode was manufactured in the same manner as in Example 1, except that 4,4'-bis(9-carbazolyl)biphenyl (CBP) was used instead of Compound 1 as a host when the EML was formed.

Comparative Example 2

An organic light-emitting diode was manufactured in the same manner as in Example 1, except that Compound A was used instead of Compound 1 as a host when the EML was formed.

Compound A

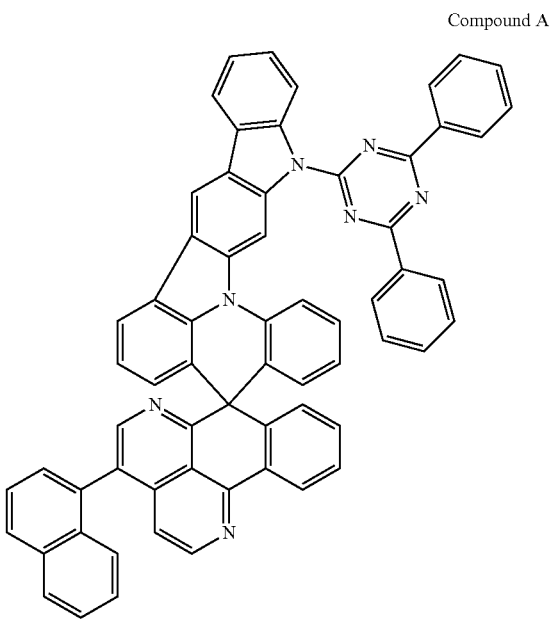 [SMILES: c1ccc(-c2nc(-c3ccccc3)nc(-n3c4ccccc4c4cc5c6cccc7c6n(c5cc43)-c3ccccc3C73c4ccccc4-c4nccc5c(-c6cccc7ccccc67)cnc3c45)n2)cc1]

Example 7

An organic light-emitting diode was manufactured in the same manner as in Example 1, except that Compound 5 was used instead of Compound 1 as a host, and Ir(piq)$_2$(acac) was used instead of Ir(ppy)$_3$ as a dopant when the EML was formed.

Example 8

An organic light-emitting diode was manufactured in the same manner as in Example 7, except that Compound 6 was used instead of Compound 5 as a host when the EML was formed.

Example 9

An organic light-emitting diode was manufactured in the same manner as in Example 7, except that Compound 7 was used instead of Compound 5 as a host when the EML was formed.

Example 10

An organic light-emitting diode was manufactured in the same manner as in Example 7, except that Compound 8 was used instead of Compound 5 as a host when the EML was formed.

Example 11

An organic light-emitting diode was manufactured in the same manner as in Example 7, except that Compound 9 was used instead of Compound 5 as a host when the EML was formed.

Example 12

An organic light-emitting diode was manufactured in the same manner as in Example 7, except that Compound 12 was used instead of Compound 5 as a host when the EML was formed.

Example 13

An organic light-emitting diode was manufactured in the same manner as in Example 7, except that Compound 13 was used instead of Compound 5 as a host when the EML was formed.

Comparative Example 3

An organic light-emitting diode was manufactured in the same manner as in Example 7, except that CBP was used instead of Compound 5 as a host when the EML was formed.

Evaluation Example 1

Driving voltage, efficiency, and color purity of the organic light-emitting diodes manufactured in Examples 1 to 13 and Comparative Examples 1 to 3 were measured by using the following methods, and the results are shown in Table 1 below.

- Color coordinates: measured using a luminance meter PR650 while supplying power with a current-voltmeter (Keithley SMU 236).
- Brightness: measured using a luminance meter PR650 while supplying power with a current-voltmeter (Keithley SMU 236).
- Efficiency: measured using a luminance meter PR650 while supplying power with a current-voltmeter (Keithley SMU 236).
- Meanwhile, lifespan T95 indicates a time period (hr) during which an initial brightness (at 10 mA/cm$^2$), set at 100%, decreased to 95%.

TABLE 1

|  | EML | | Driving | Efficiency | Color | Lifespan |
|---|---|---|---|---|---|---|
|  | Host | Dopant | voltage (V) | (Cd/A) | coordinates | T95 (hr) |
| Example 1 | Compound 1 | Ir(ppy)$_3$ | 6.2 | 29.5 | (0.282 to 0.607) | 190 |
| Example 2 | Compound 2 | Ir(ppy)$_3$ | 6.3 | 28.5 | (0.280 to 0.606) | 210 |
| Example 3 | Compound 3 | Ir(ppy)$_3$ | 6.1 | 29.3 | (0.280 to 0.606) | 220 |
| Example 4 | Compound 4 | Ir(ppy)$_3$ | 6.4 | 27.5 | (0.281 to 0.607) | 180 |
| Example 5 | Compound 10 | Ir(ppy)$_3$ | 6.6 | 27.2 | (0.282 to 0.606) | 160 |

TABLE 1-continued

| | EML | | Driving | Efficiency | Color | Lifespan |
|---|---|---|---|---|---|---|
| | Host | Dopant | voltage (V) | (Cd/A) | coordinates | T95 (hr) |
| Example 6 | Compound 11 | Ir(ppy)$_3$ | 6.7 | 27.9 | (0.281 to 0.606) | 170 |
| Comparative Example 1 | CBP | Ir(ppy)$_3$ | 7.3 | 24.2 | (0.312 to 0.605) | 70 |
| Comparative Example 2 | Compound A | Ir(ppy)$_3$ | 7.8 | 21.5 | (0.320 to 0.602) | 120 |
| Example 5 | Compound 5 | Ir(piq)$_2$(acac) | 6.4 | 12.5 | (0.642 to 0.352) | 480 |
| Example 6 | Compound 6 | Ir(piq)$_2$(acac) | 5.5 | 14.3 | (0.645 to 0.350) | 520 |
| Example 7 | Compound 7 | Ir(piq)$_2$(acac) | 5.8 | 13.9 | (0.646 to 0.350) | 470 |
| Example 8 | Compound 8 | Ir(piq)$_2$(acac) | 6.0 | 12.8 | (0.646 to 0.349) | 450 |
| Example 9 | Compound 9 | Ir(piq)$_2$(acac) | 5.7 | 13.5 | (0.645 to 0.350) | 480 |
| Example 10 | Compound 12 | Ir(piq)$_2$(acac) | 5.8 | 13.4 | (0.645 to 0.350) | 440 |
| Example 11 | Compound 13 | Ir(piq)$_2$(acac) | 6.0 | 125 | (0.645 to 0.350) | 420 |
| Comparative Example 3 | CBP | Ir(piq)$_2$(acac) | 6.8 | 10.2 | (0.635 to 0.355) | 230 |

Referring to Table 1, driving voltage, efficiency, and color purity of the organic light-emitting diodes manufactured in Examples 1 to 6 were better than those of the organic light-emitting diodes manufactured in Comparative Examples 1 and 2, and driving voltage, efficiency, and color purity of the organic light-emitting diodes manufactured in Examples 5 to 11 were better than those of the organic light-emitting diode manufactured in Comparative Example 3.

As described above, according to the one or more of the above embodiments of the present invention, the organic light-emitting diode including the condensed-cyclic compound may have low driving voltage, high efficiency, and high color purity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A condensed-cyclic compound, the condensed-cyclic ring being represented by one of Formulae 3-1 to 3-8 below:

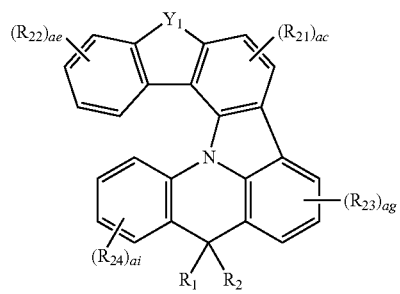

Formula 3-1

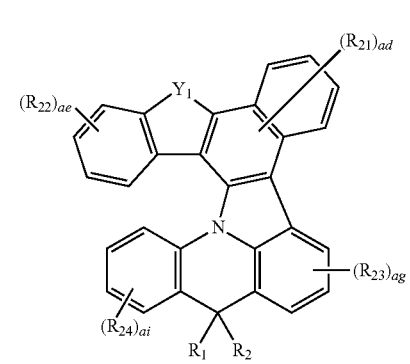

Formula 3-2

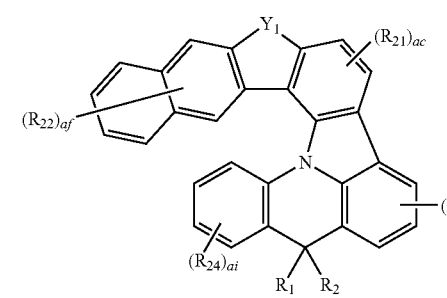

Formula 3-3

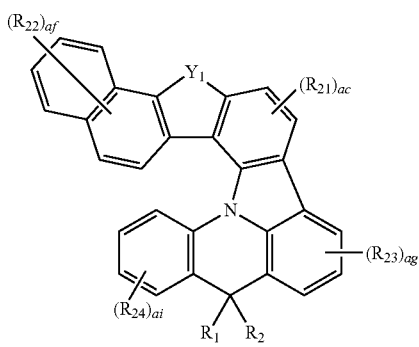

Formula 3-4

Formula 3-5

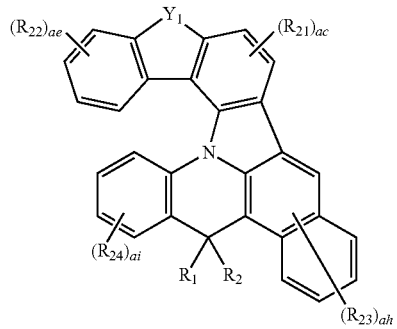

Formula 3-6

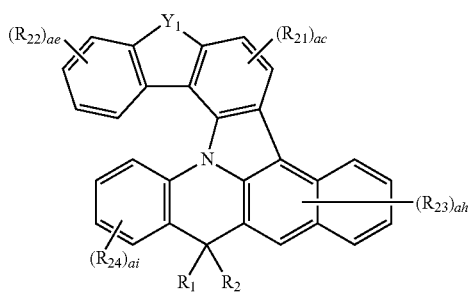

Formula 3-7

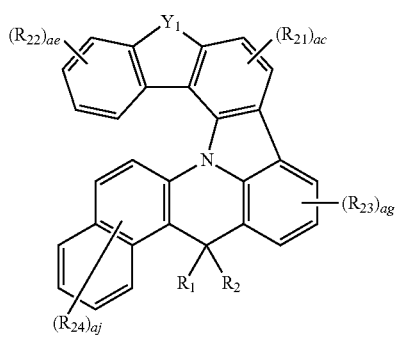

Formula 3-8

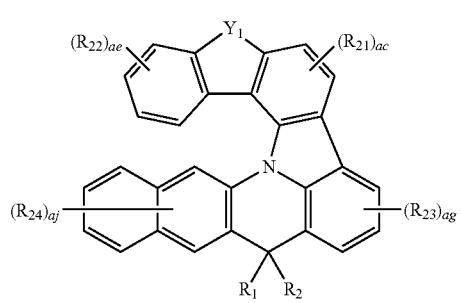

$R_{21}$ to $R_{24}$ being each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{50}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, and -($L_2$)ao-($R_{12}$)$_{ap}$;

ac being 1 or 2;

ag being an integer from 1 to 3;

ad, ae, and ai being each independently an integer from 1 to 4;

ah being an integer from 1 to 5;

af and aj being each independently an integer from 1 to 6;

$Y_1$ selected from O, S, and N-($L_1$)$_{aa}$-($R_{11}$)$_{ab}$;

$L_1$ being selected from a substituted or unsubstituted $C_6$-$C_{60}$ aryl group and a substituted or unsubstituted $C_2$-$C_{60}$ heteroaryl group;

aa being an integer from 0 to 5;

ab being an integer from 1 to 10;

$R_1$ and $R_2$ being each independently selected from a substituted or unsubstituted $C_1$-$C_{10}$ alkyl group, a substituted or unsubstituted $C_1$-$C_{10}$ alkoxy group, and a substituted or unsubstituted $C_6$-$C_{14}$ aryl group;

$R_{11}$ being selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted $C_2$-$C_{60}$ heteroaryl group;

$L_2$ being selected from a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group;

ao being 0, 1, or 2;

$R_{12}$ being selected from a substituted or unsubstituted 5-membered hetero ring, a substituted or unsubstituted 6-membered hetero ring, a substituted or unsubstituted 9-membered hetero ring, and a substituted or unsubstituted 10-membered hetero ring which include at least one nitrogen (N) as a ring-forming atom; and ap being 1 or 2.

2. A condensed-cyclic compound, the condensed-cyclic ring being represented by one of Formulae 3-1 to 3-8 below;

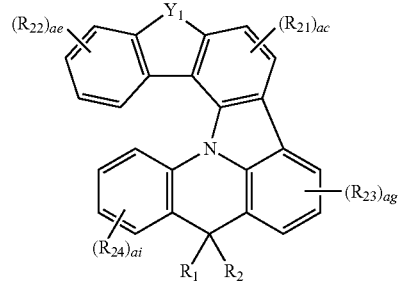
Formula 3-1

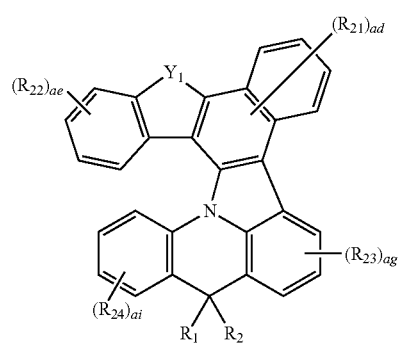
Formula 3-2

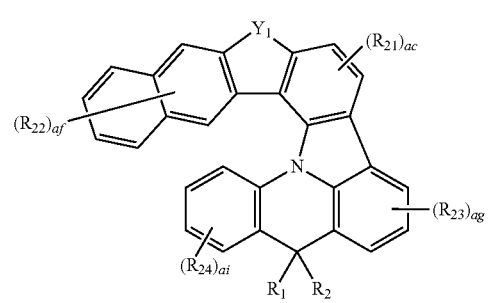
Formula 3-3

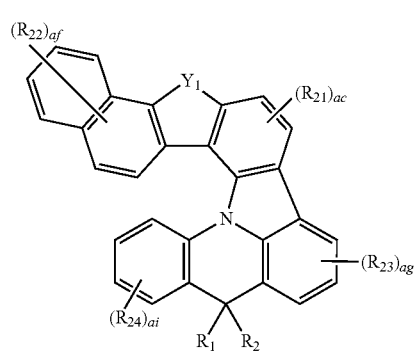
Formula 3-4

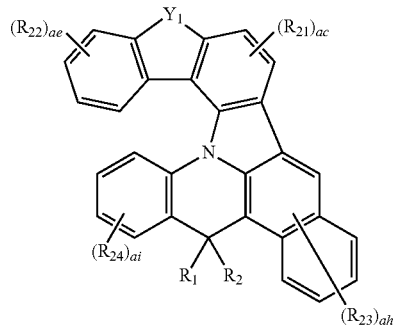
Formula 3-5

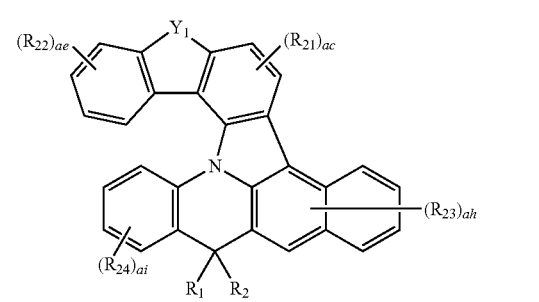
Formula 3-6

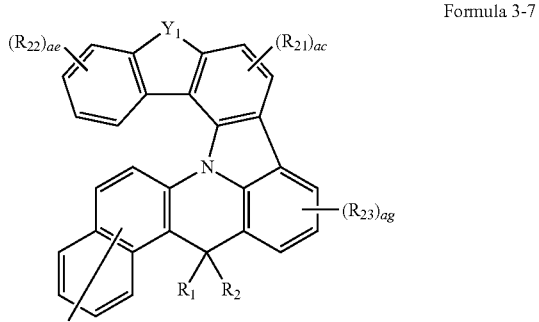
Formula 3-7

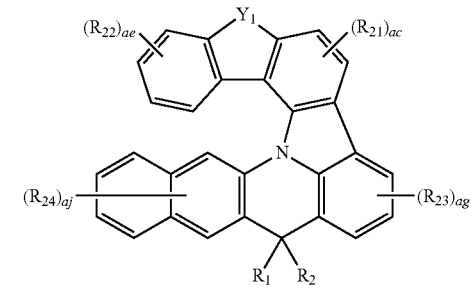
Formula 3-8 ac being 1 or 2;
ag being an integer from 1 to 3;
ad, ae, and ai being each independently an integer from 1 to 4;
ah being an integer from 1 to 5;
af and aj being each independently an integer from 1 to 6;
$Y_1$ being selected from S and O, $R_{21}$ to $R_{23}$ being hydrogen, ai and aj being 1, and $R_{24}$ being $-(L_2)_{ao}-(R_{12})_{ap}$ in Formulae 3-1 to 3-8;
$R_1$ and $R_2$ being each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted aryloxy group, a substituted or unsubstituted $C_6$-$C_{60}$ arylthio group, and a substituted or unsubstituted heteroaryl group, $R_1$ and $R_2$ being non-ring forming substituents which are not linked to each other and do not form a ring;

$L_2$ being selected from a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group;

ao being 0, 1, or 2;

$R_{12}$ being selected from a substituted or unsubstituted 5-membered hetero ring, a substituted or unsubstituted 6-membered hetero ring, a substituted r unsubstituted 9-membered hetero ring, and a substituted or unsubstituted 10-membered hetero ring which include at least one nitrogen (N) as a ring-forming atom; and ap being 1 or 2.

3. A condensed-cyclic compound, the condensed-cyclic ring being represented by one of Formulae 3-1 to 3-8 below:

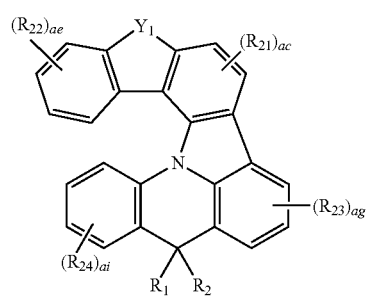

Formula 3-1

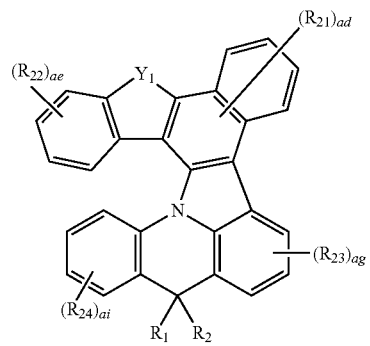

Formula 3-2

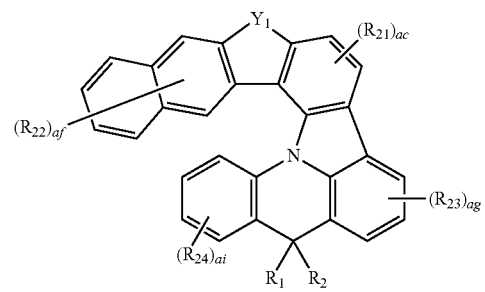

Formula 3-3

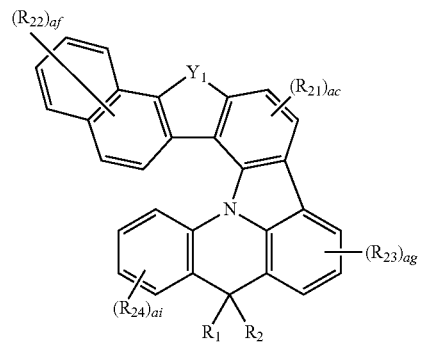

Formula 3-4

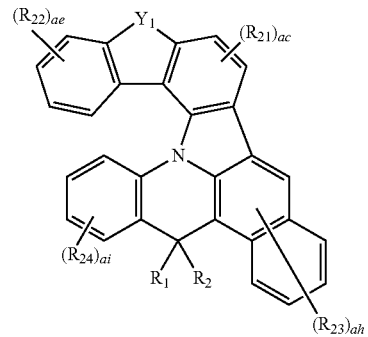

Formula 3-5

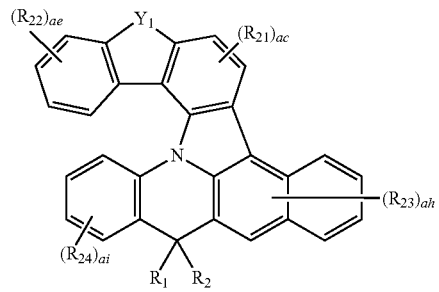

Formula 3-6

107

-continued

Formula 3-7

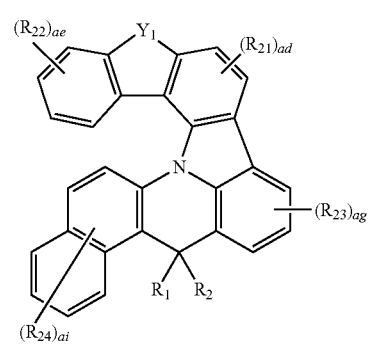

Formula 3-8

(R_{22})_{ae}, Y_1, (R_{21})_{ac}, (R_{24})_{aj}, N, (R_{23})_{ag}, R_1, R_2

$R_{21}$ to $R_{24}$ being each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, and -$(L_2)_{ao}$-$(R_{12})_{ap}$;

ac being 1 or 2;
ag being an integer from 1 to 3;
ad, ae, and ai being each independently an integer from 1 to 4;
ah being an integer from 1 to 5;
af and aj being each independently an integer from 1 to 6;
$Y_1$ being selected from O, S, and N-$(L_1)_{aa}$-$(R_{11})_{ab}$;
$L_1$ being selected from a substituted or unsubstituted $C_6$-$C_{60}$ aryl group and a substituted or unsubstituted $C_2$-$C_{60}$ heteroaryl group;
aa being an integer from 0 to 5;
ab being an integer from 1 to 10;
$R_1$ and $R_2$ being each independently selected from hydrogen, deuterium, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_4$-$C_{60}$ heteroaryl group, $R_1$ and $R_2$, being non-ring forming substituents which are not linked to each other and do not form a ring;

$R_{11}$ being selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group; and a substituted or unsubstituted $C_2$-$C_{60}$ heteroaryl group;

$L_2$ being selected from a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group;

ao being 0, 1, or 2;
$R_{12}$ being selected from a substituted or unsubstituted 5-membered hetero ring, a substituted or unsubstituted 6-membered hetero ring, a substituted or unsubstituted 9-membered hetero ring, and a substituted or unsubstituted 10-membered hetero ring which include at least one nitrogen (N) as a ring-forming atom; and
ap being 1 or 2.

4. The condensed-cyclic compound of claim 3:
$Y_1$ being N-$(L_1)_{aa}$-$(R_{11})_{ab}$ in Formulas 3-1 to 3-8;
$L_1$ being selected from a substituted or unsubstituted phenylene group, a substituted or unsubstituted pentalenylene group, a substituted or unsubstituted indenylene group, a substituted or unsubstituted naphtylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group;

aa being 0, 1, or 2;
$R_{11}$ being selected from a substituted or unsubstituted 5-membered hetero ring, a substituted or unsubstituted 6-membered hetero ring, a substituted or unsubstituted 9-membered hetero ring, and a substituted or unsubstituted 10-membered hetero ring which include at least one nitrogen (N) as a ring-forming atom; and ab being 1 or 2.

5. The condensed-cyclic compound of claim 4, $R_{11}$ being one of: a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group; and a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group substituted with at least one of deuterium a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group.

6. The condensed-cyclic compound of claim 4, $R_{11}$ being represented by any one of Formulae 9 to 15 below:

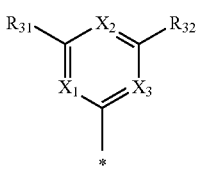

Formula 9

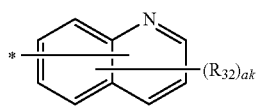

Formula 10

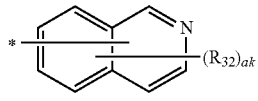

Formula 11

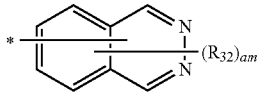

Formula 12

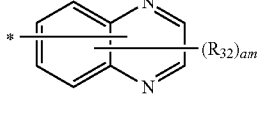

Formula 13

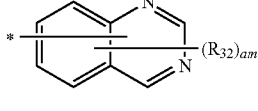

Formula 14

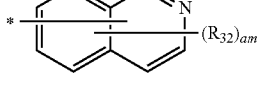

Formula 15

$X_1$ is N or $C(R_{33})$, $X_2$ is N or $C(R_{34})$, and $X_3$ is N or $C(R_{35})$, and at least one of $X_1$, $X_2$, and $X_3$ being N;

$R_{31}$ to $R_{35}$ being each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthryl group;

ak being an integer from 1 to 6;

am being an integer from 1 to 5; and

* being a binding site to $L_1$ or nitrogen in $Y_1$.

7. The condensed-cyclic compound of claim 6, $X_1$, $X_2$ and $X_3$ being N, $X_1$ and $X_3$ being N and $X_2$ being $C(R_{34})$, or $X_1$ and $X_2$ being N and $N_3$ being $C(R_{35})$ in Formula 9.

8. The condensed-cyclic compound of claim 3, $Y_1$ being N-$(L_1)_{aa}$-$(R_{11})_{ab}$ and $R_{21}$ to $R_{24}$ being hydrogen in Formulae 3-1 to 3-8.

9. The condensed-cyclic compound of claim 3, the condensed-cyclic compound being any one compound of Compounds 1, 2, 4-6 and 8-13 below:

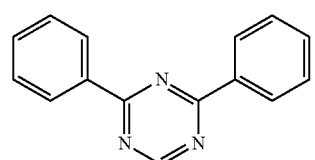

1

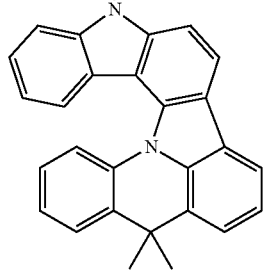

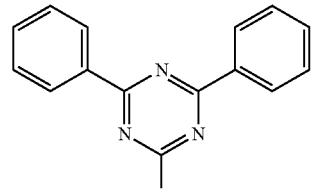

2

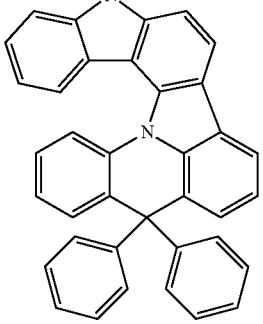

111
-continued
4
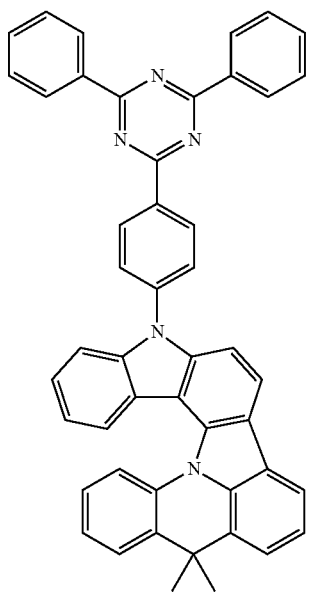
5
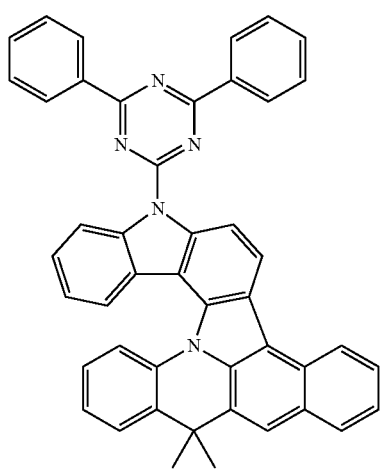
6
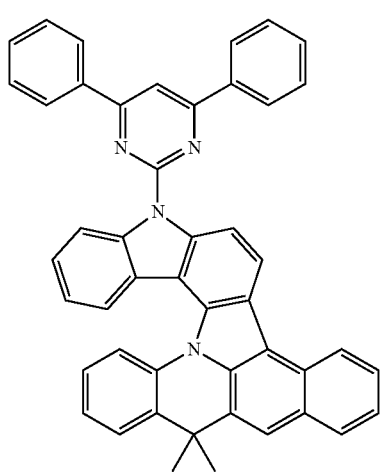
112
-continued
8
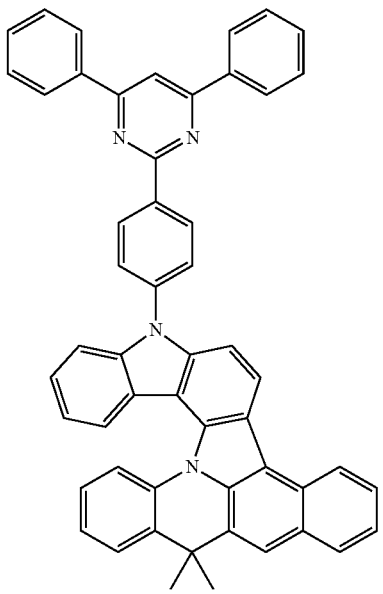
9
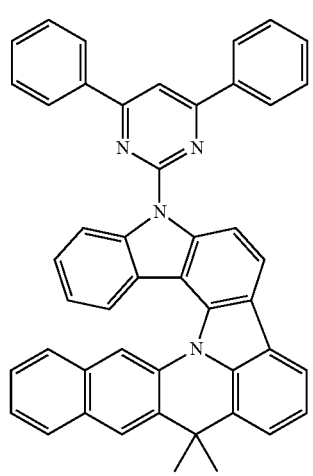
10
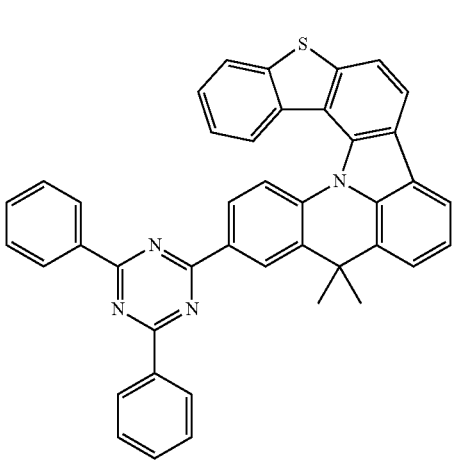

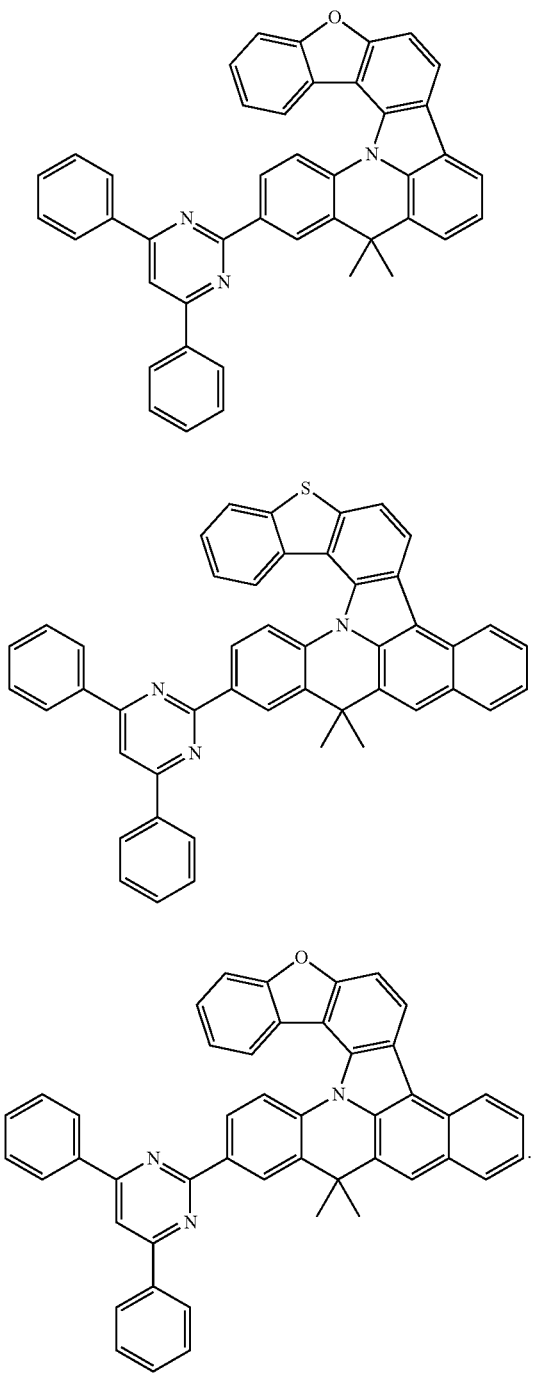

10. The condensed-cyclic compound of claim 3, $R_{21}$ to $R_{24}$ being each independently one of hydrogen; deuterium; a halogen atom; a hydroxyl group; a cyano group; a nitro group; an amino group; an aminidino group; hydrazine; hydrazone; a carboxyl group or a salt thereof; a sulfonic acid group or a salt thereof; a phosphoric acid group or a salt thereof; a $C_1$-$C_{20}$ alkyl group, and a $C_1$-$C_{20}$ alkoxy group; a $C_1$-$C_{20}$ alkyl group and a $C_1$-$C_{20}$ alkoxy group substituted with at least one of deuterium, a halogen atom, a hydroxyl group, a cyano group, a nitro group, an amino group, an aminidino group, hydrazine, hydrazone, a carboxyl group or a salt thereof, a sulfonic acid of a salt thereof, a phosphoric acid group or a salt thereof; a phenyl group, a naphthyl group, and an anthryl group; a $C_6$-$C_{14}$ aryl group, and a $C_2$-$C_{14}$ heteroaryl group; a $C_6$-$C_{14}$ aryl group and a $C_2$-$C_{14}$ heteroaryl group substituted with at least one of deuterium, a halogen atom, a hydroxyl group cyano group, a nitro group, an amino group, an aminidino group, hydrazine, hydrazone, a carboxyl group or a salt thereof, a sulfonic acid of a salt thereof, a phosphoric acid group or a salt thereof, a $C_1$-$C_{20}$ alkyl group, a $C_1$-$C_{20}$ alkoxy group, a phenyl group, a naphthyl group, and an anthryl group, and -$(L_2)_{ao}$-$(R_{12})_{ap}$.

11. The condensed-cyclic compound of claims 10, $R_{21}$ to $R_{24}$ being each independently one of: hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group; a methyl group, an ethyl group, a propyl group, a butyl group, a pentyl group, a hexyl group, a heptyl group, an octyl group, a methoxy group, an ethoxy group, a propoxy group, a butoxy group, and a pentoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, and an anthryl group; a phenyl group, a naphthyl group, an anthryl group, a pyridinyl group, a pyrimidinyl group, a pyrazinyl group, and a triazinyl group; a phenyl group, a naphthyl group, an anthryl group, a pyridinyl group, a pyrimidinyl group, a pyrazinyl group, and a triazinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and -$(L_2)_{ao}$-$(R_{12})_{ap}$;

$L_2$ being one of: a phenylene group, a naphthylene group, a fluorenylene group, and an anthrylene group; and a phenylene group, a naphthylene group, a fluorenylene group, and an anthrylene group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group;

ao being 0, 1, or 2;

$R_{12}$ being one of a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group; and a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxaline group, a quinazolinyl group, and a cinnolinyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and an anthryl group; and ap being 1 or 2.

12. An organic light-emitting diode, comprising:

a first electrode;

a second electrode disposed opposite to the first electrode; and an organic layer interposed between the first electrode and the second electrode, the organic layer comprising at least one condensed-cyclic compound according to claim 3.

13. The organic light-emitting diode of claim 12, the organic layer comprising at least one layer of a hole injection layer, a hole transport layer, a functional layer having both hole injecting and hole transporting capabilities, a buffer layer, an electron blocking layer, an emission layer, a hole blocking layer, an electron transport layer, an electron injection layer, and a functional layer having both electron injecting and electron transporting capabilities.

14. The organic light-emitting diode of claim 13, the organic layer comprising an emission layer that comprises the condensed-cyclic compound.

15. The organic light-emitting diode of claim 14, the condensed-cyclic compound contained in the emission layer functioning as a phosphorescent host, the emission layer further comprising a phosphorescent dopant.

16. The organic light-emitting diode of claim 15, the phosphorescent dopant comprising Ir, Pt, Os, Ti, Zr, Hf, Eu, Tb, or Tm.

\* \* \* \* \*